United States Patent [19]
Chakravarty et al.

[11] Patent Number: 5,157,026
[45] Date of Patent: Oct. 20, 1992

[54] OXO-PURINES AS ANGIOTENSIN II ANTAGONISTS

[75] Inventors: Prasun K. Chakravarty, Edison; William J. Greenlee, Teaneck; Nathan B. Mantlo, Westfield; Arthur A. Patchett, Westfield; Thomas F. Walsh, Westfield, all of N.J.

[73] Assignee: Merck & Co., Inc., Rahway, N.J.

[21] Appl. No.: 840,241

[22] Filed: Feb. 24, 1992

Related U.S. Application Data

[60] Division of Ser. No. 516,286, May 4, 1990, which is a continuation-in-part of Ser. No. 358,971, May 30, 1989, abandoned.

[51] Int. Cl.$^5$ .................... A61K 31/52; C07D 473/04
[52] U.S. Cl. ........................ 514/81; 514/263; 514/265; 544/244; 544/266; 544/267; 544/269; 544/270; 544/271; 544/272
[58] Field of Search .............. 544/244, 266, 267, 269, 544/270, 271, 272; 514/81, 263, 265

[56] References Cited

U.S. PATENT DOCUMENTS 4,804,658  2/1989  Manley et al. .................... 514/234.2
4,880,804  11/1989  Carini et al. ......................... 546/199

FOREIGN PATENT DOCUMENTS 0253310  1/1988  European Pat. Off. .

Primary Examiner—Bernard Dentz
Attorney, Agent, or Firm—William H. Nicholson; Joseph F. DiPrima

[57] ABSTRACT

Substituted Imidazo-fused 6-membered heterocycles of structural formula:

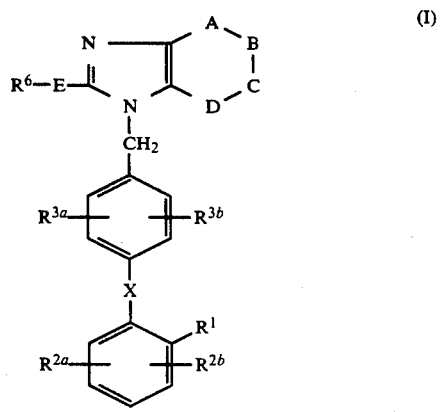

wherein A, B, C, and D are independently carbon atoms or nitrogen atoms are angiotensin II antagonists useful in the treatment of hypertension and congestive heart failure.

6 Claims, No Drawings

OXO-PURINES AS ANGIOTENSIN II ANTAGONISTS

SUMMARY OF THE INVENTION

This is a division of application Ser. No. 07/516,286, filed May 4, 1990, which is a continuation-in-part of copending application Ser. No. 358,971 filed May 30, 1989 now abandoned.

This invention relates to novel compounds of structural formula I which are angiotensin II antagonists useful in the treatment of hypertension, congestive heart failure, and elevated intraocular pressure.

It also relates to processes for preparing the novel compounds; pharmaceutical formulations comprising one or more of the compounds as active ingredient; and, a method of treatment of hypertension, congestive heart failure, and elevated intraocular pressure.

BACKGROUND OF THE INVENTION

Renin-angiotensin system (RAS) plays a central role in the regulation of normal blood pressure and seems to be critically involved in hypertension development and maintenance as well as congestive heart failure. Angiotensin II (AII), an octapeptide hormone is produced mainly in the blood during the cleavage of angiotensin I by angiotensin converting enzyme (ACE) localized on the endothelium of blood vessels of lung, kidney, and many other organs, and is the end product of the RAS. AII is a powerful arterial vasoconstricter that exerts its action by interacting with specific receptors present on cell membranes. One of the possible modes of controlling the RAS is angiotensin II receptor antagonism. Several peptide analogs of A II are known to inhibit the effect of this hormone by competitively blocking the receptors, but their experimental and clinical applications have been limited by the partial agonist activity and lack of oral absorption [M. Antonaccio. *Clin. Exp. Hypertens.* A4, 27-46 (1982); D. H. P. Streeten and G. H. Anderson, Jr. —*Handbook of Hypertension, Clinical Pharmacology of Antihypertensive Drugs*, ed. A. E. Doyle, Vol. 5, pp. 246-271, Elsevier Science Publisher, Amsterdam, The Netherlands, 1984].

Recently, several non-peptide compounds have been described as A II antagonists. Illustrative of such compounds are those disclosed in U.S. Pat. Nos. 4,207,324; 4,340,598; 4,576,958; 4,582,847; and 4,880,804; in European Patent Applications 028,834; 245,637; 253,310; and 291,969; and in articles by A. T. Chiu, et al. [*Eur. J. Pharm. Exp. Therap*, 157, 13-21 (1988)] and by P. C. Wong, et al. [*J. Pharm. Exp. Therap*, 247, 1-7 (1988)]. All of the U.S. Patents, European Patent Applications 028,834 and 253,310 and the two articles disclose substituted imidazole compounds which are generally bonded through a lower alkyl bridge to a substituted phenyl. European Patent Application 245,637 discloses derivatives of 4,5,6,7-tetrahydro-2H-imidazo[4,5-c]-pyridine-6-carboxylic acid and analogs thereof as antihypertensive agents.

None of the compounds disclosed in the above identified U.S. Patents, European Applications and articles have the heterobicyclic structure of the compounds of this invention.

DETAILED DESCRIPTION OF THE INVENTION

This invention relates to substituted imidazo-fused 6-membered ring heterocycles of the formula I shown below which are angiotensin II antagonists and are useful in the treatment of hypertension, congestive heart failure, and elevated intraocular pressure.

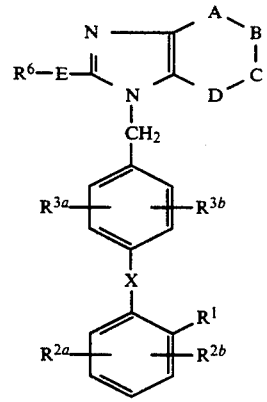

wherein:

$R^1$ is (a) $-CO_2R^4$, (b) $-SO_3R^5$, (c) $-NHSO_2CF_3$, (d) $-PO(OR^5)_2$, (e) $-SO_2-NH-R^9$, (f) $-CONHOR^5$, (g)

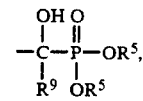

(h) $-SO_2NH$-heteroaryl, (i) $-CH_2SO_2NH$-heteroaryl, (j) $-SO_2NHCO-R^{23}$, (k) $-CH_2SO_2NHCO-R^{23}$, (l) $-CONH-SO_2R^{23}$, (m) $-CH_2CONH-SO_2R^{23}$, (n) $-NHSO_2NHCO-R^{23}$, (o) $-NHCONHSO_2-R^{23}$, (p) $-SO_2NHCONR^{23}$, (q)

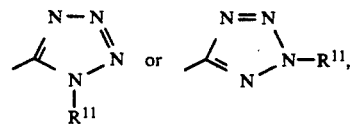

(r)

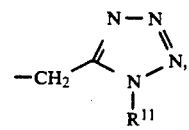

(s)

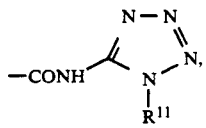

(t) —CONHNHSO$_2$CF$_3$,
(u)

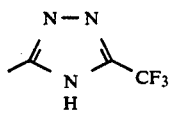

(v)

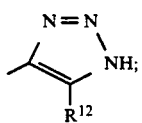

(w)

wherein heteroaryl is an unsubstituted, monosubstituted or disubstituted five- or six-membered aromatic ring which can optionally contain 1 to 3 heteroatoms selected from the group consisting of O, N or S and wherein the substituents are members selected from the group consisting of —OH, —SH, —C$_1$-C$_4$-alkyl, —C$_1$-C$_4$-alkoxy, halo(Cl, Br, F, I), —NO$_2$, —CO$_2$H, —CO$_2$—C$_1$-C$_4$-alkyl, —NH$_2$, —NH(C$_1$-C$_4$-alkyl) and —N(C$_1$-C$_4$-alkyl)$_2$;

R$^{2a}$ and R$^{2b}$ are independently H, halo(Cl, Br, I, F), —NO$_2$, —NH$_2$, C$_1$-C$_4$-alkylamino, di(C$_1$-C$_4$ alkyl)amino, —SO$_2$NHR$^9$, CF$_3$, C$_1$-C$_4$-alkyl, or C$_1$-C$_4$-alkoxy;

R$^{3a}$ is
(a) H,
(b) halo(Cl, Br, I, F)
(c) C$_1$-C$_6$-alkyl,
(d) C$_1$-C$_6$-alkoxy,
(e) C$_1$-C$_6$-alkoxyalkyl;

R$^{3b}$ is
(a) H,
(b) halo (Cl, Br, I, F)
(c) NO$_2$,
(d) C$_1$-C$_6$-alkyl,
(e) C$_1$-C$_6$-acyloxy,
(f) C$_1$-C$_6$-cycloalkyl
(g) C$_1$-C$_6$-alkoxy,
(h) —NHSO$_2$R$^4$,
(i) hydroxy C$_1$-C$_4$-alkyl,
(j) aryl C$_1$-C$_4$-alkyl
(k) C$_1$-C$_4$-alkylthio
(l) C$_1$-C$_4$-alkyl sulfinyl
(m) C$_1$-C$_4$-alkyl sulfonyl
(n) NH$_2$
(o) C$_1$-C$_4$-alkylamino
(p) C$_1$-C$_4$-dialkylamino
(q) fluoro C$_1$-C$_4$-alkyl
(r) —SO$_2$—NHR$^9$
(s) aryl or,
(t) furyl;
wherein aryl is phenyl or naphthyl optionally substituted with one or two substituents selected from the group consisting of halo(Cl, Br, I, F), C$_1$-C$_4$-alkyl, C$_1$-C$_4$-alkoxy, NO$_2$, CF$_3$, C$_1$-C$_4$-alkylthio, OH, NH$_2$, NH(C$_1$-C$_4$-alkyl), N(C$_1$-C$_4$-alkyl)$_2$, CO$_2$H, and CO$_2$—C$_1$-C$_4$-alkyl;

R$^4$ is H, straight chain or branched C$_1$-C$_6$ alkyl, aryl or —CH$_2$-aryl where aryl is as defined above;

R$^{4a}$ is C$_1$-C$_6$-alkyl, aryl or —CH$_2$-aryl where aryl is as defined above;

R$^5$ is H,

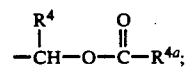

E is a single bond, —NR$^{13}$(CH$_2$)$_s$—, —S(O)$_x$—(CH$_2$)$_s$— where x is 0 to 2 and s is 0 to 5, —CH(OH)—, —O—, —CO—;

R$^6$ is
(a) aryl as defined above optionally substituted with 1 or 2 substituents selected from the group consisting of halo (Cl, Br, I, F) —O—C$_1$-C$_4$-alkyl, C$_1$-C$_4$-alkyl, —NO$_2$, —CF$_3$, —SO$_2$NR$^9$R$^{10}$, —S—C$_1$-C$_4$-alkyl, —OH, —NH$_2$, C$_3$-C$_7$-cycloalkyl, C$_3$-C$_{10}$-alkenyl;
(b) straight chain or branched C$_1$-C$_9$-alkyl, C$_2$-C$_6$-alkenyl or C$_2$-C$_6$-alkynyl each of which can be optionally substituted with a substituent selected from the group consisting of aryl as defined above, C$_3$-C$_7$-cycloalkyl, halo (Cl, Br, I, F) —OH, —NH$_2$, —NH(C$_1$-C$_4$-alkyl), —CF$_2$CF$_3$, —N(C$_1$-C$_4$-alkyl)$_2$, —NH—SO$_2$R$^4$, —COOR$^4$, —CF$_3$, —CF$_2$CH$_3$, —SO$_2$NHR$^9$; or
(c) an unsubstituted, monosubstituted or disubstituted aromatic 5 or 6 membered cyclic ring which can contain one or two members selected from the group consisting of N, O, S, and wherein the substituents are members selected from the group consisting of —OH, —SH, C$_1$-C$_4$-alkyl, C$_1$-C$_4$-alkyloxy, —CF$_3$, halo (Cl, Br, I, F), or NO$_2$,
(d) perfluoro-C$_1$-C$_4$-alkyl,
(e) C$_3$-C$_7$-cycloalkyl optionally mono- or disubstituted with C$_1$-C$_4$-alkyl or —CF$_3$;

R$^9$ is H, C$_1$-C$_5$-alkyl, aryl or —CH$_2$-aryl where aryl is as defined above;
R$^{10}$ is H, C$_1$-C$_4$-alkyl;
R$^{11}$ is H, C$_1$-C$_6$-alkyl, C$_2$-C$_4$-alkenyl, C$_1$-C$_4$-alkoxy-C$_1$-C$_4$-alkyl, or

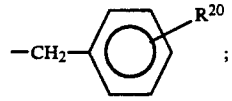

R$^{12}$ is —CN, —NO$_2$ or —CO$_2$R$^4$;
R$^{13}$ is H, —CO(C$_1$-C$_4$-alkyl), C$_1$-C$_6$-alkyl, allyl, C$_3$-C$_6$-cycloalkyl, phenyl or benzyl;
R$^{14}$ is H, C$_1$-C$_8$-alkyl, C$_1$-C$_8$-perfluoroalkyl, C$_3$-C$_6$-cycloalkyl, phenyl or benzyl;
R$^{15}$ is H, C$_1$-C$_6$-alkyl;

$R^{16}$ is H, $C_1$-$C_6$-alkyl, $C_3$-$C_6$-cycloalkyl, phenyl or benzyl;

$R^{17}$ is —$NR^9R^{10}$, —$OR^{10}$, —$NHCONH_2$, —$NHCSNH_2$,

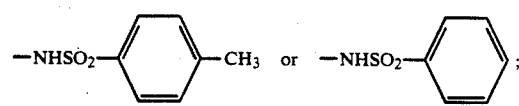

$R^{18}$ and $R^{19}$ are independently $C_1$-$C_4$-alkyl or taken together are —$(CH_2)_q$— where q is 2 or 3;

$R^{20}$ is H, —$NO_2$, —$NH_2$, —OH or —$OCH_3$;

$R^{23}$ is
  (a) aryl as defined above,
  (b) heteroaryl as defined above,
  (c) $C_3$-$C_4$-cycloalkyl,
  (d) $C_1$-$C_4$-alkyl which can be optionally substituted with a substituent that is a member selected from the group consisting of aryl as defined above, heteroaryl as defined above, —OH, —SH, —$C_1$-$C_4$-alkyl, —O($C_1$-$C_4$-alkyl), —S($C_1$-$C_4$-alkyl), —$CF_3$, halo(Cl, Br, F, I), —$NO_2$, —$CO_2H$, —$CO_2$—$C_1$-$C_4$-alkyl, —$NH_2$, —NH($C_1$-$C_4$-alkyl), —$NHCOR^{4a}$, —N($C_1$-$C_4$-alkyl)$_2$, —$PO_3H$, —PO(OH)($C_1$-$C_4$-alkyl), —PO(OH)(aryl), or —PO(OH)(O—$C_1$-$C_4$-alkyl),
  (e) perfluoro-$C_1$-$C_4$-alkyl;

X is absent or is
  (a) a carbon-carbon single bond,
  (b) —CO—,
  (c) —O—,
  (d) —S—,
  (e)
  (f)

  (g)

(h) —$OCH_2$—,
  (i) —$CH_2O$—
  (j) —$SCH_2$—,
  (k) —$CH_2S$—,
  (l) —$NHC(R^9)(R^{10})$,
  (m) —$NR^9SO_2$—,
  (n) —$SO_2NR^9$—,
  (o) —$C(R^9)(R^{10})NH$—,
  (p) —CH=CH—,
  (q) —CF=CF—,
  (r) —CH=CF—,
  (s) —CF=CH—,
  (t) —$CH_2CH_2$—,
  (u) —$CF_2CF_2$—,
  (v)

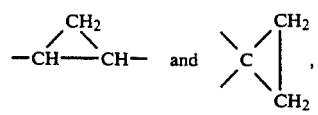

(w)

(x)

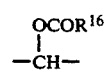

(y)

or
  (z)

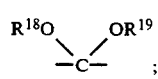

Z is O, $NR^{13}$ or S;

—A—B—C—D— represents the constituent atoms of a 6-member saturated or unsaturated heterocyclic ring with the imidazole to which they are attached containing 1 to 3 nitrogen atoms and includes the following:

1) 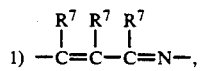

2) 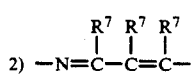

3) 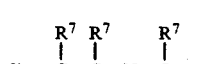

4) 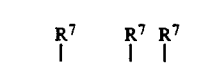

5) 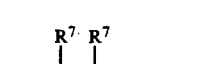

6) 

7) 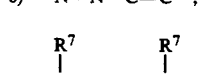

8) 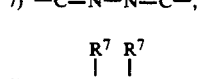

9) 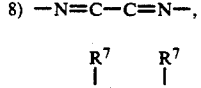

10) 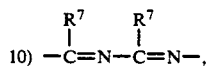

11) 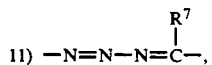

12) 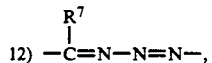

13) 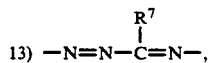

14) 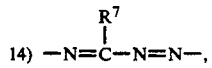

15) 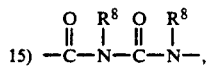

16) 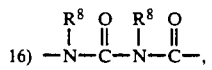

17) 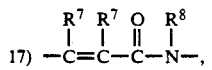

18) 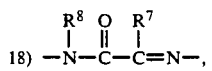

19) 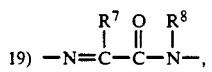

20) 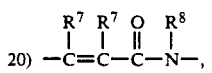

21) 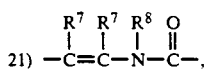

22) 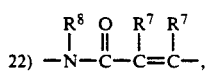

23) 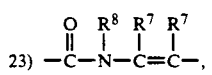

24) 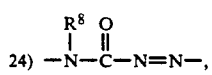

25) 

26) 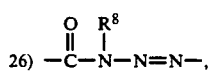

27) 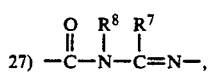

28) 

29) 

30) 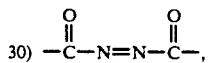

31) 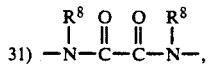

32) 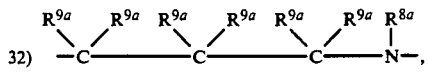

33) 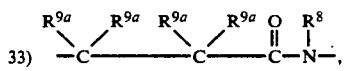

34) 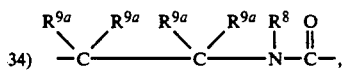

35) 

36) 

37) 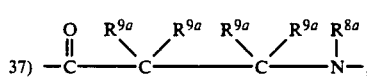

38) 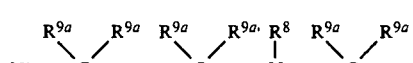

wherein:
$R^7$ groups can be the same or different and represent:
a) hydrogen,
b) $C_1$-$C_6$ straight or branched chain alkyl, or $C_2$-$C_6$ alkenyl, or alkynyl each of which is unsubstituted or substituted with:
i) —OH
ii) $C_1$-$C_4$-alkoxy,
iii) —$CO_2R^4$,
iv) —$OCOR^4$,
v)

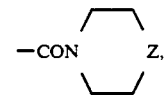

vi) —$CON(R^4)_2$
vii)

viii) —$N(R^4)_2$,
ix) aryl as defined above,
x) heterocyclic as defined in (o) below,
xi) —$S(O)_xR^{23}$,
xii) tetrazol-5-yl,
xiii) —$CONHSO_2R^{23}$,
xiv) —$SO_2NH$-heteroaryl,
xv) —$SO_2NHCOR^{23}$,
xvi)

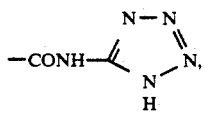

xvii)

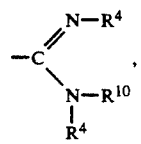

xviii)

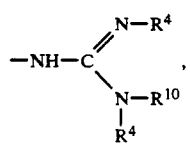

xix) —PO(OR⁴)₂,
xx) —PO(OR⁴)R⁹,
c) halo, such as chloro, bromo or iodo,
d) perfluoro-$C_1$-$C_4$-alkyl,
e) —OH,
f) —NH₂,
g)

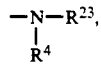

h)

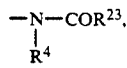

i) —OR²³,
j) —CO₂R⁴,
k) —CON(R⁴)₂,
l) —NH—$C_3$-$C_7$-cycloalkyl,
m) $C_3$-$C_7$-cycloalkyl,
n) aryl as defined above, or
o) heterocyclic which is a five- or six- membered saturated or unsaturated ring containing up to three heteroatoms selected from the group consisting of O, N or S wherein S may in the form of sulfoxide or sulfone and which may be optionally substituted with one or two substituents which are members selected from the group consisting of halo (Cl, Br; F, I), $C_1$-$C_4$-alkyl, $C_1$-$C_4$-alkoxy, $C_1$-$C_4$—S(O)$_x$—where x is as defined above, CF₃, NO₂, OH, CO₂H, CO₂—$C_1$-$C_4$-alkyl, or —N(R⁴)₂;
p) —CN,
q)

wherein n is 4 to 6,
r) —SO₂N(R⁴)₂;

s) tetrazol-5-yl,
t) —CONHSO₂R²³,
u) —PO(OR⁴)₂,
v) —NHSO₂CF₃,
w) —SO₂NH-heteroaryl,
x) —SO₂NHCOR²³,
y) —S(O)$_x$-R²³,
z)

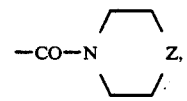

aa) —PO(OR⁴)R⁹,
bb) —NHSO₂R²³,
cc) —NHSO₂NHR²³,
dd) —NHSO₂NHCOR²³,
ee) —NHCONHSO₂R²³,
ff) —N(R⁴)CO₂R²³,
gg)

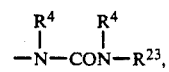

hh) —CO—aryl,
ii)

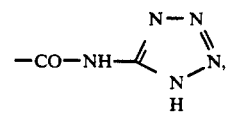

jj) —CO—$C_1$-$C_4$-alkyl,
kk) —SO₂NH—CN,
ll)

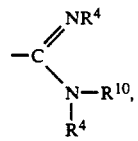

mm)

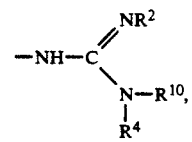

R⁸ groups can be the same or different and represent:
a) hydrogen,
b) $C_1$-$C_6$-alkyl or alkenyl either unsubstituted or substituted with hydroxy, $C_1$-$C_4$-alkoxy, —N(R⁴)₂, —CO₂R⁴, or $C_3$-$C_5$-cycloalkyl;
c) $C_3$-$C_5$-cycloalkyl,
R⁸ᵃ is R⁸ or $C_1$-$C_4$-acyl;
R⁹ᵃ groups can be the same or different and represent:
a) hydrogen,
b) $C_1$-$C_6$-alkyl either unsubstituted or substituted with
i) hydroxy,
ii) —CO₂R⁴, iii) —CONHR$^4$, or iv) —CON(R$^4$)$_2$; and, the pharmaceutically acceptable salts thereof.

One embodiment of the novel compounds of this invention is the class compounds of Formula I wherein:

R$^1$ is:
a) —CO$_2$R$^4$
b) —NHSO$_2$CF$_3$
c)

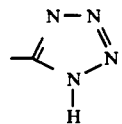

d)

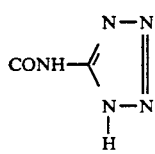

(e) —SO$_2$NH-heteroaryl,
(f) —CH$_2$SO$_2$NH-heteroaryl,
(g) —SO$_2$NHCOR$^{23}$,
(h) —CH$_2$SO$_2$NHCOR$^{23}$,
(i) —CONHSO$_2$R$^{23}$,
(j) —CH$_2$CONHSO$_2$R$^{23}$,
(k) —NHSO$_2$NHCOR$^{23}$, or
(l) —NHCONHSO$_2$R$^{23}$,
(m) —SO$_2$NHCONHR$^{23}$, wherein heteroaryl is as first defined above;

X is a single bond;

R$^{2a}$ and R$^{2b}$ are independently:
a) C$_1$-C$_4$-alkyl,
b) halogen,
c) hydrogen;

R$^{3a}$ and R$^{3b}$ are independently:
a) C$_1$-C$_6$-alkyl,
b) halogen, or
c) C$_1$-C$_6$-alkoxy,
d) hydrogen;

R$^4$ is H, or C$_1$-C$_4$-alkyl;

E is a single bond or —S—;

R$^6$ is a branched or straight chain C$_1$-C$_6$-alkyl, C$_3$-C$_7$-cycloalkyl, C$_2$-C$_6$-alkenyl or C$_2$-C$_6$-alkynyl each of which is either unsubstituted or substituted with C$_1$-C$_4$-alkylthio, C$_1$-C$_4$-alkoxy, CF$_3$, CF$_2$CF$_3$ or —CF$_2$CH$_3$;

and A—B—C—D— represents:

1) 

2) 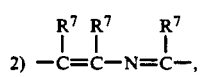

3) 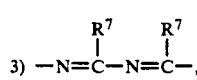

4) 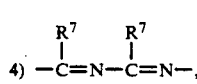

5) 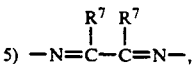

6) 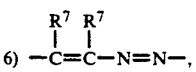

7) 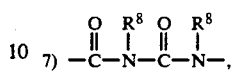

8) 

9) 

10) 

11) 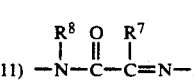

12) 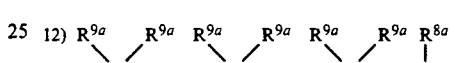

13) 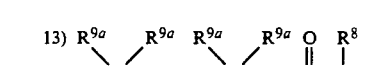

14) 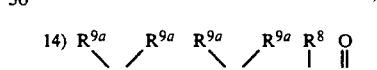

wherein

R$^7$ groups are the same or different and represent:
a) hydrogen,
b) —C$_1$-C$_4$-alkyl, either unsubstituted or substituted with:
i) —OH,
ii) —CO$_2$R$^4$,
iii) —NH$_2$,
iv) (C$_1$-C$_4$ alkyl)amino,
v) di(C$_1$-C$_4$-alkyl)amino,
c) halo,
d) —CF$_3$,
e) —OH,
f) —N(R$^4$)$_2$,
g) —C$_1$-C$_4$-alkoxy,
h) —CO$_2$R$^4$,
i) —CONH$_2$,
j) —C$_3$-C$_7$-cycloalkyl,
k) aryl,
l) heterocyclic as defined above,
m) —CF$_3$,
n) tetrazol-5-yl,
o) —CONHSO$_2$R$^{23}$;

R$^8$ groups are the same or different and represent,
a) hydrogen,
b) C$_1$-C$_4$-alkyl either unsubstituted or substituted with —OH or —CO$_2$R$^4$; and R$^{8a}$ represents
a) hydrogen,
b) C$_1$-C$_4$ alkyl, or
c) (C$_1$-C$_4$-alkyl)CO—; and R$^{9a}$ groups are the same or different and represent:
a) hydrogen,
b) C$_1$-C$_4$-alkyl.

Another embodiment of this invention is the group of compounds of Formula I wherein:

$R^1$ is:
a) —$CO_2R^4$,
b) —$SO_2NH$-heteroaryl,
c) —$CH_2SO_2NH$-heteroaryl,
d) —$SO_2NHCOR^{23}$,
e) —$CH_2SO_2NHCOR^{23}$,
f) —$CONHSO_2R^{23}$,
g) —$CH_2CONHSO_2R^{23}$,
h) —$NHSO_2NHCOR^{23}$,
i) —$NHCONHSO_2R^{23}$,
j) —$SO_2NHCONHR^{23}$,
k)

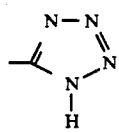

or
l) —$NHSO_2CF_3$,
wherein heteroaryl is as first defined above;
$R^{2a}$ and $R^{2b}$ are independently:
a) $C_1$-$C_4$-alkyl, or
b) chloro,
c) hydrogen;
$R^{3a}$ and $R^{3b}$ are independently:
a) $C_1$-$C_4$-alkyl,
b) chloro, or
c) $C_1$-$C_4$-alkoxy,
d) hydrogen;
E is a single bond or —S—;
$R^6$ is
(a) a branched or straight chain $C_1$-$C_6$-alkyl, $C_2$-$C_6$-alkenyl or $C_2$-$C_6$-alkynyl each of which is either unsubstituted or substituted with $C_1$-$C_4$-alkylthio, $C_1$-$C_4$-alkoxy, $CF_3$, $CF_2CF_3$ or —$CF_2CH_3$;
(b) $C_3$-$C_7$-cycloalkyl;
(c) perfluoro-$C_1$-$C_4$-alkyl;
A—B—C—D— represents:

1) 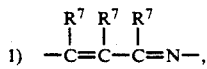

2) 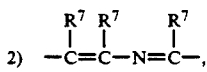

3) 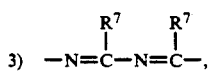

4) 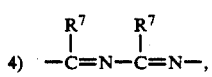

5) 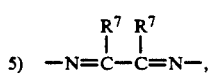

6) 

7) 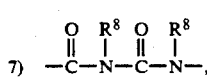

8) 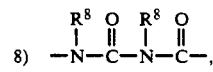

9) 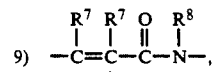

10) 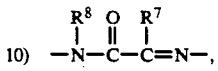

11) 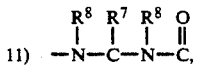

12) 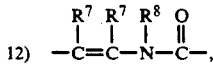

wherein
$R^7$ groups are the same or different and represent:
a) hydrogen,
b) —$C_1$-$C_4$-alkyl, either unsubstituted or substituted with —OH or —$CO_2R^4$,
c) halo,
d) —OH,
e) —$N(R^4)_2$,
f) —$C_1$-$C_4$-alkoxy, or
g) —$CO_2R^4$,
h) aryl,
i) heterocyclic as defined above,
j) —$CF_3$,
k) tetrazol-5-yl,
$R^8$ groups are the same or different and represent:
a) H,
b) $C_1$-$C_4$-alkyl either unsubstituted or substituted with —OH or —$CO_2R^4$.

In a class of this embodiment are those compounds of Formula I wherein:

$R^1$ is
a) —$CO_2R^4$
b)

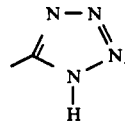

c) —$NHSO_2CF_3$,
d) —$SO_2NH$-heteroaryl,
e) —$CH_2SO_2NH$-heteroaryl,
f) —$SO_2NHCOR^{23}$,
g) —$CH_2SO_2NHCOR^{23}$,
h) —$CONHSO_2R^{23}$,
i) —$CH_2CONHSO_2R^{23}$;
E is a single bond;
A—B—C—D represents:

1) 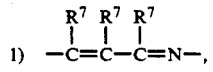

2) 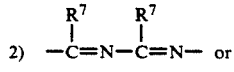 or

3) 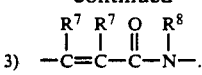

Exemplifying this class are the following compounds:
(1) 2-Butyl-3-(2'-carboxybiphen-4-yl)methyl-3H-imidazo[4,5-b]pyridine;
(2) 3-(2'-Carboxybiphen-4-yl)methyl-2-propyl-3H-imidazo[4,5-b]pyridine;
(3) 3-(2'-Carboxybiphen-4-yl)methyl-2-ethyl-3H-imidazo[4,5-b]pyridine;
(4) 3-(2'-Carboxybiphen-4-yl)methyl-2-isopropyl-3H-imidazo[4,5-b]pyridine;
(5) 3-(2'-Carboxybiphen-4-yl)methyl-2-cyclopropyl-3H-imidazo[4,5-b]pyridine;
(6) 3-(2'-Carboxybiphen-4-yl)methyl-7-methyl-2-propyl-3H-imidazo[4,5-b]pyridine;
(7) 3-(2'-Carboxybiphen-4-yl)methyl-7-ethyl-2-propyl-3H-imidazo[4,5-b]pyridine;
(8) 3-(2'-Carboxybiphen-4-yl)methyl-2-ethyl-7-methyl-3H-imidazo[4,5-b]pyridine;
(9) 3-(2'-Carboxybiphen-4-yl)methyl-2,7-diethyl-3H-imidazo[4,5-b]pyridine;
(10) 3-(2'-Carboxybiphen-4-yl)methyl-5,7-dimethyl-2-propyl-3H-imidazo[4,5-b]pyridine;
(11) 3-(2'-Carboxybiphen-4-yl)methyl-5,7-dimethyl-2-ethyl-3H-imidazo[4,5-b]pyridine;
(12) 3-(2'-Carboxybiphen-4-yl)methyl-2-cyclopropyl-5,7-dimethyl-3H-imidazo[4,5-b]pyridine;
(13) 3-(2'-Carboxybiphen-4-yl)methyl-5-ethyl-7-methyl-2-propyl-3H-imidazo[4,5-b]pyridine;
(14) 3-(2'-Carboxybiphen-4-yl)methyl-2,5-diethyl-7-methyl-3H-imidazo[4,5-b]pyridine;
(15) 3-(2'-Carboxybiphen-4-yl)methyl-2-ethyl-7-methyl-5-methylamino-3H-imidazo[4,5-b]pyridine;
(16) 5-Amino-3-(2'-carboxybiphen-4-yl)methyl-2-ethyl-7-methyl-3H-imidazo[4,5-b]pyridine;
(17) 3-(2'-Carboxybiphen-4-yl)methyl-2-ethyl-5-methylamino-7-trifluoromethyl-3H-imidazo[4,5-b]pyridine;
(18) 3-(2'-Carboxybiphen-4-yl)methyl-2-ethyl-5-methyl-7-methylamino-3H-imidazo[4,5-b]pyridine;
(19) 3-(2'-Carboxybiphen-4-yl)methyl-7-dimethylamino-2-ethyl-5-methyl-3H-imidazo[4,5-b]pyridine;
(20) 3-(2'-Carboxybiphen-4-yl)methyl-2-ethyl-5-methyl-7-phenylamino-3H-imidazo[4,5-b]pyridine;
(21) 3-(2'-Carboxybiphen-4-yl)methyl-2-ethyl-5-methyl-7-(morpholin-4-yl)-3H-imidazo[4,5-b]pyridine;
(22) 3-(2'-Carboxybiphen-4-yl)methyl-2-ethyl-7-methyl-5-(morpholin-4-yl)-3H-imidazo[4,5-b]pyridine;
(23) 3-(2'-Carboxybiphen-4-yl)methyl-2-ethyl-7-methoxy-5-methyl-3H-imidazo[4,5-b]pyridine;
(24) 3-(2'-Carboxybiphen-4-yl)methyl-2-ethyl-5-hydroxymethyl-7-methyl-3H-imidazo[4,5-b]pyridine;
(25) 5-Carboxy-3-(2'-carboxybiphen-4-yl)methyl-2-ethyl-7-methyl-3H-imidazo[4,5-b]pyridine;
(26) 5-Carbomethoxy-3-(2'-carboxybiphen-4-yl)methyl-2-ethyl-7-methyl-3H-imidazo[4,5-b]pyridine;
(27) 3-(2'-Carboxybiphen-4-yl)methyl-2-ethyl-7-methyl-5-phenyl-3H-imidazo[4,5-b]pyridine;
(28) 3-(2'-Carboxybiphen-4-yl)methyl-5-(2-chloro)phenyl-2-ethyl-7-methyl-3H-imidazo[4,5-b]pyridine;
(29) 3-(2'-Carboxybiphen-4-yl)methyl-5-(4-chloro)phenyl-2-ethyl-7-methyl-3H-imidazo[4,5-b]pyridine;
(30) 3-(2'-Carboxybiphen-4-yl)methyl-2-ethyl-7-methyl-5-(2-trifluoromethyl)phenyl-3H-imidazo[4,5-b]pyridine;
(31) 6-Amino-3-(2'-carboxybiphen-4-yl)methyl-5,7-dimethyl-2-ethyl-3H-imidazo[4,5-b]pyridine;
(32) 3-(2'-Carboxybiphen-4-yl)methyl-5,7-dimethyl-2-ethyl-6-ethylamino-3H-imidazo[4,5-b]pyridine;
(33) 3-(2'-Carboxybiphen-4-yl)methyl-5,7-dimethyl-2-ethyl-6-fluoro-3H-imidazo[4,5-b]pyridine;
(34) 3-(2'-Carboxybiphen-4-yl)methyl-5,7-dimethyl-2-(2,2,2,-trifluoro)ethyl-3H-imidazo[4,5-b]pyridine;
(35) 3-(2'-Carboxybiphen-4-yl)methyl-5,7-dimethyl-2-pentafluoroethyl-3H-imidazo[4,5-b]pyridine;
(36) 3-(2'-Carboxybiphen-4-yl)methyl-5,7-dimethyl-2-(3,3,3,-trifluoro)propyl-3H-imidazo[4,5-b]pyridine;
(37) 3-(2'-Carboxybiphen-4-yl)methyl-5,7-dimethyl-2-(4,4,4,-trifluoro)butyl-3H-imidazo[4,5-b]pyridine;
(38) 3-(2'-Carboxybiphen-4-yl)methyl-5,7-dimethyl-2-(2,2,-difluoro)propyl-3H-imidazo[4,5-b]pyridine;
(39) 3-(2'-Carboxybiphen-4-yl)methyl-5,7-dimethyl-2-(trans-2-butenyl)-3H-imidazo[4,5-b]pyridine;
(40) 3-(2'-Carboxybiphen-4-yl)methyl-5,7-dimethyl-2-(trans-1-propenyl)-3H-imidazo[4,5-b]pyridine;
(41) 2-Allyl-3-(2'-carboxybiphen-4-yl)methyl-5,7-dimethyl-3H-imidazo[4,5-b]pyridine;
(42) 3-(2'-Carboxybiphen-4-yl)methyl-5,7-dimethyl-2-(2-propynyl)-3H-imidazo[4,5-b]pyridine;
(43) 2-(2-Butynyl)-3-(2'-carboxybiphen-4-yl)methyl-5,7-dimethyl-3H-imidazo[4,5-b]pyridine;
(44) 3-(2'-Carboxybiphen-4-yl)methyl-5,7-dimethyl-2-(4,4,4-trifluoro-2-butynyl)-3H-imidazo[4,5-b]pyridine;
(45) 3-(2'-Carboxybiphen-4-yl)methyl-5,7-dimethyl-2-(2,2,2-trifluro)ethoxy-3H-imidazo[4,5-b]pyridine;
(46) 2-Butyl-3-(2'-(tetrazol-5-yl)biphen-4-yl)-methyl-3H-imidazo[4,5-b]pyridine;
(47) 2-Propyl-3-(2'-(tetrazol-5-yl)biphen-4-yl)methyl-3H-imidazo[4,5-b]pyridine;
(48) 2-Ethyl-3-(2'-(tetrazol-5-yl)biphen-4-yl)methyl-3H-imidazo[4,5-b]pyridine;
(49) 2-Isopropyl-7-methyl-3-(2'-(tetrazol-5-yl)biphen-4-yl)methyl-3H-imidazo[4,5-b]pyridine;
(50) 2-Cyclopropyl-7-methyl-3-(2'-(tetrazol-5-yl)biphen-4-yl)methyl-3H-imidazo[4,5-b]pyridine;
(51) 2-Butyl-7-methyl-3-(2'-(tetrazol-5-yl)biphen-4-yl)methyl-3H-imidazo[4,5-b]pyridine;
(52) 7-Methyl-2-(3-methyl)propyl-3-(2'-(tetrazol-5-yl)biphen-4-yl)methyl-3H-imidazo[4,5-b]pyridine;
(53) 2-Methoxymethyl-7-methyl-3-(2'-(tetrazol-5-yl)biphen-4-yl)methyl-3H-imidazo[4,5-b]pyridine;
(54) 7-Methyl-2-propyl-3-(2'-(tetrazol-5-yl)biphen-4-yl)methyl-3H-imidazo[4,5-b]pyridine;
(55) 7-Ethyl-2-propyl-3-(2'-(tetrazol-5-yl)biphen-4-yl)methyl-3H-imidazo[4,5-b]pyridine;
(56) 2-Ethyl-7-methyl-3-(2'-(tetrazol-5-yl)biphen-4-yl)methyl-3H-imidazo[4,5-b]pyridine;
(57) 2,7-Diethyl-3-(2'-(tetrazol-5-yl)biphen-4-yl)methyl-3H-imidazo[4,5-b]pyridine;
(58) 2-Butyl-5,7-dimethyl-3-(2'-(tetrazol-5-yl)biphen-4-yl)methyl-3H-imidazo[4,5-b]pyridine;
(59) 5,7-Dimethyl-2-propyl-3-(2'-(tetrazol-5-yl)biphen-4-yl)methyl-3H-imidazo[4,5-b]pyridine;
(60) 5,7-Dimethyl-2-ethyl-3-(2'-(tetrazol-5-yl)biphen-4-yl)methyl-3H-imidazo[4,5-b]pyridine;
(61) 2-Cyclopropyl-5,7-dimethyl-3-(2'-(tetrazol-5-yl)biphen-4-yl)methyl-3H-imidazo[4,5-b]pyridine;
(62) 5-Ethyl-7-methyl-2-propyl-3-(2'-(tetrazol-5-yl)biphen-4-yl)methyl-3H-imidazo[4,5-b]pyridine;

(63) 2,5-Diethyl-7-methyl-3-(2'-(tetrazol-5-yl)biphen-4-yl)methyl-3H-imidazo[4,5-b]pyridine;
(64) 2,7-Dimethyl-3-(2'-(tetrazol-5-yl)biphen-4-yl)methyl-3H-imidazo[4,5-b]pyridine;
(65) 7-Methyl-2-pentyl-3-(2'-(tetrazol-5-yl)biphen-4-yl)methyl-3H-imidazo[4,5-b]pyridine;
(66) 7-Methyl-2-nonyl-3-(2'-(tetrazol-5-yl)biphen-4-yl)methyl-3H-imidazo[4,5-b]pyridine;
(67) 2-Ethyl-7-methyl-5-methylamino-3-(2'-(tetrazol-5-yl)biphen-4-yl)methyl-3H-imidazo[4,5-b]pyridine;
(68) 5-Amino-7-methyl-2-ethyl-3-(2'-(tetrazol-5-yl)biphen-4-yl)methyl-3H-imidazo[4,5-b]pyridine;
(69) 5-Amino-2-propyl-3-(2'-(tetrazol-5-yl)biphen-4-yl)methyl-3H-imidazo[4,5-b]pyridine;
(70) 2-Ethyl-5-methylamino-7-trifluoromethyl-3-(2'-(tetrazol-5-yl)biphen-4-yl)methyl-3H-imidazo[4,5-b]pyridine;
(71) 2-Ethyl-5-methyl-7-methylamino-3-(2'-(tetrazol-5-yl)biphen-4-yl)methyl-3H-imidazo[4,5-b]pyridine;
(72) 7-Dimethylamino-2-ethyl-5-methyl-3-(2'-(tetrazol-5-yl)biphen-4-yl)methyl-3H-imidazo[4,5-b]pyridine;
(73) 2-Ethyl-5-methyl-7-phenylamino-3-(2'-(tetrazol-5-yl)biphen-4-yl)methyl-3H-imidazo[4,5-b]pyridine;
(74) 2-Ethyl-5-methyl-7-(morpholin-4-yl)-3-(2'-(tetrazol-5-yl)biphen-4-yl)methyl-3H-imidazo[4,5-b]pyridine;
(75) 2-Ethyl-7-methyl-5-(morpholin-4-yl)-3-(2'-(tetrazol-5-yl)biphen-4-yl)methyl-3H-imidazo[4,5-b]pyridine;
(76) 5-Amino-2-ethyl-3-(2'-(tetrazol-5-yl)biphen-4-yl)methyl-7-trifluoromethyl-3H-imidazo[4,5-b]pyridine;
(77) 2-Ethyl-7-methoxy-5-methyl-3-(2'-(tetrazol-5-yl)biphen-4-yl)methyl-3H-imidazo[4,5-b]pyridine;
(78) 2-Ethyl-5-hydroxymethyl-7-methyl-3-(2'-(tetrazol-5-yl)biphen-4-yl)methyl-3H-imidazo[4,5-b]pyridine;
(79) 5-Carboxy-2-ethyl-7-methyl-3-(2'-(tetrazol-5-yl)biphen-4-yl)methyl-3H-imidazo[4,5-b]pyridine;
(80) 5-Carbomethoxy-2-ethyl-7-methyl-3-(2'-(tetrazol-5-yl)biphen-4-yl)methyl-3H-imidazo[4,5-b]pyridine;
(81) 2-Ethyl-7-methyl-5-phenyl-3-(2'-(tetrazol-5-yl)biphen-4-yl)methyl-3H-imidazo[4,5-b]pyridine;
(82) 5-(2-Chloro)phenyl-2-ethyl-7-methyl-3-(2'-(tetrazol-5-yl)biphen-4-yl)methyl-3H-imidazo[4,5-b]pyridine;
(83) 5-(4-Chloro)phenyl-2-ethyl-7-methyl-3-(2'-(tetrazol-5-yl)biphen-4-yl)methyl-3H-imidazo[4,5-b]pyridine;
(84) 2-Ethyl-7-methyl-5-(2-trifluoromethyl)phenyl-3-(2'-(tetrazol-5-yl)biphen-4-yl)methyl-3H-imidazo[4,5b]pyridine;
(85) 6-Amino-5,7-dimethyl-2-ethyl-3-(2'-(tetrazol-5-yl)biphen-4-yl)methyl-3H-imidazo[4,5-b]pyridine;
(86) 5,7-Dimethyl-2-ethyl-6-ethylamino-3-(2'-(tetrazol-5-yl)biphen-4-yl)methyl-3H-imidazo[4,5-b]pyridine;
(87) 5,7-Dimethyl-2-ethyl-6-fluoro-3-(2'-(tetrazol-5-yl)biphen-4-yl)methyl-3H-imidazo[4,5-b]pyridine;
(88) 5,7-Dimethyl-3-(2'-(tetrazol-5-yl)biphen-4-yl)methyl-2-(2,2,2,-trifluoro)ethyl-3H-imidazo[4,5-b]pyridine;
(89) 5,7-Dimethyl-2-pentafluoroethyl-3-(2'-(tetrazol-5-yl)biphen-4-yl)methyl-3H-imidazo[4,5-b]pyridine;
(90) 5,7-Dimethyl-3-(2'-(tetrazol-5-yl)biphen-4-yl)methyl-2-(3,3,3,-trifluoro)propyl-3H-imidazo[4,5-b]pyridine;
(91) 5,7-Dimethyl-3-(2'-(tetrazol-5-yl)biphen-4-yl)methyl-2-(4,4,4,-trifluoro)butyl-3H-imidazo[4,5-b]pyridine;
(92) 5,7-Dimethyl-2-(2,2,-difluoro)propyl-3-(2'-(tetrazol-5-yl)biphen-4-yl)methyl-3H-imidazo[4,5-b]pyridine;
(93) 5,7-Dimethyl-2-(trans-2-butenyl)-3-(2'-(tetrazol-5-yl)biphen-4-yl)methyl-3H-imidazo[4,5-b]pyridine;
(94) 5,7-Dimethyl-3-(2'-(tetrazol-5-yl)biphen-4-yl)methyl-2-(trans-1-propenyl)-3H-imidazo[4,5-b]pyridine;
(95) 2-Allyl-5,7-dimethyl-3-(2'-(tetrazol-5-yl)biphen-4-yl)methyl-3H-imidazo[4,5-b]pyridine;
(96) 5,7-Dimethyl-2-(2-propynyl)-3-(2'-(tetrazol-5-yl)biphen-4-yl)methyl-3H-imidazo[4,5-b]pyridine;
(97) 2-(2-Butynyl)-5,7-dimethyl-3-(2'-(tetrazol-5-yl)biphen-4-yl)methyl-3H-imidazo[4,5-b]pyridine;
(98) 5,7-Dimethyl-3-(2'-(tetrazol-5-yl)biphen-4-yl)methyl-2-(4,4,4-trifluoro-2-butynyl)-3H-imidazo[4,5-b]pyridine;
(99) 5,7-Dimethyl-3-(2'-(tetrazol-5-yl)biphen-4-yl)methyl-2-(2,2,2-trifluoroethoxy)-3H-imidazo[4,5-b]pyridine;
(100) 5,7-Dimethyl-2-ethyl-3-(2'-(N-((phenylsulfonyl)carboxamido)biphen-4-yl)methyl-3H-imidazo[4,5-b]pyridine;
(101) 5,7-Dimethyl-2-ethyl-3(2'-(N-(2-bromophenylsulfonyl)carboxamido)biphen-4-yl)methyl-3H-imidazo[4,5-b]pyridine;
(102) 3-(2'-(N-(4-Chlorophenylsulfonyl)carboxamido)biphen-4-yl)methyl-7-methyl-2-propyl-3H-imidazo[4,5-b]pyridine;
(103) 3-(2'-(N-Methylsulfonylcarboxamido)biphen-4-yl)methyl-7-methyl-2-propyl-3H-imidazo[4,5-b]pyridine;
(104) 5,7-Dimethyl-2-ethyl-3-(2'-(N-methylsulfonyl)carboxamidobiphen-4-yl)methyl-3H-imidazo[4,5-b]pyridine;
(105) 5,7-Dimethyl-2-ethyl-3-(2'-(N-trifluoromethylsulfonyl)carboxamidobiphen-4-yl)methyl-3H-imidazo-[4,5-b]pyridine;
(106) 3-(2'-(N-(2-Aminoethyl)sulfonyl)carboxamidobiphen-4-yl)methyl-5,7-dimethyl-2-ethyl-3H-imidazo[4,5-b]pyridine;
(107) 5,7-Dimethyl-2-ethyl-3-(2'-(N-(morpholin-4-yl)sulfonyl)carboxamidobiphen-4-yl)methyl-3H-imidazo[4,5-b]pyridine;
(108) 5,7-Dimethyl-(2'-(N-(N,N-dimethylamino)sulfonyl)carboxamidobiphen-4-yl)methyl-2-ethyl-3H-imidazo[4,5-b]pyridine;
(109) 3-(2'-(N-Cyclopentylsulfonyl)carboxamidobiphen-4-yl)methyl-5,7-dimethyl-2-ethyl-3H-imidazo[4,5-b]pyridine;
(110) 5,7-Dimethyl-2-ethyl-3-(2'-(N-pyrimidin-2-yl)sulfonamidobiphen-4-yl)methyl-3H-imidazo-[4,5-b]pyridine;
(111) 5,7-Dimethyl-3-(2'-(N-(4,6-dimethylpyrimidin-2-yl)sulfonamido)biphen-4-yl)methyl-2-ethyl-3H-imidazo[4,5-b]pyridine;
(112) 5,7-Dimethyl-2-ethyl-3-(2'-(N-(triazin-2-yl)sulfonamido)biphen-4-yl)methyl-3H-imidazo[4,5-b]pyridine;
(113) 5,7-Dimethyl-2-ethyl-3-(2'-(N-(oxazol-2-yl)sulfonamido)biphen-4-yl)methyl-3H-imidazo[4,5-b]pyridine;
(114) 3-(2'-(N-Acetyl)sulfonamidobiphen-4-yl)methyl-5,7-dimethyl-2-ethyl-3H-imidazo[4,5-b]pyridine;
(115) 3-(2'-(N-Benzoyl)sulfonamidobiphen-4-yl)methyl-5,7-dimethyl-2-ethyl-3H-imidazo[4,5-b]pyridine;
(116) 5,7-Dimethyl-2-ethyl-3-(2'-(N-(4-nitro)benzoyl)sulfonamidobiphen-4-yl)methyl-3H-imidazo[4,5-b]pyridine;

(117) 3-(2'-(N-(4-Chloro)benzoyl)sulfonamidobiphen-4-yl)methyl-5,7-dimethyl-2-ethyl-3H-imidazo[4,5-b]pyridine;
(118) 5,7-Dimethyl-2-ethyl-3-(2'-(N-(morpholin-4-yl)carbonyl)sulfonamidobiphen-4-yl)methyl-3H-imidazo[4,5-b]pyridine;
(119) 5,7-Dimethyl-2-ethyl-3-(2'-(N-(piperazin-1-yl)carbonyl)sulfonamidobiphen-4-yl)methyl-3H-imidazo[4,5-b]pyridine;
(120) 5,7-Dimethyl-2-ethyl-3-(2'-(N-(trifluoromethyl)-carbonyl)sulfonamidobiphen-4-yl)methyl-3H-imidazo[4,5-b]pyridine;
(121) 3-(2'-(N-(2-Carboxyethyl)carbonyl)sulfonamidobiphen-4-yl)methyl-5,7-dimethyl-2-ethyl-3H-imidazo[4,5-b]pyridine;
(122) 5,7-Dimethyl-3-(2'-(N-(2'-ethoxyethyl)carbonyl)-sulfonamidobiphen-4-yl)methyl-2-ethyl-3H-imidazo[4,5-b]pyridine;
(123) 5,7-Dimethyl-2-ethyl-3-(2'-(N-(phenylsulfonyl)-carboxamidomethyl)biphen-4-yl)methyl-3H-imidazo[4,5-b]pyridine;
(124) 5,7-Dimethyl-3-(2'-N-(4,6-dimethylpyrimidin-2-yl)sulfamidomethyl)biphen-4-yl)methyl-2-ethyl-3H-imidazo[4,5-b]pyridine;
(125) 7-Methyl-3-(2'-(N-phenylsulfonyl)carboxamidobiphen-4-yl)methyl-2-propyl-3H-imidazo[4,5-b]pyridine;
(126) 3-(2'-((N-Acetyl)sulfonamidomethyl)biphen-4-yl)methyl-7-methyl-2-propyl-3H-imidazo[4,5-b]pyridine;
(127) 7-Methyl-2-propyl-3-((2'-trifluoromethanesulfonylamino)bipheny-4-yl)methyl-3H-imidazopyridine;
(128) 5,7-Dimethyl-2-ethyl-3-((2'-trifluoromethanesulfonylamino)biphen-4-yl)methyl-3H-imidazopyridine;
(129) 4,7-Dimethyl-2-ethyl-3-(2'-(tetrazol-5-yl)biphen-4-yl)methyl-3H-imidazo[4,5-b]pyrid-5-one;
(130) 2-Ethyl-5-hydroxy-7-methyl-3-(2'-(tetrazol-5-yl)biphen-4-yl)methyl-3H-imidazo[4,5-b]pyridine;
(131) 7-Methyl-2-propyl-3-(2'-(tetrazol-5-yl)biphen-4-yl)methyl-3H-imidazo[4,5-b]pyridine sodium salt;
(132) 7-Methyl-2-propyl-3-(2'-(tetrazol-5-yl)biphen-4-yl)methyl-3H-imidazo[4,5-b]pyridine potassium salt;
(133) 5,7-Dimethyl-2-ethyl-3-(4'-chloro-2'-(tetrazol-5-yl)biphen-4-yl)methyl-3H-imidazo[4,5-b]pyridine;
(134) 5,7-Dimethyl-2-ethyl-3-(4'-fluoro-2'-(tetrazol-5-yl)biphen-4-yl)methyl-3H-imidazo[4,5-b]pyridine;
(135) 5,7-Dimethyl-2-ethyl-3-(4'-amino-2'-(tetrazol-5-yl)biphen-4-yl)methyl-3H-imidazo[4,5-b]pyridine;
(136) 5,7-Dimethyl-2-ethyl-3-(5'-fluoro-2'-(tetrazol-5-yl)biphen-4-yl)methyl-3H-imidazo[4,5-b]pyridine;
(137) 3-(2'-Carboxy-6'-chlorobiphen-4-yl)methyl-5,7-dimethyl-2-ethyl-3H-imidazo[4,5-b]pyridine;
(138) 3-(2'-Carboxy-3'-fluorobiphen-4-yl)methyl-2-ethyl-7-methyl-3H-imidazo[4,5-b]pyridine;
(139) 5,7-Dimethyl-2-ethyl-3-(4'-nitro-2'-(tetrazol-5-yl)biphen-4-yl)methyl-3H-imidazo[4,5-b]pyridine;
(140) 5,7-Dimethyl-2-ethyl-3-(2'-(tetrazol-5-yl)biphen-4-yl)methyl-3H-imidazo[4,5-b]pyridine sodium salt;
(141) 5,7-Dimethyl-2-ethyl-3-(2'-(tetrazol-5-yl)biphen-4-yl)methyl-3H-imidazo[4,5-b]pyridine potassium salt;
(142) 9-(2'-Carboxybiphen-4-yl)methyl-6-chloro-8-propylpurine;
(143) 9-(2'-Carboxybiphen-4-yl)methyl-6-methyl-8-propylpurine;
(144) 9-(2'-Carboxybiphen-4-yl)methyl-6-methyl-8-ethylpurine;
(145) 9-(2'-Carboxybiphen-4-yl)methyl-4,6-dimethyl-8-propylpurine;
(146) 9-(2'-Carboxybiphen-4-yl)methyl-4,6-dimethyl-8-ethylpurine;
(147) 9-(2'-Carboxybiphen-4-yl)methyl-4-dimethylamino-6-methyl-8-ethylpurine;
(148) 9-(2'-Carboxybiphen-4-yl)methyl-4-methylamino-6-methyl-8-ethylpurine;
(149) 9-(2'-Carboxybiphen-4-yl)methyl-4-(morpholin-4-yl)-6-methyl-8-ethylpurine;
(150) 9-(2'-Carboxybiphen-4-yl)methyl-4-ethylamino-6-methyl-8-ethylpurine;
(151) 9-(2'-Carboxybiphen-4-yl)methyl-4-propylamino-6-methyl-8-ethylpurine;
(152) 9-(2'-carboxybiphen-4-yl)methyl-4-methylamino-6-trifluoromethyl-8-ethylpurine;
(153) 9-(2'-Carboxybiphen-4-yl)methyl-4,6-dimethyl-8-(2,2,2-trifluoro)ethylpurine;
(154) 9-(2'-Carboxybiphen-4-yl)methyl-4,6-dimethyl-8-(3,3,3-trifluoro)propylpurine;
(155) 9-(2'-Carboxybiphen-4-yl)methyl-4,6-dimethyl-8-(2,2-difluoro)propylpurine;
(156) 8-Butyl-9-(2'-carboxybiphen-4-yl)methyl-6-chloropurine;
(157) 8-Butyl-9-(2'-carboxybiphen-4-yl)methyl-6-hydroxypurine;
(158) 4-Carboxy-9-(2'-carboxybiphen-4-yl)methyl-6-methyl-8-ethylpurine;
(159) 4-Carbomethoxy-9-(2'-carboxybiphen-4-yl)methyl-6-methyl-8-ethylpurine;
(160) 9-(2'-Carboxybiphen-4-yl)methyl-8-ethyl-4-hydroxymethyl-6-methylpurine;
(161) 6-Chloro-8-propyl-9-(2'-(tetrazol-5-yl)biphen-4-yl)methylpurine;
(162) 6-Methyl-8-propyl-9-(2'-(tetrazol-5-yl)biphen-4-yl)methylpurine;
(163) 8-Ethyl-6-methyl-9-(2'-(tetrazol-5-yl)biphen-4-yl)methylpurine;
(164) 4,6-Dimethyl-8-propyl-9-(2'-(tetrazol-5-yl)biphen-4-yl)methylpurine;
(165) 4,6-Dimethyl-8-ethyl-9-(2'-(tetrazol-5-yl)biphen-4-yl)methylpurine;
(166) 6-Methyl-2-methylamino-8-propyl-9-(2'-(tetrazol-5-yl)biphen-4-yl)methylpurine;
(167) 4-Dimethylamino-8-ethyl-6-methyl-9-(2'-(tetrazol-5-yl)biphen-4-yl)methylpurine;
(168) 8-Ethyl-6-methyl-4-methylamino-9-(2'-(tetrazol-5-yl)biphen-4-yl)methylpurine;
(169) 8-Ethyl-6-methyl-4-(morpholin-4-yl)-9-(2'-(tetrazol-5-yl)biphen-4-yl)methylpurine;
(170) 8-Propyl-9-(2'-(tetrazol-5-yl)biphen-4-yl)methylpurine;
(171) 8-Butyl-6-chloro-9-(2'-(tetrazol-5-yl)biphen-4-yl)methylpurine;
(172) 8-Butyl-9-(2'-(tetrazol-5-yl)biphen-4-yl)methylpurine;
(173) 2-Chloro-6-methyl-8-propyl-9-(2'-(tetrazol-5-yl)biphen-4-yl)methylpurine;
(174) 6-Methyl-2-(morpholin-4-yl)-8-propyl-9-(2'-(tetrazol-5-yl)biphen-4-yl)methylpurine;
(175) 8-Ethyl-4-ethylamino-6-methyl-9-(2'-(tetrazol-5-yl)biphen-4-yl)methylpurine;
(176) 8-Ethyl-6-methyl-4-propylamino-9-(2'-(tetrazol-5-yl)biphen-4-yl)methylpurine;
(177) 8-Ethyl-4-methylamino-6-trifluoromethyl-9-(2'-(tetrazol-5-yl)biphen-4-yl)methylpurine;
(178) 4,6-Dimethyl-8-(2,2,2-trifluoro)ethyl-9-(2'-(tetrazol-5-yl)biphen-4-yl)methylpurine;

(179) 4,6-Dimethyl-8-(3,3,3-trifluoro)propyl-9-(2'-(tetrazol-5-yl)biphen-4-yl)methylpurine;
(180) 8-(2,2-Difluoro)propyl-4,6-dimethyl-9-(2'-(tetrazol-5-yl)biphen-4-yl)methylpurine;
(181) 4-Carboxy-8-ethyl-6-methyl-9-(2'-(tetrazol-5-yl)biphen-4-yl)methylpurine;
(182) 4-Carbomethoxy-8-ethyl-6-methyl-9-(2'-(tetrazol-5-yl)biphen-4-yl)methylpurine;
(183) 8-Ethyl-4-hydroxymethyl-6-methyl-9-(2'-(tetrazol-5-yl)biphen-4-yl)methylpurine and;
(184) 8-Butyl-1,3-dimethyl-7-(2'-(tetrazol-5-yl)biphen-4-yl)methyl-1,2,3,6-tetrahydro-2,6-dioxopurine.

The compounds of Formula (I) can be synthesized using the reactions and techniques described herein below. The reactions are performed in a solvent appropriate to the reagents and materials employed and suitable for the transformation being effected. It is understood by those skilled in the art of organic synthesis that the functionality present on the heterocycle and in the reactants being employed should be consistent with the chemical transformations being conducted. Depending upon the reactions and techniques employed, optimal yields may require changing the order of synthetic steps or use of protecting groups followed by deprotection.

| ABBREVIATIONS USED IN REACTION SCHEMES | |
|---|---|
| Reagents: | |
| NBS | N-bromosuccinimide |
| AIBN | Azo(bis)isobutyronitrile |
| DDQ | Dichlorodicyanoquinone |
| Ac$_2$O | acetic anhydride |
| TEA | triethylamine |
| DMAP | 4-dimethylaminopyridine |
| PPh$_3$ | triphenylphosphine |
| TFA | trifluoroacetic acid |
| TMS-Cl | trimethylsilyl chloride |
| Im | imidazole |
| AcSK | potassium thioacetate |
| p-TsOH | p-toluenesulfonic acid |
| Solvents: | |
| Et$_2$O | diethyl ether |
| DMF | dimethylformamide |
| HOAc (AcOH) | acetic acid |
| EtOAc (EtAc) | ethyl acetate |
| Hex | hexane |
| THF | tetrahydrofuran |
| DMSO | dimethylsulfoxide |
| MeOH | methanol |
| iPrOH | isopropanol |
| DBU | 1,8-diazabicyclo-[5.4.0]undec-7-ene |
| Me$_3$SnCl | trimethylstannyl chloride |
| Others: | |
| rt | room temperature |
| TBDMS | t-butyldimethylsilyl |
| OTf | OSO$_2$CF$_3$ |
| OTs | OSO$_2$-(4-methyl)phenyl |
| OMs | OSO$_2$CH$_3$ |
| Ph | phenyl |
| FAB-MS (FABMS) spectroscopy | Fast atom bombardment mass |
| NOE | Nuclear Overhauser Effect |
| SiO$_2$ | silica gel |
| trityl | triphenylmethyl |

As shown in Reaction Scheme 1, compounds of Formula I can be prepared by carrying out direct alkylation of alkali-metal salts of heterocycles (1) (preparation of heterocycles are described in Reaction Schemes 3-6) using appropriately protected benzyl halide, tosylate (OTs) or mesylate (OMs) derivatives (2). The salt is prepared preferably using MH (where M is lithium, sodium or potassium) in anhydrous dimethylformamide (DMF), or by treating it with a metal alkoxide such as sodium or potassium methoxide, ethoxide or t-butoxide in an appropriate alcohol such as methanol, ethanol or t-butanol as the solvent. The alkylation is generally carried out by dissolving the metal salt of the heterocycle in a dipolar aprotic solvent such as DMF or dimethylsulfoxide (DMSO) and reacting it with the alkylating agent at 20° C. to reflux temperature of the solvent for 1-24 hours.

REACTION SCHEME 1

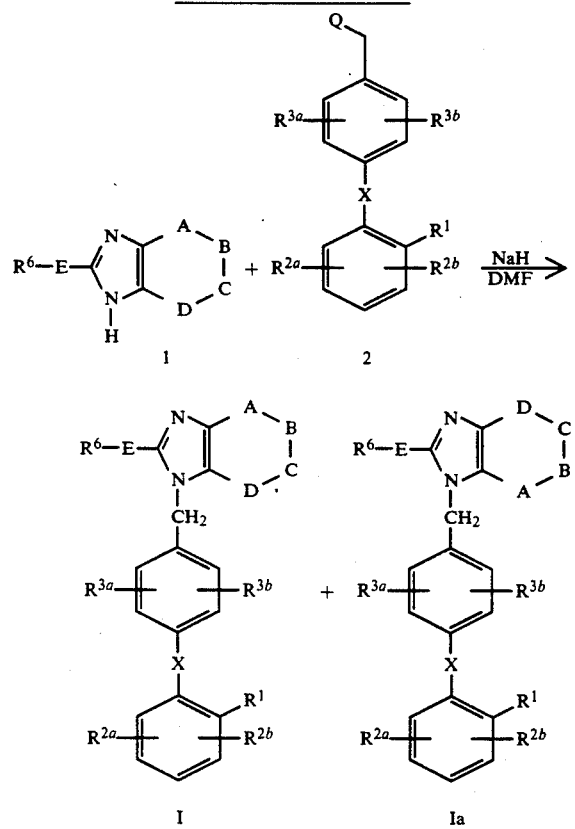

where Q = halo(I, Br, Cl), —O-tosyl, —O-mesyl

If substituents and/or the hetero atom positions in the six-membered ring are not symetrically disposed, the alkylation on the imidazole nitrogen(s) generally produces a mixture of two regioisomers as products arising from N$^1$ and N$^3$ alkylation. These regioisomers I and Ia possess distinct physico-chemical and biological properties and in most cases can be separated and purified by using conventional separation techniques such as chromatography (flash column chromatography, medium-pressure liquid chromatography, high performance liquid chromatography) and/or crystallization. In those cases where separation of regioisomers is difficult by conventional techniques, the mixture can be transformed into suitable derivatives that can be separated by the above separation methods. The structural assignments of the isomers can be made using Nuclear Overhauser Effect (NOE), $^1$H-$^{13}$C coupled NMR experiments or X-ray crystallography.

When there is potential for alkylation in the 6-membered heterocyclic ring, this can be avoided by the use of suitable protecting groups.

The substituted benzyl halides (2) including the more preferred alkylating agents (8a and 8b and 8c, Reaction Scheme 2) can be prepared as described in European Patent Applications 253,310 and 291,969 and the references cited therein. In addition a preferred method to prepare the biphenyl precursors 7a, 7b using Ni(0) or Pd(O) catalyzed cross-coupling reaction [E. Negishi, T. Takahashi, and A. O. King, *Org. Synthesis*, 66, 67 (1987)] is outlined in Reaction Scheme 2. As shown in Reaction Scheme 2, treatment of 4-bromotoluene (3) with t-BuLi, followed by the addition of a solution of ZnCl₂, produces the organo-zinc compound (5). Compound (5) is then coupled with 6a or 6b in the presence of Ni(PPh₃)Cl₂ catalyst to produce the desired biphenyl compound 7a or 7b. Similarly, 1-bromo-2-nitrobenzene (6c) is coupled with organo-zinc compound 5 in the presence of Pd(PPh₃)₄ catalyst [prepared by treating Cl₂Pd(PPh₃)₂ with (i-Bu)₂AlH (2 equiv.)] to give the biphenyl compound 7c. These precursors, 7a, 7b and 7c, are then transformed into halomethylbiphenyl derivatives 8a, 8b and 8c, respectively, according to procedures described in European Patent Applications 253,310 and 291,969.

When there is additional substitution on the second phenyl ring ($R^2$ not hydrogen) the preferred method to prepare the biphenyl precursors 7d and 7e, using the Pd(0) catalyzed cross-coupling reaction [J. K. Stille, *Angrew, Chem. Int. Ed. Engl.*, 25, 508 (1986)], is outlined in reaction Scheme 2a. As shown in reaction Scheme 2a, p-tolytrimethyltin (5a) is coupled with 6d or 6e in refluxing toluene in the presence of 5 mole % of Pd(PPh₃)₄ to produce the desired biphenyl compounds 7d and 7e. Table I illustrates the synthetic utility of this protocol. Compounds 7d ($R^2$=NO₂) and 7e ($R^2$=NO₂) could be converted to their respective chlorides by catalytic hydrogenation, diazotization and treatment with copper (I) chloride. The biphenyl fluorides which could not be obtained by direct coupling to a fluoro arylbromide were prepared from 7d ($R^2$=NO₂) and 7e ($R^2$=NO₂) via reduction, formation of the diazonium tetrafluoroborate salt and thermal decomposition. These precursors 7d ($R^2$=NO₂ or F or Cl) and 7e ($R^2$=NO₂ or F or Cl) are then transformed into the halomethyl biphenyl derivatives 8d and 8e, respectively according to the procedures described in European Patent Applications 253,310 and 292,969.

REACTION SCHEME 2

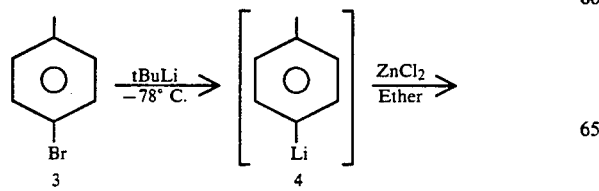

-continued
REACTION SCHEME 2

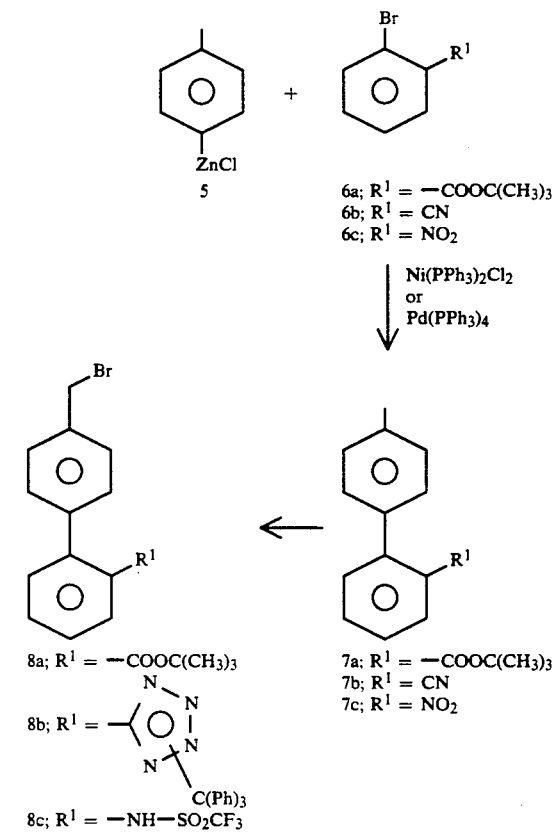

REACTION SCHEME 2a

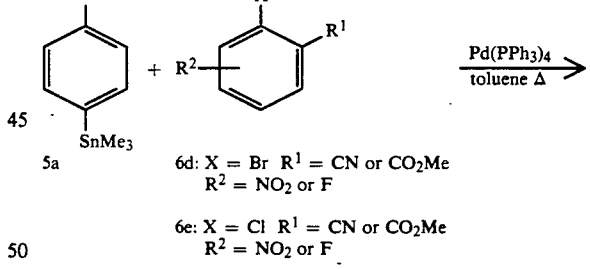

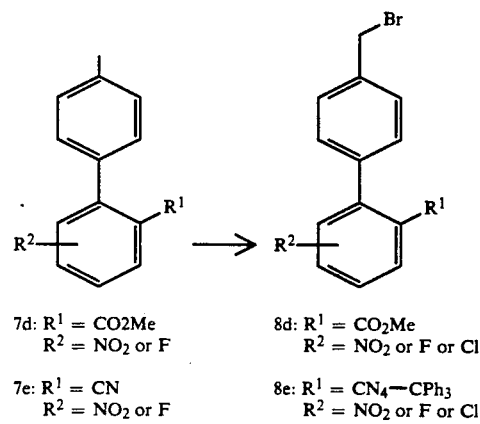

Biphenyl Synthesis Table I

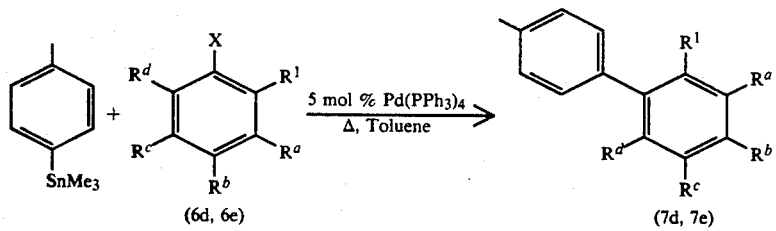

| X | $R^1$ | $R^a$ | $R^b$ | $R^c$ | $R^d$ | Product ($R^a$) | Rf (solvent) | Yield |
|---|---|---|---|---|---|---|---|---|
| Br | $CO_2Me$ | $NO_2$ | H | H | H | 7d (3'-nitro) | 0.35(15:1 Hex/EtOAc) | 71% |
| Br | CN | H | $NO_2$ | H | H | 7e (4'-nitro) | 0.62(2x 6:1 Hex/EtOAc) | 74% |
| Br | $CO_2Me$ | H | F | H | H | 7d (4'-fluoro) | 0.43(15:1 Hex/EtOAc) | 83% |
| Cl | $CO_2Me$ | H | H | $NO_2$ | H | 7d (5'-nitro) | 0.22(15:1 Hex/EtOAc) | 70% |
| Br | $CO_2Me$ | H | H | H | $NO_2$ | 7d (6'-nitro) | 0.24(15:1 Hex/EtOAc) | 79% |
| Br | CN | H | F | H | H | 7e (4'-fluoro) | 0.44(15:1 Hex/EtOAc) | 64% |
| Cl | CN | H | H | F | H | 7e (5'-fluoro) | 0.40(15:1 Hex/EtOAc) | 62% |

The heterocycles of type (1) can be prepared by any of the standard procedures described in the literature [J. A. Montgomery and J. A. Secrist III in "Comprehensive Heterocyclic Chemistry," Vol. 5, A. R. Katritsky and C. W. Rees Eds., Pergamon Press 1984; pp 567-597 and 631-656 and references cited therein]. As shown in Reaction Scheme 3, the most widely used starting materials are six member heterocyclic vicinal diamines (9). Fused imidazoles (10) can be prepared by condensation of (9) with an appropriate carboxylic acid, nitrile, imidate ester, or orthoesters, either neat, or in a solvent appropriate and compatible with the starting materials and reagents, such as polyphosphoric acid, ethanol, methanol, hydrocarbon solvents, and with a catalytic amount of acid if required. Oxidation of an imine formed by reaction of diamine (9) with an appropriate aldehyde using oxidants such as Cu (II), nitrobenzene, or 2,3-dichloro-5,6-dicyano-1,4-benzoquinone (DDQ) also affords heterocycles (10). Aminoamides (11, W=H) or diamides (11, W=R^6CO) can be converted to fused imidazoles (10) by heating neat, or at an elevated temperature in a solvent such as xylene under acidic or neutral conditions.

As shown in Reaction Scheme 4, methods of preparing heterocycles of types (12 and 13) involve treatment of diamines (9) with reagents such as urea, phosgene, potassium cyanate, alkyl chloroformates, dialkylcarbonate, or carbon disulfide in the presence of bases such as potassium hydroxide or potassium carbonate. Amino acids (14) of (15) can be converted to (13) via Curtius or Hoffman rearrangement on suitable derivatives such as acyl azides, hydroxyamides, or N-haloamides. Bicyclic compounds of type (16, E=sulfur or oxygen) are formed from 12 by reaction under neutral or basic conditions with alkyl halides, alkylmesylates, alkyltosylates, trialkyloxonium salts, or with an appropriate diazoalkane. Compounds of type (16; E=oxygen or sulfur) are prepared by displacement reactions using alkoxides or alkyl mecaptides with chloro intermediates as indicated.

Diamines of type 9 can be prepared by a wide variety of methods such as hydrolysis of bis-amides or amino amides, reduction of dinitro or aminonitro or hydrazino or azido groups, displacement of heteroaromatic halides or alkoxy or thio or alkylthio or hydroxy or alkyl sulfonyl groups with ammonia or amines, or rearrangement of acyl azides or amides or acids (Curtius, Hofman, or Schmidt rearrangements). [A. S. Tomcufcik, L. N. Starker in "Heterocyclic Compounds, Pyridine and it's Derivatives" Pt 3, E. Klingsberg Ed., Wiley Interscience, 1962, pp 59-62, and references cited there in; T. Nakagome in "Heterocyclic Compounds, Pyridazines" Vol. 28, R. N. Castle, Ed., Wiley Interscience, 1973, pp 597-601, and references cited therein; "Heterocyclic Compounds, The Pyrimidines" Vol. 16, D. J. Brown Ed., Wiley Interscience 1985, pp 299-325; E. Schipper, and A. R. Day J. Am. Chem. Soc. (1952) 74, 350; "Comprehensive Heterocyclic Chemistry," Vol. 5, A. R. Katritsky and C. W. Rees Eds., Pergamon Press 1984; pp 567-597 and 631-656 and references cited therein].

In cases wherein heterocycles of type 10 or 16 are not easily prepared from their corresponding diamines, or when these diamines cannot be prepared then alternative routes, involving fusion of the six member heterocycle onto an appropriately substituted imidazole, are used. Two of these routes are illustrated in Reaction Scheme 5. For example, imidazo[4,5-d][1,2,3]triazines (18) are preferentially prepared by treatment of amino carboxamido imidazoles (17) with sodium nitrite in aqueous acid. Precursor imidazoles (17) are prepared by degradation of an appropriately substituted xanthine or by condensation of an appropriate imidate ester with aminocyanoacetamide. Imidazo[4,5-b]pyridazines (20) can be prepared from imidazodicarboxylate esters (19) by treatment with hydrazine. Oxidation of (20) gives pyridazindiones (21). The oxygen(s) in (20) or (21) can be converted to other functionalities such as halides or thiones, which are themselves precursors for the synthesis of more elaborate systems ["Comprehensive Heterocyclic Chemistry," Vol. 5, A. R. Katritsky and C. W. Rees Eds., Pergamon Press 1984; pp 567-597 and 631-656 and references cited therein].

REACTION SCHEME 3

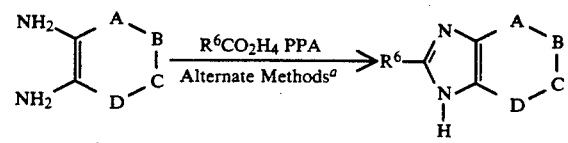

REACTION SCHEME 3

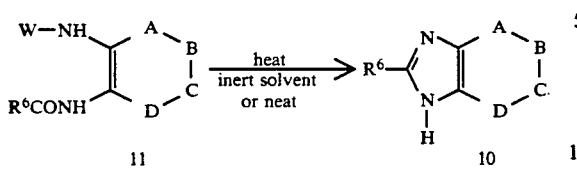

W = H or R⁶CO
ᵃAlternate reagents and reaction conditions:
R⁶C≡N, PPA
$$R^6-\underset{|}{\overset{OC_2H_5}{C}}=NH\cdot HCl, C_2H_5OH, \Delta$$
R⁶C(OCH₃)₃, toluene, H⁺, Δ
R⁶CHO, C₂H₅OH, Cu(OCOCH₃)₂.

REACTION SCHEME 4

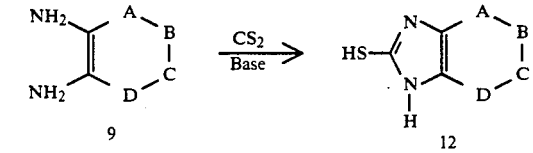

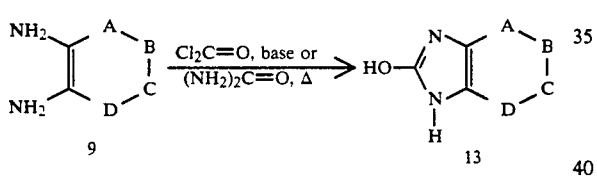

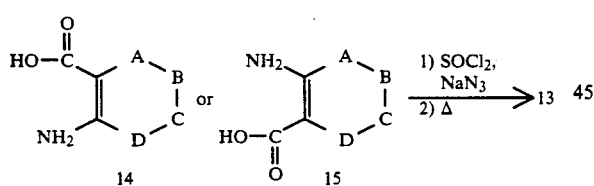

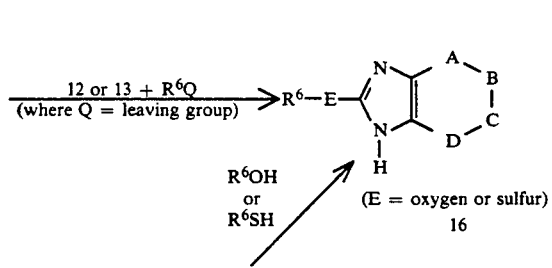

(E = oxygen or sulfur)

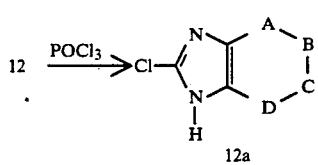

REACTION SCHEME 5

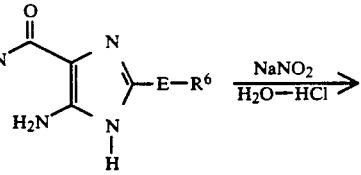

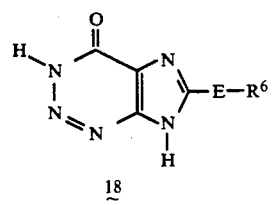

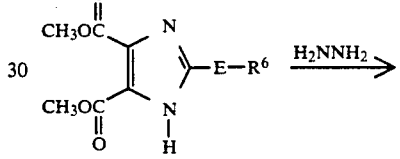

Moreover, as shown in Reaction Scheme 6, amino imidazole esters and amides are versatile intermediates for the preparation of purines. This scheme also illustrates the synthesis of the 6-membered heterocyclic ring after the alkylating agent 2 has been reacted with a suitably substituted imidazole to afford 22 or 24.

REACTION SCHEME 6

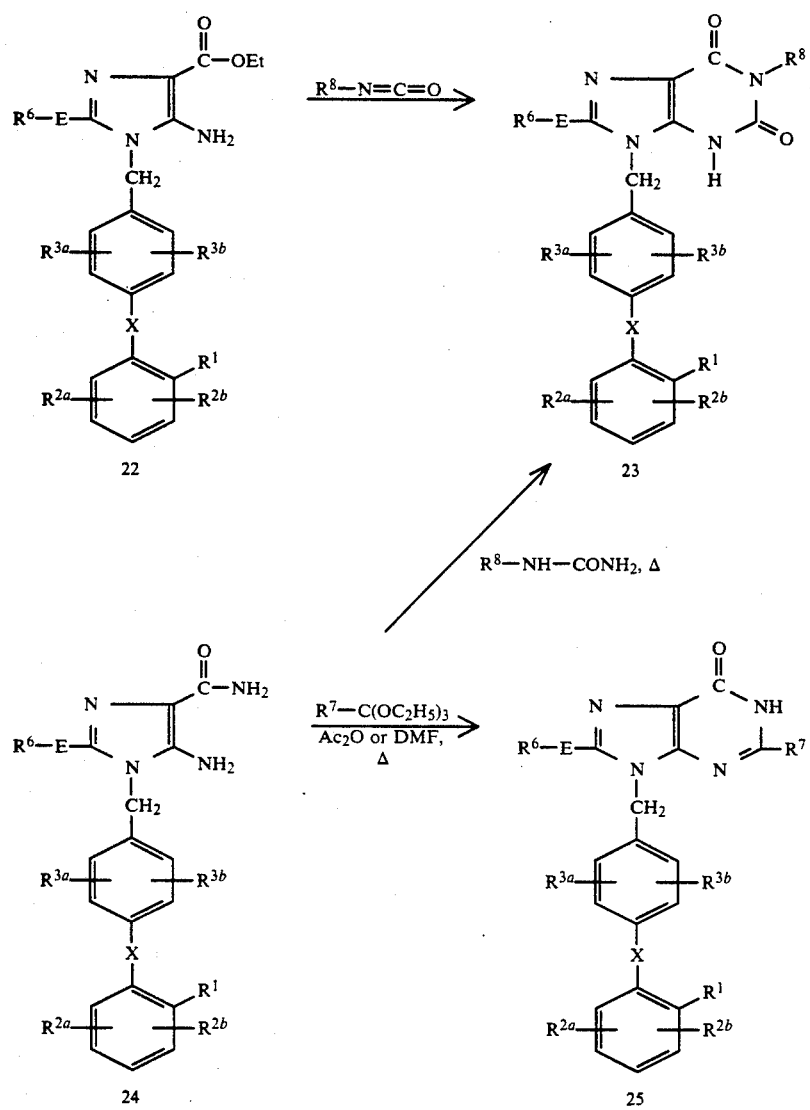

The preparation of reduced forms of heterocycles can be achieved by catalytic reduction, or by synthesis from a suitable imidazole precursor. For example, histidine and derivatives thereof react with formaldehyde to afford partially saturated imidazo(4,5-c) pyridines [cf. Neuberger, A. Biochem. J., (1944), 38, 309].

Compounds of formula I where $R^1$ is —CONHSO$_2R^{23}$ (where $R^{23}$=alkyl, aryl or heteroaryl) may be prepared from the corresponding carboxylic acid derivatives (I) as outlined in Scheme 7. The carboxylic acid (I), obtained as described in Scheme 1, can be converted into the corresponding acid chloride by treatment with refluxing thionyl chloride or preferably with oxalylchloride and a catalytic amount of dimethylformamide at low temperature [A. W. Burgstahler, L. O. Weigel, and C. G. Shaefer—*Synthesis*, 767, (1976)]. The acid chloride then can be treated with the alkali metal salt of $R^{23}SO_2NH_2$ to form the desired acylsulfonamide 26. Alternatively, these acylsulfonamides may be also prepared from the carboxylic acids using N,N-diphenylcarbamoyl anhydride intermediates [F. J. Brown et al—European Patent Application, EP 199543; K. L. Shepard and W. Halczenko—*J. Het. Chem.*, 16, 321 (1979)]. Preferably the carboxylic acids can be converted into acyl-imidazole intermediates, which then can be treated with an appropriate aryl or alkylsulfonamide and diazabicycloundecane (DBU) to give the desired acylsulfonamide 26 [J. T. Drummond and G. Johnson—*Tetra. Lett.*, 29, 1653 (1988)].

SCHEME 7

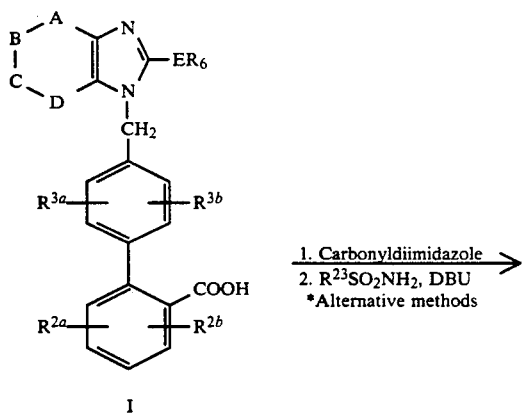

1. Carbonyldiimidazole
2. $R^{23}SO_2NH_2$, DBU
   *Alternative methods

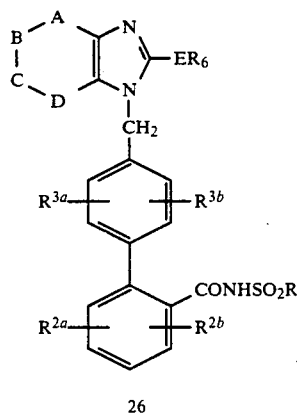

26

*Alternative Methods:
a) (i) $SOCl_2$, reflux
   (ii) $R^{23}SO_2NH^-M^+$ (where M is Na or Li)

b) (i) $(COCl)_2$-DMF, $-20°$ C.
   (ii) $R^{23}SO_2NH^-M^+$ c) (i) N(N,N-Diphenylcarbamoyl)pyridinium chloride/Aq. NaOH
   (ii) $R^{23}SO_2NH^-M^+$.

Compounds of formula I where $R^1$ is $-SO_2NH-COR^{23}$ may be prepared as outlined in Scheme 8. The nitro compound 7c (prepared as described in Scheme 2) can be reduced to the corresponding amino compound and converted into aromatic diazonium chloride salt, which then can be reacted with sulfur-dioxide in the presence of a copper(II) salt to form the corresponding arylsulfonylchloride 27 [H. Meerwein, G. Dittmar, R. Gollner, K. Hafner, F. Mensch and O. Steifort—*Chem. Ber.*, 90, 841 (1957); A. J. Prinsen and H. Cerfontain, *Recueil*, 84, 24 (1965); E. E. Gilbert, *Synthesis*, 3 (1969) and references cited therein]. The sulfonyl chloride can be reacted with ammonia in aqueous solution or in an inert organic solvent [F. H. Bergheim and W. Baker, *J. Amer. Chem. Soc.*, 66, (1944), 1459], or with dry powdered ammonium carbonate, [E. H. Huntress and J. S. Autenrieth, *J. Amer. Chem. Soc.*, 63, (1941), 3446; E. H. Huntress and F. H. Carten, *J. Amer. Chem. Soc.*, 62, (1940), 511] to form the sulfonamide 28. The benzylbromide 30 may be prepared from the sulfonamide 28 as outlined in Scheme 8, and then can be reacted with an alkali metal salt of an appropriate heterocyclic compound to form the key sulfonamide 31. The sulfonamide 31 may be also prepared from the aromatic sulfonyl chloride 36, which may be prepared from the aryl amine 35 as outlined in Scheme 9. The acylation of 31 with appropriate acyl chlorides (or acyl-imidazoles or other acylating agents) may produce the desired acyl-sulfonamides 32.

SCHEME 8

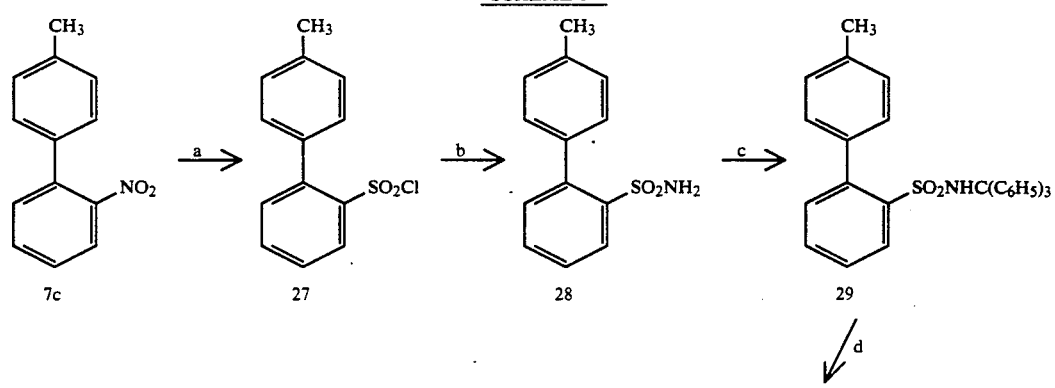

SCHEME 8

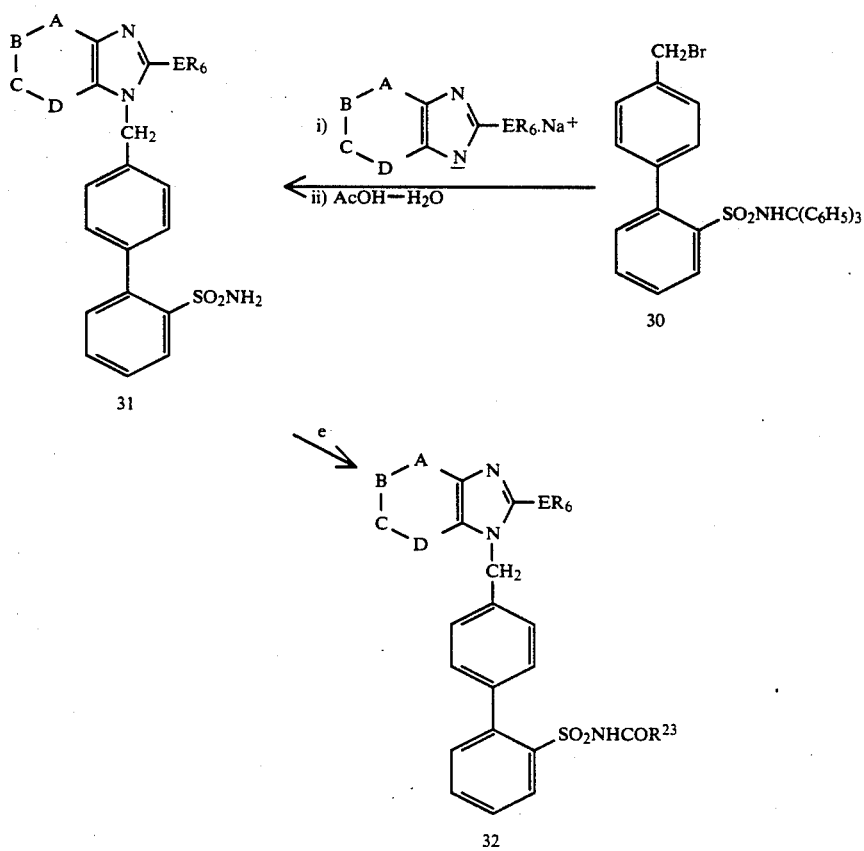

a i) H₂/Pd—C, ii) NaNO₂—HCl, iii) SO₂, AcOH, CuCl₂
b NH₃ or (NH₄)₂CO₃
c (C₆H₅)₃CCl, Et₃N, CH₂Cl₂, 25° C.
d N-Bromosuccinimide
e R²³COCl or R²³CO-Im or other acylating agents.

The compounds bearing $R^1$ as —SO₂NHR²³ (where $R^{23}$ is heteroaryl) may be prepared by reacting the aromatic sulfonyl chloride 36 with appropriate heteroaryl amines as outlined in Scheme 9. The sulfonyl chloride 36 may be the prefered intermediate for the synthesis of this class of compounds. The aromatic sulfonyl chlorides may also be prepared by reacting the sodium salt of aromatic sulfonic acids with PCl₅ or POCl₃ [C. M. Suter, *The organic Chemistry of Sulfur*, John Wiley & sons, 459, (1944)]. The aromatic sulfonic acid precursors may be prepared by chlorosulfonation of the aromatic ring with chlorosulfonic acid [E. H. Huntress and F. H. Carten, *J. Amer. Chem. Soc.*, 62, 511 (1940)].

SCHEME 9

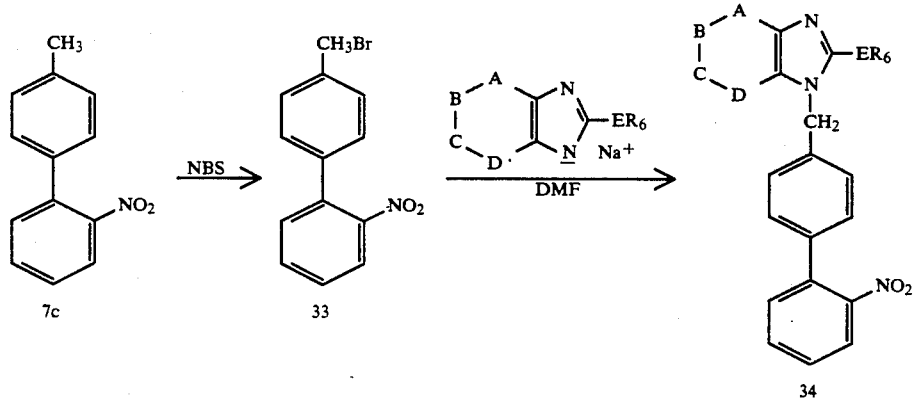

SCHEME 9
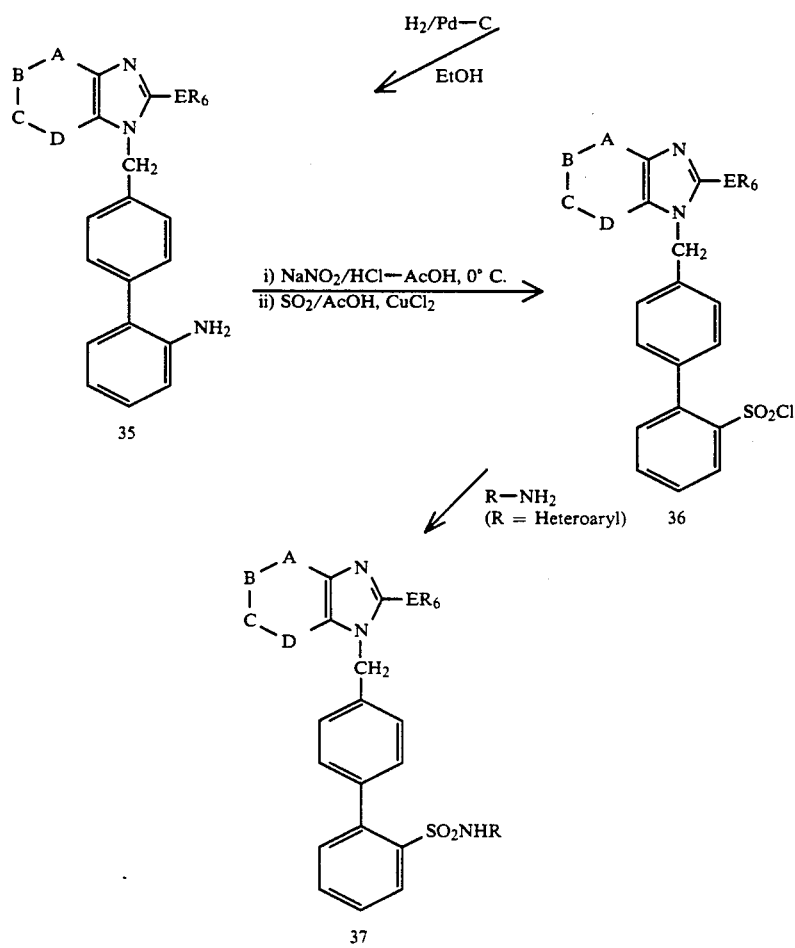
SCHEME 10
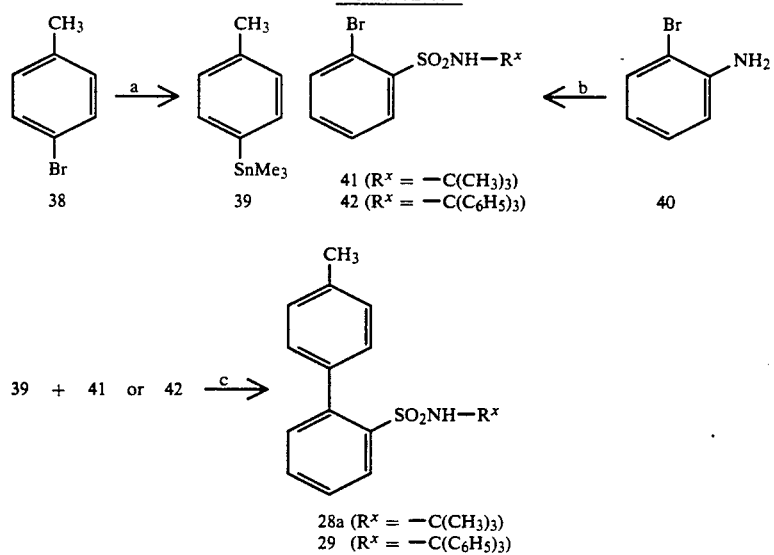
a i) t-BuLi/ether, −78° C. ii) Me₃SnCl
b i) NaNO₂/HCl ii) SO₂, CuCl₂
c Pd(PPh₃)₄, Toluene or (PPh₃)₂PdCl₂, DMF, 90° C.

SCHEME 11
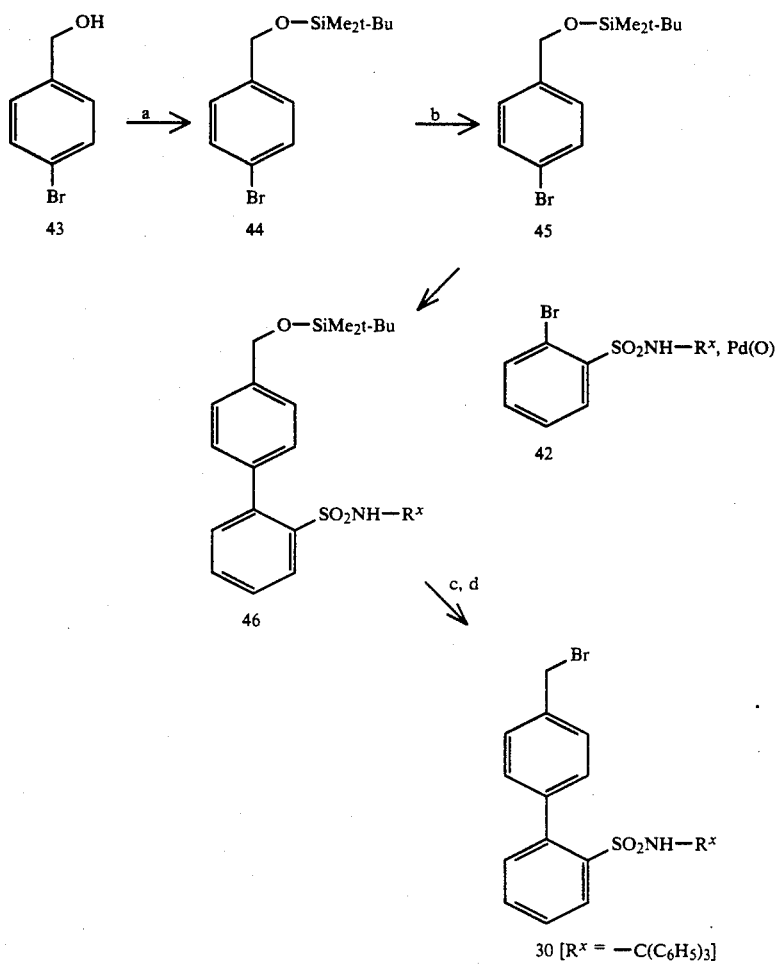
a t-BuMe$_2$Si—Cl/Imidazole, DMF
b t-BuLi, −78° C., Me$_3$SnCl
c Tetrabutylammonium fluoride
d CBr$_4$/Ph$_3$P.
SCHEME 12
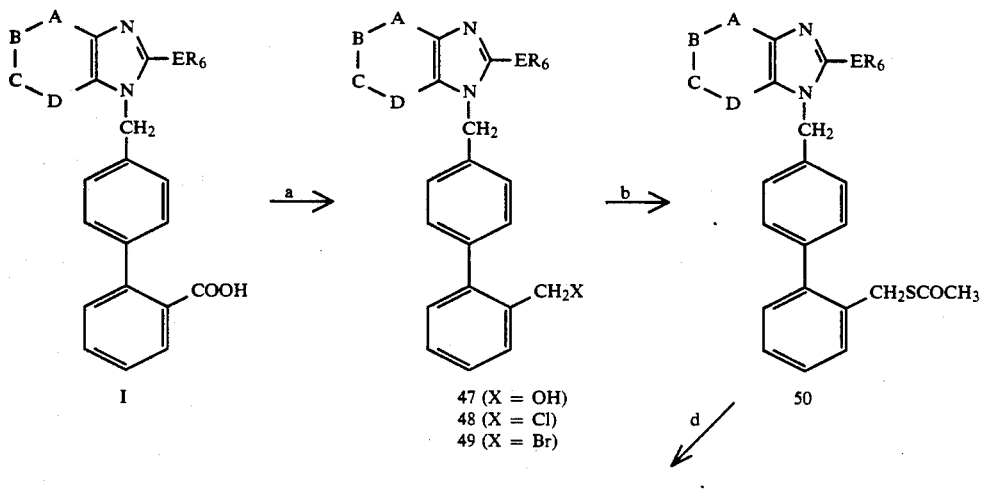

-continued
SCHEME 12
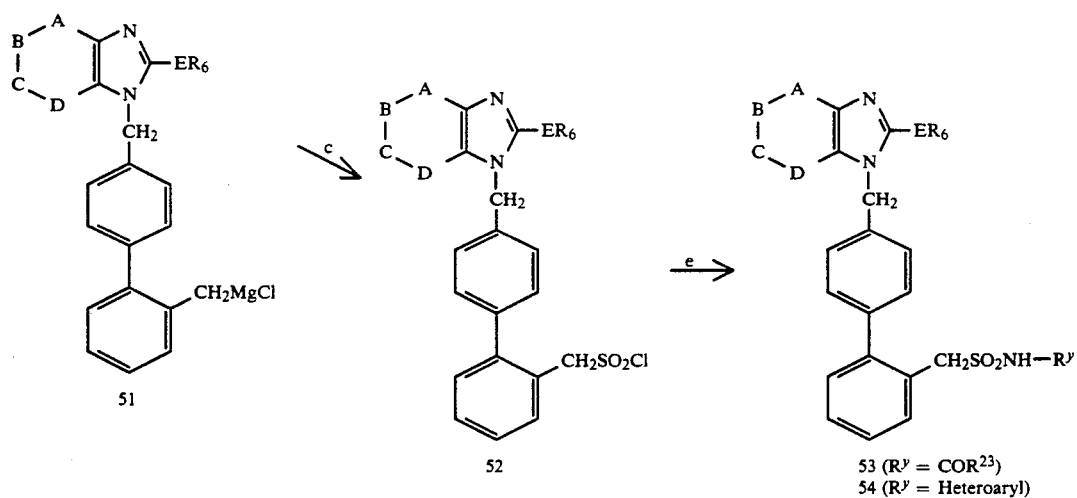
a i)EtOCOCl/Et$_3$N, THF, 0° C. ii) NABH$_4$ iii) CCl$_4$ or CBr$_4$/PPh$_3$
b AcSK
c SO$_2$Cl$_2$
d Cl$_2$, AcOH, H$_2$O or, i) SO$_2$Cl$_2$ ii) oxidation
e R$^y$NH$_2$ or, i) NH$_3$ ii) Acylation
SCHEME 13
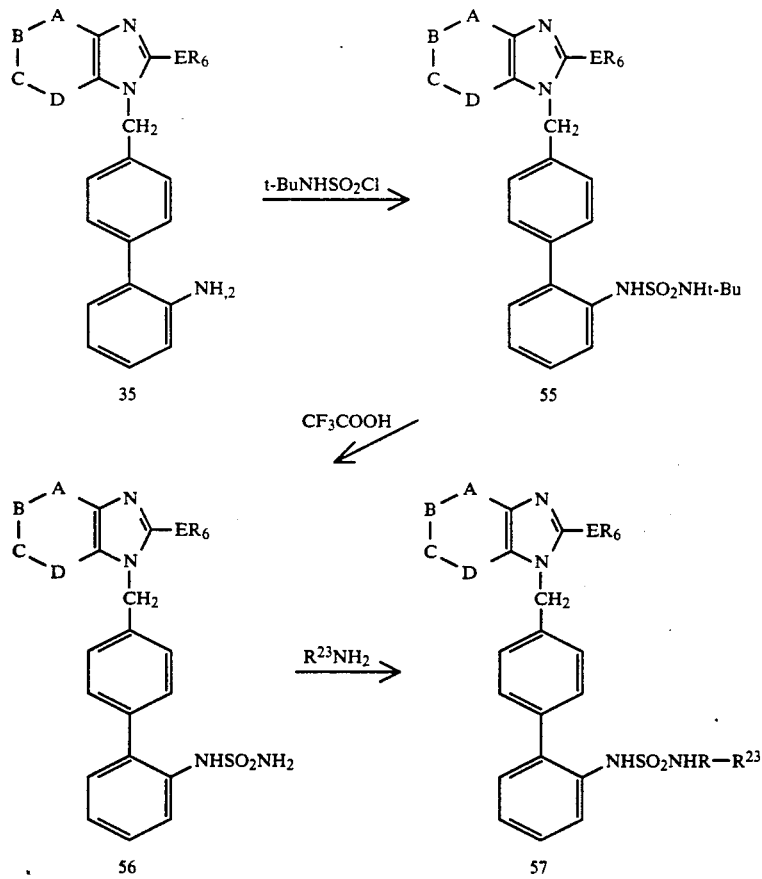

SCHEME 14
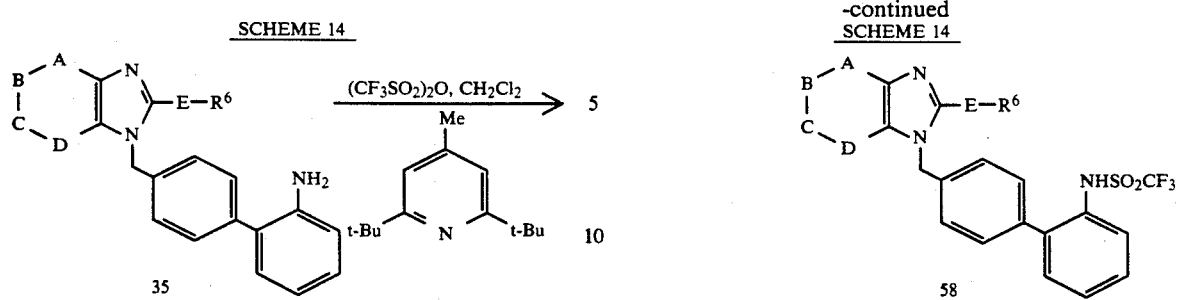
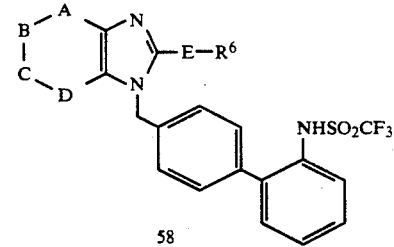
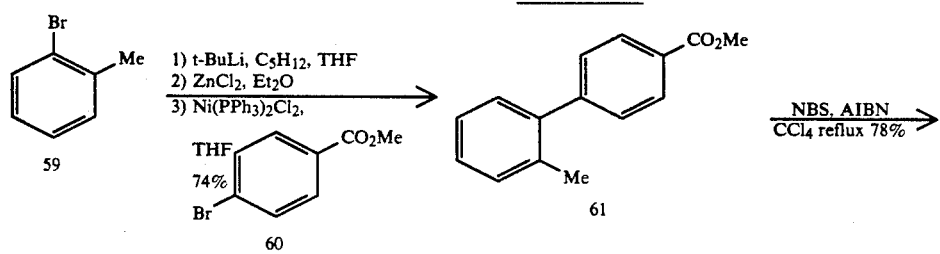
SCHEME 15
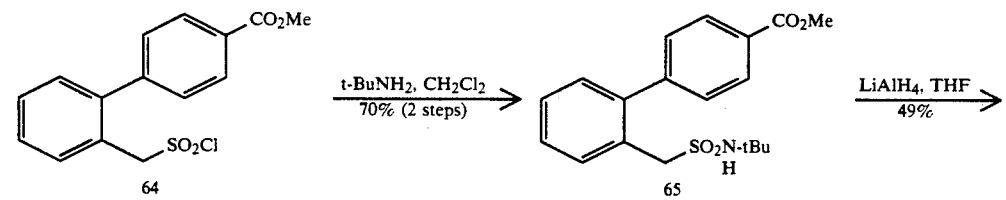
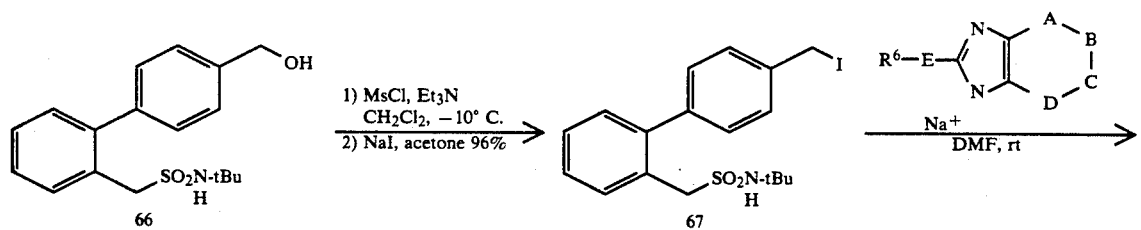
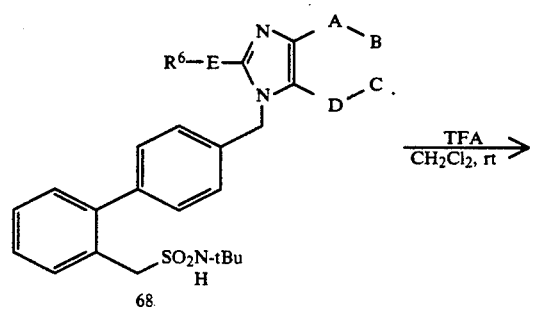

-continued
SCHEME 15

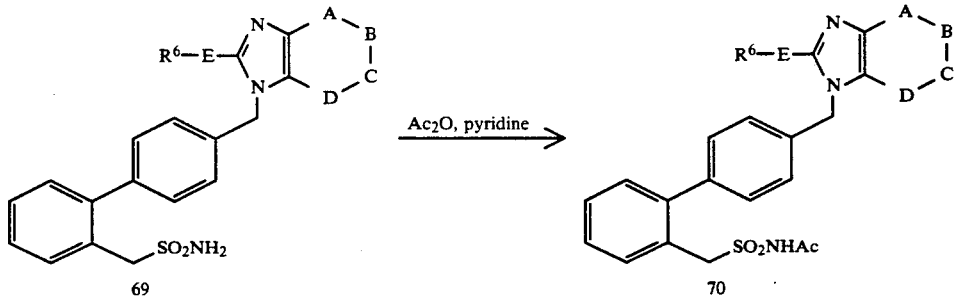

The biaryl sulfonamides 28a and 29 can be prepared alternatively using palladium(0) catalyzed cross-coupling reactions of appropriate aryl-organotin precursors [J. K. Stille, *Pure Appl. Chem.*, 57, 1771 (1985); T. R. Baiely, *Tetra Lett.*, 27, 4407 (1986); D. A. Widdowson and Y. Z. Zhang, *Tetrahedron*, 42, 2111 (1986)], as outlined in Scheme 10. The organotin compound 39 [S. M. Moerlein, *J. Organometallic Chem.*, 319, 29 (1987)], obtained from the aromatic precursor 38, may be coupled with aryl sulfonamides 41 and 42 using Pd(PPh$_3$)$_4$ or (PPh$_3$)$_2$PdCl$_2$ as catalysts to give biaryl sulfonamides 28a and 29, respectively. Similarly, the benzyl bromide 30 may be alternatively prepared from the appropriate organotin precursor 45 using the Pd(0) catalyzed cross-coupling reaction as outlined in Scheme 11.

The compounds bearing R$^1$ as —CH$_2$SO$_2$NHCOR$^{23}$ and —CH$_2$SO$_2$NHR$^{23}$ may be prepared as outlined in Scheme 12. The key precursor aryl-methanesulfonyl chloride 52 may be prepared either from the reaction of aryl-methylmagnesium chloride (51) (obtained from the corresponding benzyl chloride (48)) with sulfurylchloride [S. N. Bhattacharya, C. Eaborn and D. P. M. Walton, *J. Chem. Soc.* C, 1265 (1968)], or by oxidation of the aryl-methylthioacetate (50) (prepared from the benzyl bromide 49) with chlorine in presence of trace amount of water [Bagnay and Dransch, *Chem. Ber.*, 93, 784 (1960)]. Alternatively, the aryl-methylthioacetate (50) may be oxidized with sulfuryl chloride in presence of acetic anhydride to form aryl-methylsulfinyl chloride [S. Thea and G. Cevasco, *Tetra. Lett.*, 28, 5193 (1987)], which can be further oxidized with appropriate oxidizing agents to give the sulfonyl chloride 52. The compounds 53 and 54 can be obtained by reacting the sulfonyl chloride 52 with appropriate amines.

Compounds where R$^1$=—NHSO$_2$NHR$^{23}$ may be prepared by the reaction of appropriate primary amines with the sulfamide 56 [S. D. McDermott and W. J. Spillane, *Synthesis*, 192 (1983)], as described in Scheme 13. The compound 56 may be obtained from the corresponding N-t-butylsulfamide 55 after treatment with anhydrous trifluoroacetic acid [J. D. Catt and W. L. Matier, *J. Org. Chem.*, 39, 566 (1974)], which may be prepared by the reaction of the aromatic amine 35 with t-butylsulfamoyl chloride [W. L. Matier, W. T. Comer and D. Deitchman, *J. Med. Chem.*, 15, 538 (1972)].

Antagonists of Formula I in which R$^1$=—NHSO$_2$CF$_3$ may be prepared as illustrated in Schemes 9 and 14. Bromination of 7c (prepared as described in Scheme 2) with N-bromosuccinimide affords 4-bromomethyl-2'-nitrobiphenyl (33). This bromide is then used to alkylate the sodium salt of an appropriate heterocyclic compound in anhydrous DMF, affording 34. Subjection of 34 to catalytic reduction with Pd/C catalyst then affords the corresponding amino-derivative 35, which is converted upon treatment with trifluoromethansulfonic anhydride to the sulfonamide 58.

Antagonists of Formula I in which R$^1$=—CH$_2$SO$_2$NHCOR$^{23}$ may be prepared as illustrated in Scheme 15. 2-Bromotoluene (59) is treated with t-butyllithium and then zinc chloride. Coupling of the resulting metallo-zinc species with 4-bromobenzoic acid methyl ester (60) is then carried out with bis(triphenylphosphine)nickle(II) chloride as catalyst. Bromination of the resulting biphenyl (61) is then carried out using N-bromosuccinimide, affording bromide 62. Treatment of the bromide with thiourea affords the salt 63 which is treated with chlorine to yield sulfonyl chloride 64. Treatment of 64 with t-butylamine affords sulfonamide 65, which is converted by treatment with lithium aluminum hydride to the alcohol 66. Conversion of 66 to the corresponding iodide 67 is carried out by treatment with methanesulfonyl chloride to afford a sulfonate ester, followed by treatment with sodium iodide in acetone. The iodide 67 is used to alkylate the sodium salt of an appropriate heterocyclic compound, affording the sulfonamide 68. Treatment of 68 with trifluoroacetic acid then affords the sulfonamide analog 69, which on further treatment with acetic anhydride and pyridine affords the desired acylsulfonamides 70.

Halogenation of the imidazo[4,5-b]pyridine ring at the 6-position can be accomplished using Br$_2$, or N-bromosuccinimide. Halogenation of the 7-position can be accomplished by reaction of the corresponding imidazopyridine-4-oxide (prepared by reaction of the imidazopyridine with peracids such as m-chloroperbenzoic acid) with POCl$_3$. When the 7-position is substituted with other than hydrogen, halogenation at the 5-position of the 4(N)-oxide precursor occurs upon treatment with POCl$_3$. Chlorides may be substistuted by bromides or iodides by treatment with either HBr or HI, respectively, in a solvent such as HOAc.

2-Alkyl-imidazo[4,5-b]pyridines can be substituted at the 5, 6, or 7 positions by displacement of a halogen at that position by nucleophiles such as cyanide, amines, copper alkoxides, trialkylphosphites, and thiolates. Also, substitution of the halogens, in particular bromides or iodides, can be accomplished by reaction with a coupling partner such as alkylzinc or arylzinc halides, or monoalkylarylphosphonites in the presence of an appropriate metal catalyst such as nickle, palladium, ruthenium, or platinum. In cases where the reaction is sluggish or complicated due to an acidic proton, the imidazopyridine may be protected at the 1, 3, or 4 positions by benzyl or other arylmethyl groups.

It will be appreciated by those skilled in the art that functional group transformations can be conducted on aryl and heterocyclic rings to afford desired analogs. For example, esters may be converted to amides by heating them with amines and an amide nitrogen if present in the heterocycle may be alkylated using bases such as sodium hydride in DMF with the appropriate alkyl halide. Functional group protection throughout these syntheses will be chosen to be compatible with subsequent reaction conditions. Ultimately such protecting groups will be removed to generate the desired optimally active compounds of Formula I. For example, $R^1$ as carboxyl is often protected as its t-butyl ester which in the last step is removed by treatment with trifluoroacetic acid. Aqueous acetic acid at room temperature overnight is a preferred method to remove a trityl protecting group to liberate an $R^1$ tetrazole group.

The compounds of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases; e.g., dicyclohexylamine salts, N-methyl-D-glucamine, salts with amino acids like arginine, lysine, and the like. Also, salts with organic and inorganic acids may be prepared; e.g., HCl, HBr, $H_2SO_4$, $H_3PO_4$, methane-sulfonic, toluene-sulfonic, maleic, fumaric, camphorsulfonic. The non-toxic, physiologically, acceptable salts are preferred, although other salts are also useful; e.g., in isolating or purifying the product.

The salts can be formed by conventional means such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

Angiotensin II (AII) is a powerful arterial vasoconstrictor, and it exerts its action by interacting with specific receptors present on cell membranes. The compounds described in the present invention act as competitive antagonists of AII at the receptors. In order to identify AII antagonists and determine their efficacy in vitro, the following two ligand-receptor binding assays were established.

RECEPTOR BINDING ASSAY USING RABBIT AORTAE MEMBRANE PREPARATION

Three frozen rabbit aortae (obtained from Pel-Freeze Biologicals) were suspended in 5 mM Tris-0.25M Sucrose, pH 7.4 buffer (50 ml) homogenized, and then centrifuged. The mixture was filtered through a cheesecloth and the supernatant was centrifuged for 30 minutes at 20,000 rpm at 4° C. The pellet thus obtained was resuspended in 30 ml of 50 mM Tris-5 mM $MgCl_2$ buffer containing 0.2% Bovine Serum Albumin and 0.2 mg/ml Bacitration and the suspension was used for 100 assay tubes. Samples tested for screening were done in duplicate. To the membrane preparation (0.25 ml) there was added $^{125}I$-Sar$^1$Ile$^8$-angiotensin II [obtained from New England Nuclear] (10 ul; 20,000 cpm) with or without the test sample and the mixture was incubated at 37° C. for 90 minutes. The mixture was then diluted with ice-cold 50 mM Tris-0.9% NaCl, pH 7.4 (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration ($IC_{50}$) of potential AII antagonist which gives 50% displacement of the total specifically bound $^{125}I$-Sar$^1$Ile$^8$-angiotensin II was presented as a measure of the efficacy of such compounds as AII antagonists.

RECEPTOR ASSAY USING BOVINE ADRENAL CORTEX PREPARATION

Bovine adrenal cortex was selected as the source of AII receptor. Weighed tissue (0.1 g is needed for 100 assay tubes) was suspended in Tris.HCl (50 mM), pH 7.7 buffer and homogenized. The homogenate was centrifuged at 20,000 rpm for 15 minutes. Supernatant was discarded and pellets resuspended in buffer [$Na_2HPO_4$ (10 mM)-NaCl (120 mM)-disodium EDTA (5 mM) containing phenylmethane sulfonyl fluoride (PMSF) (0.1 mM)]. (For screening of compounds, generally duplicates of tubes are used). To the membrane preparation (0.5 ml) there was added 3H-angiotensin II (50 mM) (10 ul) with or without the test sample and the mixture was incubated at 37° C. for 1 hour. The mixture was then diluted with Tris buffer (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration ($IC_{50}$) of potential AII antagonist which gives 50% displacement of the total specifically bound $^3H$-angiotensin II was presented as a measure of the efficacy of such compounds as AII antagonists.

The antihypertensive effects of the compounds described in the present invention may be evaluated using the methodology described below:

Male Charles River Sprague-Dawley rats (300–375 gm) were anesthetized with methohexital (Brevital; 50 mg/kg i.p.) and the trachea was cannulated with PE 205 tubing. A stainless steel pithing rod (1.5 mm thick, 150 mm long) was inserted into the orbit of the right eye and down th spinal column. The rats were immediately placed on a Harvard Rodent Ventilator (rate—60 strokes per minute, volunm—1.1 cc per 100 grams body weight). The right carotid artery was ligated, both left and right vagal nerves were cut, and the left carotid artery was cannulated with PE 50 tubing for drug administration, and body temperature was maintained at 37° C. by a thermostatically controlled heating pad which received input from a rectal temperature probe. Atropine (1 mg/kg i.v.) was then administered, and 15 minutes later propranolol (1 mg/kg i.v.). Thirty minutes later angiotensin II or other agonists were administered intravenously at 30-minute intervals and the increase in the diastolic blood pressure was recorded before and after drug or vehicle administration.

Using the methodology described above, representative compounds of this invention were evaluated and were found to exhibit an activity of at least $IC_{50} < 50$ μM, thereby demonstrating and confirming the utility of the compounds of the invention as effective A II antagonists.

The compounds of the invention are useful in treating hypertension. They are also of value in the management of acute and chronic congestive heart failure. These compounds may also be expected to be useful in the treatment of secondary hyperaldosteronism, primary and secondary pulmonary hyperaldosteronism, primary and secondary pulmonary hypertension, renal failure such as diabetic nephropathy, glomerulonephritis, scleroderma, glomerular sclerosis, proteinuria of primary renal disease, end stage renal disease, renal transplant therapy, and the like, renal vascular hypertension, left ventricular dysfunction, diabetic retinopathy and in the management of vascular disorders such as migraine, Raynaud's disease, luminal hyperclasia, and to minimize the atherosclerotic process. The application of the compounds of this invention for these and similar disorders will be apparent to those skilled in the art.

The compounds of this invention are also useful to treat elevated intraocular pressure and to enhance retinal blood flow and can be administered to patients in need of such treatment with typical pharmaceutical formulations such as tablets, capsules, injectables and the like as well as topical ocular formulations in the form of solutions, ointments, inserts, gels, and the like. Pharmaceutical formulations prepared to treat intraocular pressure would typically contain about 0.1% to 15% by weight, preferably 0.5% to 2% by weight, of a compound of this invention.

In the management of hypertension and the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a which those skilled in the art will recognize, the dosage range will generally be about 1 to 1000 mg. per patient per day which can be administered in single or multiple doses. Perferably, the dosage range will be about 2.5 to 250 mg. per patient per day; more preferably about 5 to 150 mg. per patient per day.

The compounds of this invention can also be administered in combination with other antihypertensives and/or diuretics and/or angiotensin converting enzyme inhibitors and/or calcium channel blockers. For example, the compounds of this invention can be given in combination with such compounds as amiloride, atenolol, bendroflumethiazide, chlorothalidone, chlorothiazide, clonidine, cryptenamine acetates and cryptenamine tannates, deserpidine, diazoxide, guanethidene sulfate, hydralazine hydrochloride, hydrochlorothiazide, metolazone, metoprolol tartate, methyclothiazide, methyldopa, methyldopate hydrochloride, minoxidil, pargyline hydrochloride, polythiazide, prazosin, propranolol, *rauwolfia serpentina*, rescinnamine, reserpine, sodium nitroprusside, spironolactone, timolol maleate, trichlormethiazide, trimethophan camsylate, benzthiazide, quinethazone, ticrynafan, triamterene, acetazolamide, aminophylline, cyclothiazide, ethacrynic acid, furosemide, merethoxylline procaine, sodium ethacrynate, captopril, delapril hydrochloride, enalapril, enalaprilat, fosinopril sodium, lisinopril, pentopril, quinapril hydrochloride, ramapril, teprotide, zofenopril calcium, diflusinal, diltiazem, felodipine, nicardipine, nifedipine, niludipine, nimodipine, nisoldipine, nitrendipine, and the like, as well as admixtures and combinations thereof.

Typically, the individual daily dosages for these combinations can range from about one-fifth of the minimally recommended clinical dosages to the maximum recommended levels for the entities when they are given singly.

To illustrate these combinations, one of the angiotensin II antagonists of this invention effective clinically in the 2.5-250 milligrams per day range can be effectively combined at levels at the 0.5-250 milligrams per day range with the following compounds at the indicated per day dose range: hydrochlorothiazide (15-200 mg) chlorothiazide (125-2000 mg), ethacrynic acid (15-200 mg), amiloride (5-20 mg), furosemide (5-80 mg), propranolol (20-480 mg), timolol maleate (5-60 mg.), methyldopa (65-2000 mg), felodipine (5-60 mg), nifedipine (5-60 mg), and nitrendipine (5-60 mg). In addition, triple drug combinations of hydrochlorothiazide (15-200 mg) plus amiloride (5-20 mg) plus angiotensin II antagonist of this invention (3-200 mg) or hydrochlorothiazide (15-200 mg) plus timolol maleate (5-60) plus an angiotensin II antagonist of this invention (0.5-250 mg) or hydrochlorothiazide (15-200 mg) and nifedipine (5-60 mg) plus an angiotensin II antagonist of this invention (0.5-250 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 1 to 100 mg. of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the unit dosage unitform is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occuring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples further illustrate the preparation of the compounds of Formula I and their incorporation into pharmaceutical compositions and, as such, are not to be considered or construed as limiting the invention recited in the appended claims.

EXAMPLE 1

Preparation of 2-t-Butoxycarbonyl-4'-bromomethylbiphenyl

Step 1: 2-t-Butoxycarbonyl-4'-methylbiphenyl

To a solution of p-bromotoluene (30 g) in dry ether (150 ml) at −78° C., a solution of t-BuLi in pentane (1.7M) (210 ml) was added slowly over a period of 1 hour and 30 minutes, using a dropping funnel. The bath was then removed and the mixture was stirred at room temperature for an additional 2 hours. The content of the flask was then added slowly (using a cannula) at room temperature to a premixed solution of $ZnCl_2$ in ether (1M) (180 ml) and dry THF (360 ml). The mixture was stirred for 2 hours at that temperature and the slurry was added (using a cannula) to a solution of 2-t-butoxycarbonyliodobenzene (35.6 g), and $NiCl_2(Ph_3P)_2$ (2.1 g) in dry THF (360 ml). The mixture, after stirring at room temperature overnight (18 hours), was poured slowly under stirring into ice-cold 0.5N HCl (1500 ml). The organic layer was separated, and the aqueous phase was extracted with ether (3×300 ml). The combined organic layer was washed with water, brine and then dried over $MgSO_4$. Removal of the solvent gave the crude product as an oil (32 g). The material was purified on a silica gel flash column using ethylacetate/hexane (1:12) to give the titled compound as an oil (24 g, 76%).

NMR ($CDCl_3$) δ1.24 (s, 9H), 2.42 (s, 3H), 7.2–7.8 (m, 8H); FAB-MS: m/e 269 (M+H).

Step 2: 2-t-Butoxycarbonyl-4'-bromomethylbiphenyl

The titled compound was prepared from 2-t-Butoxycarbonyl-4'-methylbiphenyl (obtained from Step 1) according to the procedure described in European Patent Application EP 0,253,310.

EXAMPLE 2

Preparation of N-Triphenylmethyl-5-(4'-bromomethylbiphen-2-yl)tetrazole

Step 1: 2-cyano-4'-methylbiphenyl

To a solution of p-bromotoluene (30 g) in dry ether (150 ml) at −78° C., a solution of t-BuLi in pentane (1.7M) (210 ml) was added slowly over a period of 1 hour and 30 minutes, using a dropping funnel. The bath was then removed and the mixture was stirred at room temperature for an additional 2 hours. The content of the flask was then added slowly (using a cannula) at room temperature to a premixed solution of $ZnCl_2$ in ether (1M) (180 mL) and dry THF (360 mL). The mixture was stirred for 2 hours at that temperature and the slurry was added (using a cannula) to a solution of 2-bromobenzonitrile (21.3 g) and $NiCl_2(Ph_3P)_2$ (2.1 g) in dry THF (300 ml). The mixture, after stirring at room temperature overnight (18 hours), was poured slowly under stirring into ice cold 0.5N HCl (1500 ml). The organic layer was separated, and the aqueous phase was extracted with ether (3×300 ml). The combined organic layer was washed with water, brine and then dried over $MgSO_4$. Removal of the solvent gave the crude product as a semisolid mass (34 g). The material was purified on a silica gel flash column using ethylacetate/hexane (1:12) to give the desired nitrile as a low melting solid (28 g, 88%).

NMR ($CDCl_3$) δ2.42 (s, 3H), 7.2–7.8 (m, 8H).

FAB-MS: m/e 194 (M+H).

Step 2: Trimethylstannyl azide

To a concentrated solution of $NaN_3$ (40 g) in water (100 ml), a solution of trimethyltin chloride (20 g) in dioxane (10 ml) was added in three portions under vigorous stirring. An instantaneous precipitate formation was observed. The mixture, after stirring overnight at room temperature, was filtered. The residue was washed with water, and dried under suction and the in vacuo over $P_2O_5$.

Yield 18.7 g (81%), mp 132°–136° C.

Step 3: N-Triphenylmethyl-5-(4'-bromomethylbiphen-2-yl)tetrazole

The titled compound was prepared starting from 2-cyano-4'-methylbiphenyl (Step 1) as described in European Patent Application EP 0,291,969.

EXAMPLE 3

2-butyl-3-[(2'-Carboxybiphenyl-4-yl)methyl]-3H-imidazo[4,5-b]pyridine

Step 1: Preparation of 2-butylimidazo[4,5-b]pyridine

A mixture of valeric acid (5.50 mL, 50.4 mmol), 2,3-diaminopyridine (5.0 g, 45.8 mmol), and polyphosphoric acid (50 g) was heated to 100° C. with stirring for 5 hours. Basification ($NH_4OH$), extraction (EtOAc, 4×20 mL), drying ($K_2CO_3$), and concentration gave 7.61 g (95%) of the title compound as an amorphous tan solid which was judged pure by $^1H$ NMR and tlc (mp ca 80° C. without recrystallization).

Step 2: Preparation of 2-Butyl-3-[(2'-carboxybiphen-4-yl)methyl]-3H-imidazo[4,5-b]pyridine Part A To a stirred suspension of NaH (104 mg of an 80% dispersion, 3.45 mmol) in dry dimethylformamide (8 mL) at room temperature was added 2-butylimidazo[4,5-b]pyridine (504 mg, 2.88 mmol). After 30 minutes, tert-butyl-4'-bromomethylbiphenyl-2-carboxylate (1.0 g, 2.88 mmol) was added in one portion. After 15 hours, the excess NaH was quenched with water (0.5 mL) and the bulk of the DMF was evaporated in vacuo at 40°–50° C. A total of two runs at this scale were combined for the following purification. Extraction with EtOAc (5×20 mL) from brine (5 mL), drying ($K_2CO_3$), concentration, and purification (flash chromatography, $SiO_2$, 100% EtOAc) gave 925 mg (36%) of 2-butyl-3-((2'-tert-butoxycarbonyl)biphen-4-yl)methylimidazo[4,5-b]pyridine as a thick oil: Rf=0.7 ($SiO_2$, 100% EtOAc);

$^1H$ NMR (250 MHz, $CDCl_3$) δ8.36 (dd, 1H, J=4.8, 1.4 Hz), 8.01 (dd, 1H, J=7.9, 1.4 Hz), 7.76 (dd, 1H, J=7.6, 1.9 Hz), 7.52–7.36 (m, 2H) 7.28–7.18 (m, 6H), 5.58 (s, 2H), 2.85 (t, 2H, J=7.6 Hz, 1.92–1.81 (m, 2H), 1.52–1.48 (m, 2H), 1.19 (s, 9H), 0.95 (t, 3H, J=7.3 Hz).

Part B

To a solution of the above tert-butyl ester (820 mg, 1.85 mmol) in methylene chloride (30 mL) at rt was added trifluoroacetic acid (4 mL). After 18 hours, the solution was evaporated (from benzene) and chromatographed (Sephadex-LH-20, MeOH) to give 680 mg (95%) of the title compound as a white solid: mp 181°–183° C. (EtOAc).

$^1H$ NMR (250 MHz, $CDCl_3$) δ8.35 (dd, 1H, J=4.8, 1.1 Hz), 8.05 (dd, 1H, J=8, 1.3 Hz), 7.91 (d, 1H, J=7.3 Hz), 7.54–7.08 (m, 8H), 5.48 (s, 2H), 2.67 (t, 2H, J=7.5 Hz), 1.57–1.42 (m, 2H), 1.21–1.07 (m, 2H), 0.65 (t, 3H, J=7.3 Hz).

EXAMPLE 4

2-Butyl-1-(2'-carboxybiphen-4-yl)methyl-1H-imidazo[4,5-b]pyridine

Part A

The isomer 2-butyl-1-(2'-tert-butoxycarbonylbiphen-4-yl)methyl-1H-imidazo[4,5-b]pyridine was obtained from Part A of Example 3.

Yield: (153 mg, 6%) Rf=0.15 (SiO$_2$, 100% EtOAc, 2 elutions); $^1$H NMR (250 MHz, CDCl$_3$) δ8.50 (dd, 1H, J=5, 1.2 Hz), 7.78 (dd, 1H, J=8.5, 1.5 Hz), 7.54–7.35 (m, 3H), 7.39–7.22 (M, 3H), 7.12–7.02 (m, 3H), 5.39 (s, 2H), 2.92 (t, 2H, J=8 Hz), 1.97–1.84 (m, 2H), 1.53–1.38 (m, 2H), 1.20 (s, 9H), 0.93 (t, 3H, J=7 Hz). The third isomer, 4-(2'-carboxybiphen-4-yl)methyl-2-butyl-4H-imidazo[4,5-b]pyridine (414 mg) was obtained from Part A of Example 3 and was characterized by MS, 1H NMR and NOE.

Part B

The title compound was prepared according to the procedure described in Part B, Example 3.

Yield 85 mg (85%) of an amorphous solid (mp. >260° C.).

EXAMPLE 5

2-Butyl-3-(2'-carboxybiphen-4-yl)methyl-3H-imidazo[4,5-c]pyridine

Step 1: Preparation of 2-butylimidazo[4,5-c]pyridine

The title compound was prepared according to the procedure described for the preparation of 2-butylimidazo[4,5-b]pyridine starting with 3,4-diaminopyridine.

Yield: 3.69 g (92%) thick oil.

$^1$H NMR (300 MHz, CDCl$_3$) δ8.93 (s, 1H), 8.35 (d, 1H, J=6 Hz), 7.48 (d, 1H, J=6 Hz), 3.01 (t, 2H, J=7 Hz), 1.92–1.82 (m, 2H), 1.48–1.30 (m, 2H), 0.86 (t, 3H, J=7 Hz).

Step 2: Preparation of 2-Butyl-3-(2'-carboxybiphen-4-yl)methyl-3H-imidazo[4,5-c]pyridine Part A 2-butyl-3-[(2'-tert-butoxycarbonylbiphen-4-yl)methyl]-2-butyl-3H-imidazo[4,5-c]pyridine was prepared according to the procedure described in Example 1, Part A from 2-butylimidazo[4,5-c]pyridine (220 mg, 1.25 mmol), tert-butyl 4'-bromomethylbiphenyl-2-carboxylate (414 mg, 1.19 mmol), and NaH (1.88 mmol).

Yield: 25 mg (5%) thick oil; Rf: 0.45 (SiO$_2$ tlc, 1% MeOH/EtOAc).

$^1$H NMR (250 MHz, CDCl$_3$) δ8.66 (s, 1H), 8.42 (d, 1H, J=5.6 Hz), 7.78 (dd, 1H, J=7.5, 1.4 Hz), 7.66 (d, 1H, J=5.5 Hz), 7.52–7.35 (m, 2H), 7.31–7.24 (m, 3H), 7.10 (d, 2H, J=8 Hz), 5.46 (s, 2H), 2.92 (t, 2H, J=7.5 Hz), 1.97–1.80 (m, 2H), 1.55–1.39 (m, 2H), 1.21 (s, 9H), 0.96 (t, 3H, J=7.3 Hz).

Part B

The title compound was prepared according to the procedure described in Part B, Example 1.

Yield: 24 mg (104%) of an oil.

$^1$H NMR (300 MHz, CD$_3$OD) δ9.28 (s, 1H), 8.52 (d, 1H, J=5.3 Hz), 8.13 (d, 1H, 5.5 Hz), 7.82 (d, 1H, J=7.5 Hz), 7.56 (t, 1H, 7.5 Hz), 7.46 (t, 1H, 7.5 Hz), 7.40–7.32 (m, 3H), 7.24 (d, 2H, J=7 Hz), 5.73 (s, 2H), 3.05 (t, 2H, J=7 Hz), 1.92–1.78 (m, 2H), 1.54–1.40 (m, 2H), 0.95 (t, 3H, J=7 Hz).

EXAMPLE 6

Preparation of 1-(2'-carboxybiphen-4-yl)methyl-2-butyl-1H-imidazo[4,5-c]pyridine Part A The isomer 1-(2'-tert-butoxycarbonylbiphen-4-yl)methyl-2-butyl-1H-imidazo[4,5-b]pyridine was obtained from Part A of Example 5.

Yield: 32 mg thick oil; Rf=0.40 (SiO$_2$ tlc, 1% MeOH/EtOAc).

$^1$H NMR (250 MHz, CDCl$_3$) δ9.07 (s, 1H), 8.35 (d, 1H, J=5.6 Hz), 7.77 (dd, 1H, J=7.5, 1.3 Hz), 7.51–7.35 (m, 2H), 7.33–7.22 (m, 3H), 7.18 (d, 1H, J=5.6 Hz), 7.06 (d, 2H, J=8 Hz), 5.39 (s, 2H), 2.90 (t, 2H, J=7.5 Hz), 1.93–1.80 (m, 2H), 1.53–1.37 (m, 2H), 1.22 (s, 9H), 0.96 (t, 3H, J=7.2 Hz).

The isomer 5-(2'-tert-butoxycarbonylbiphen-4-yl)methyl-2-butyl-5H-imidazo[4,5-b]pyridine 154 mg) was also obtained from Part A of Example 5 and was characterized by MS, $^1$H NMR and NOE.

Part B

The title compound was prepared according to the procedure described in Part B, Example 3.

Yield: 28 mg of an oil.

$^1$H NMR (300 MHz, CD$_3$OD) δ9.21 (s, 1H), 8.54 (d, 1H, J=6 Hz), 8.31 (d,1H, J=6 Hz), 7.82 (d, 1H, J=7 Hz), 7.55 (t, 1H, J=7 Hz), 7.44 (t, 1H), J=7 Hz), 7.38–7.31 (m, 3H), 7.23 (d, 2H, J=8 Hz), 5.74 (s, 2H) 3.08 (t, 2H, J=7.5 Hz), 1.82–1.78 (m, 2H), 1.53–1.42 (m, 2H), 0.95 (t, 3H, J=7.6 Hz).

EXAMPLE 7

2-Butyl-3-(2'-(tetrazol-5-yl)biphen-4-yl)methyl-3H-imidazo[4,5-b]pyridine

Part A

To a stirred suspension of NaH (102 mg of an 80% dispersion, 3.39 mmol) in dry dimethylformamide (6 mL) at rt was added 2-butylimidazo[4,5-b]pyridine (495 mg, 2.83 mmol) in one portion. After 20 minutes, the mixture was cooled to 0° C. and N-triphenylmethyl-5-(4'-bromomethylbiphenyl-2-yl)tetrazole (1.50 g, 2.70 mmol) was added in one portion. The resulting dark colored mixture was warmed to rt and stirred for 15 hours. The excess NaH was quenched with water (1 mL) and the bulk of the DMF was removed in vacuo at 40°–50° C. Extraction with EtOAc (4×20 mL) from brine (60 mL), drying (K$_2$CO$_3$), and concentration gave a thick dark oil. Purification by flash chromatography (SiO$_2$, solvent gradient: 80% EtOAc/hexanes, 100% EtOAc) gave 417 mg (23%) of 2-butyl-3-(2'-(N-triphenylmethyltetrazol-5-yl)biphen-4-yl)methyl-1H-imidazo[4,5-b]pyridine as a thick oil: Rf=0.75 (SiO$_2$, 100% EtOAc).

$^1$H NMR (300 MHz, CDCl$_3$) δ8.35 (1H, dd, J=6, 1 Hz), 8.05 (1H, dd, J=9, 1 Hz), 7.92 (1H, dd, J=9, 1.5 Hz), 7.51–7.42 (3H, m), 7.36–7.20 (11H, M), 7.07 (2H, d, 7 Hz), 6.96–6.89 (7H, m), 5.40 (2H, s), 2.73 (2H, t, J=7.5 Hz), 1.84–1.70 (2H, m), 1.41–1.30 (2H, m), 0.88 (3H, t, J=7.5 Hz).

Part B

To a stirred solution of the above trityl-protected tetrazole (140 mg, 0.215 mmol) in glacial HOAc (4 mL) at rt was added water (4 mL). The mixture was heated to 80° C. for 2 hours, then stirred for 15 hours at rt. The solvent was removed in vacuo (35° C.) and the residue was chromatographed (SiO₂, 80:20:1 CH₂Cl₂—MeOH—NH₄OH) to give 66 mg (75% of the title compound as an off-white amorphous solid:

¹H NMR (300 MHz, CD₃OD) δ8.33 (1H, dd, J=4.5, 1.5 Hz), 8.00 (1H, dd, J=8, 1.5 Hz) 7.56 (2H, apparent tm, J=8 Hz) 7.47 (2H, apparent tm, J=8H) 7.32 (1H, dd, J=4.5, 8 Hz) 7.07 (apparent singlet, 4H), 5.55 (2H, s), 2.86 (2H, t, J=8 Hz), 1.75-1.63 (2H, m) 1.45-1.32 (2H, m), 0.91 (3H, t, 7.5 Hz).

EXAMPLE 8

Preparation of
2-propyl-3-(2'-(tetrazol-5-yl)biphen-4-yl)methyl-3H-imidazo[4,5-b]pyridine Step 1: Preparation of 2-propylimidazo[4,5-b]pyridine The title compound was prepared according to the procedure described for the preparation of 2-butylimidazo[4,5-b]pyridine starting with 3,4-diaminopyridine and butyric acid. Yield: 6.60 g (89%) amorphous solid.

Step 2: Preparation of 2-propyl-3-(2'-(tetrazol-5-yl)biphen-4-yl)methyl-3H-imidazo[4,5-b]pyridine Part A 2-propyl-3-(2'-(N-triphenylmethyltetrazol-5-yl)-biphen-4-yl)methyl-3H-imidazo[4,5-b]pyridine was prepared according to the procedure described in Example 7, Part A from 2-propylimidazo[4,5-b]pyridine (19 mg, 0.118 mmol), N-triphenylmethyl-5-(4'-bromomethylbiphen-2-yl)tetrazole (60 mg, 0.108 mmol), and NaH (0.236 mmol).

Yield: 18 mg (26%) thick oil; Rf: 0.75 (SiO₂ tlc, 100% EtOAc).

¹H NMR (300 MHz, CDCl₃) δ8.27 (dd, 1H, J=6, 1 Hz), 8.01 (dd, 1H, J=9, 1 Hz), 7.85 (dd, 1H, J=9, 1.5 Hz), 7.50-7.42 (m, 2H), 7.38-7.22 (m, 11H), 7.08 (d, 2H J=7 Hz), 6.98-6.88 (m, 7H), 5.40 (s, 2H), 2.66 (t, 2H, J=7.5 Hz), 1.80-1.65 (m, 2H), 0.93 (t, 3H, J=6 Hz).

Part B

The title compound was prepared according to the procedure described in Example 7, Part B.

Yield: 10 mg (95%) of an amorphous solid.

¹H NMR (300 MHz, CD₃OD) δ8.33 (d, 1H, J=5 Hz), 7.99 (d, 1H, J=8 Hz), 7.58 (t, 2H, J=7.5 Hz), 7.48 (t, 2H, J=7.5 Hz), 7.33 (dd, 1H, J=5, 8 Hz), 7.06 (apparent singlet, 4H), 5.56 (s, 2H), 2.84 (t, 2H, J=8 Hz), 1.83-1.68 (m, 2H), 0.98 (t, 3H, J=6 Hz).

EXAMPLE 9

7-Methyl-2-propyl-3-(2'-(tetrazol-5-yl)biphenyl-4-yl)methyl-7-3H-imidazo[4,5-b]pyridine Step 1: Preparation of 7-methyl-2-propylimidazo[4,5-b]pyridine A mixture of butyric acid (6.57 mL, 71.9 mmol), 2,3-diamino-4-picoline (8.05 g, 65.4 mmol) (Lappin, G. R., Slezak, F. B. *J. Am. Chem. Soc.* (1950) 72, 7806-7) and polyphosphoric acid (50 g) was heated to 100° C. with stirring for 3 hours. The reaction was monitored by tlc of NH₄OH neutralized aliquots. Basification (NH₄OH), extraction (CH₂Cl₂, 4×50 mL), drying (K₂CO₃), purification (by filtering through 100 g SiO₂, EtOAc elution), and concentration gave 10.0 g (95%) of the title compound as an amorphous tan solid which was judged pure by ¹H NMR and tlc: mp 110°-112° C. (without recrystallization).

¹H NMR (300 MHz, CDCl₃) δ8.13 (d, 1H, J=5 Hz), 7.01 (d, 1H, J=5 Hz), 3.01 (t, 2H, J=7.8 Hz), 2.67 (s, 3H), 2.07-1.93 (m, 2H), 1.06 (t, 3H, J=7.5 Hz).

Step 2: 7-methyl-2-propyl-3-(2'-(tetrazol-5-yl)biphen-4-yl)methyl-3H-imidazo[4,5-b]pryidine Part A 3-[2'-(N-triphenylmethyltetrazol-5-yl)biphen-4-yl]methyl-7-methyl-2-propyl-3H-imidazo[4,5-b]pyridine was prepared according to the procedure described in Example 7, Part A from 2-propyl-7-methylimidazo[4,5-b]pyridine (991 mg, 5.66 mmol), N-triphenylmethyl-5-(4'-bromomethylbiphen-2-yl)tetrazole (3.0 g, 5.39 mmol), and NaH (6.47 mmol).

Yield: 1.11 g (32%) thick oil; Rf: 0.80 (SiO₂ tlc, 1:1 EtOAc-hexanes.

¹H NMR (300 MHz, CDCl₃) δ8.20 (d, 1H, J=5 Hz), 7.89 (d, 1H, J=8 Hz), 7.51-7.39 (m, 2H), 7.38-7.20 (m, 10H), 7.10-7.03 (m, 3H), 6.95-6.88, (m, 8H), 5.49 (s, 2H), 2.78-2.68 (m, 2H), 2.69 (s, 3H), 1.83-1.60 (m, 2H), 0.91 (t, 3H, J=5.5 Hz).

Part B

The title compound was prepared according to the procedure described in Example 7, Part B from 1.01 g of the above prepared compound.

Yield: 583 (92%) of an amorphous solid. mp: 195°-197° C. (EtOAc).

¹H NMR (300 MHz, CD₃OD) δ8.16 (d, 1H, J=5 Hz), 7.60-7.38 (m, 4H), 7.12 (d, 1H, J=5 Hz), 7.09 (apparent singlet, 4H), 5.52 (s, 2H), 2.83 (t, 2H, J=5 Hz), 2.64 (s, 3H), 1.79-1.60 (m, 2H), 0.95 (t, 3H, J=5.5 Hz).

Anal. Calcd for C₂₄H₂₃N₇.0.25 H₂O: C, 69.63; H, 5.72; N, 23.68. Found: C, 69.75; H, 5.58; N, 23.69.

Sodium and potassium salts were prepared by combining the product with one equivalent of NaOH or KOH and recrystallization of the resulting salt from the solvent indicated.

7-Methyl-2-propyl-3-(2'-(tetrazol-5-yl)-biphenyl-4-yl)methyl-3H-imidazo[4,5-b]pyridine sodium salt mp: >250° C. (EtOAc); ¹H NMR (300 MHz, CD₃OD) δ8.17 (d, 1H, J=5 Hz), 7.53-7.37 (m,4H), 7.20 (d, 1H, J=5 Hz), 7.08 (d, 2H, J=8.3 Hz), 7.00 (d, 2H, J=8.3 Hz), 5.51 (s, 2H), 2.84 (t, 2H, J=7.5 Hz), 2.65 (s, 3H, 1.79-1.62 (m, 2H), 0.96 (t, 3H, J=7.5 Hz).

7-Methyl-2-propyl-3-(2'-(tetrazol-5-yl)-biphenyl-4-yl)methyl-3H-imidazo[4,5-b]pyridine potassium salt mp: >250° C. (acetone/hexanes); ¹H NMR (300 MHz, CD₃OD) δ8.17 (d, 1H, J=5 Hz), 7.52-7.37 (m, 4H), 7.13 (d, 1H, J-5 Hz), 7.08 (d, 2H, J=8.3 Hz), 6.99 (d, 2H, J=8.3 Hz), 5.51 (s, 2H), 2.84 (t, 2H, J=7.5 Hz), 2.65 (s, 3H), 1.79-1.62 (m, 2H), 0.96 (t, 3H, J=7.5 Hz).

EXAMPLE 10

Preparation of
2-butyl-7-methyl-3-(2'-(tetrazol-5-yl)biphen-4-yl)methyl-3H-imidazo[4,5-b]pyridine Step .1: Preparation of 6-bromo-2-butyl-7-methylimidazo[4,5-b]pyridine The title compound was prepared according to the procedure described for the preparation of 2-butylimidazo[4,5-b]pyridine starting with 5-bromo-2,3-diamino-4-picoline.

Yield: 2.54 g (95%) of an amorphous solid.

¹H NMR (250 MHz, CDCl₃) δ8.45 (s, 1H), 3.05 (t, 2H, J=7 Hz), 2.73 (s, 3H), 2.02-1.87 (m, 2H), 1.61-1.45 (m, 2H), 1.02 (t, 3H, J=7 Hz).

Step 2: Preparation of 2-butyl-7-methylimidazo[4,5-b]pyridine

To a cooled (−78° C.) stirred solution of 6-bromo-2-butyl-7-methylimidazo[4,5-b]pyridine (98 mg, 0.366 mmol) in THF (4 mL) was added tert-butyllithium (0.86 mL of a 1.7M solution in pentane, 1.46 mmol). After 15 minutes, MeOH (0.5 mL and brine were added the mixture was warmed to room temperature and extracted with EtOAc (4×10 mL). Drying ($K_2CO_3$), concentration, and purification ($SiO_2$, 100% EtOAc) gave 60 mg (87%) of the title compound as an oil.

$^1$H NMR (300 MHz, $CDCl_3$) δ8.18 (d, 1H, J=5 Hz), 7.08 (d, 1H, J=5 Hz), 3.05 (t, 2H, J=7.6 Hz), 2.72 (s, 3H), 2.03–1.89 (m, 2H), 1.62–1.43 (m, 2H), 0.96 (t, 3H, J=7.8 Hz).

Step 3: Preparation of 2-butyl-7-methyl-3-(2′-(tetrazol-5-yl)biphen-4-yl)methyl-3H-imidazo[4,5-b]pyridine Part A 2-Butyl-7-methyl-3-(2′-(N-triphenylmethyltetrazol-5-yl)biphen-4-yl)methyl-3H-imidazo[4,5-b]pyridine was prepared according to the procedure described in Example 7, Part A from 2-butyl-7-methylimidazo[4,5-b]pyridine (28 mg, 0.148 mmol), N-triphenylmethyl-5-(4′-bromomethylbiphenyl-2-yl)tetrazole (62 mg, 0.135 mmol), and NaH (0.296 mmol).

Yield: 16 mg (16%) thick oil; Rf: 0.80 ($SiO_2$ tlc, 90% EtOAc/hexanes).

$^1$H NMR (300 MHz, $CDCl_3$) δ8.22 (d, 1H, J=5 Hz), 7.92 (d, 1H, J=8 Hz), 7.54–7.41 (m, 2H), 7.38–7.20 (m, 10H), 7.11–7.04 (m, 3H), 6.97–6.88 (m, 8H), 5.40 (s, 2H), 2.76–2.68 (m, 2H), 2.71 (s, 3H), 1.74–1.63 (m, 2H), 1.42–1.30 (m, 2H), 0.91 (t, 3H, J=5.5 Hz).

Part B

The title compound was prepared according to the procedure described in Example 7, Part B.

Yield: 8.5 mg (89%) of an amorphous solid.

$^1$H NMR (300 MHz, $CD_3OD$) δ8.17 (d, 1H, J=5 Hz), 7.59–7.42 (m, 4H), 7.15 (d, 1H, J=5 Hz), 7.10–7.01 (m, 4H), 5.52 (s, 2H), 2.86 (t, 2H, J=8 Hz), 2.66 (s, 3H), 1.71–1.59 (m, 2H), 1.45–1.30 (m, 2H), 0.90 (t, 3H, J=7 Hz).

EXAMPLE 11

8-Butyl-1,3-dimethyl-7-(2′-(tetrazol-5-yl)biphen-4-yl)methyl-1,2,3,6-tetrahydro-2,6-dioxopurine Step 1: Preparation of 8-Butyl-1,3-dimethyl-1,2,3,6-tetrahydro-2,6-dioxopurine To 3.00 g (17.6 mmol) 5,6-diamino-1,3-dimethyluracil hydrate (Aldrich) in a 50 mL round bottom flask was added 2.31 mL (2.17 g, 21.2 mmol, 1.2 eq) valeric acid and sufficient polyphosphoric acid to make the flask approximately half-full. The viscous mixture was heated at 50°–60° for 14 hours with periodic agitation.

The mixture was cooled, diluted with 30 mL distilled water and the pH adjusted to 8–9 (paper) by the slow addition of concentrated ammonium hydroxide (approx. 20 mL). A tan precipitate formed and was removed by filtration. The filtrate was extracted with chloroform (5×) and the extracts combined with the tan precipitate, dried ($MgSO_4$), filtered and solvents removed in vacuo. The pale yellow residue was chromatographed on silica gel, eluting with ethyl acetate. In this manner, 2.16 g (9.14 mmol, 52%) of the title compound was obtained as a fluffy, white solid.

NMR (300 MHz, DMSO-$d_6$): 0.89 (t, 3H), 1.30 (m, 2H), 1.66 (m, 2H), 2.68 (t, 2H), 3.23 (s, 3H), 3.42 (s, 3H).

FAB-MS: 237 (M+H, 100%).
FAB-MS: 237 (M+H, 100%).

Step 2: Preparation of 8-Butyl-1,3-dimethyl-7-(2′-(tetrazol-5-yl)biphen-4-yl)methyl-1,2,3,6-tetrahydro-2,6-dioxopurine To a solution of 100 mg (0.42 mmol) of purine from Step 1, in 2 mL dry DMF at room temperature was added 20 mg of 60% sodium hydride-oil dispersion (12 mg NaH, 0.50 mmol, 1.2 eq). After 15 minutes, a solution of 226 mg (0.41 mmol, 0.96 eq) N-triphenylmethyl-5-(4′-bromomethylbiphen-2-yl)tetrazole in 1 mL dry DMF was added and the mixture stirred at room temperature 16 hours.

The reaction mixture was added to 30 mL ethyl acetate and washed with 5% aqueous citric acid (2×), saturated aqueous sodium bicarbonate (1×) and brine (1×). The organic layer was separated, dried ($MgSO_4$), filtered and solvents removed in vacuo. The residue was purified by medium pressure liquid chromatography on silica gel, eluting with ethyl acetate/hexane (2:1), to afford 246 mg (0.35 mmol, 82%) of the trityl intermediate as a white solid.

NMR (300 MHz, $CDCl_3$: 0.87 (t, 3H), 1.30 (m, 2H), 1.61 (m, 2H), 2.57 (t, 2H), 3.37 (s, 3H), 3.58 (s, 3H), 5.43 (s, 2H), 6.8–7.8 (several multiplets, 23H).

FAB-MS: 712 (M+H, 1%), 471 (M-trityl, 7%), 243 (trityl, 100%).

The intermediate described above (50 mg, 0.07 mmol) was treated with 2 mL of 50% aqueous acetic at room temperature for 16 hours with vigorous stirring. All volatiles were removed in vacuo, and the residue purified by reverse-phase HPLC on a C18 column eluting with methanol/0.1% aqueous trifluoroacetic acid (linear gradient: 85% MeOH increased to 95% MeOH over 10 minutes). In this manner, 17 mg (0.04 mmol, 57%) of the title compound was obtained as a colorless glass.

NMR (300 MHz, DMSO-$d_6$): 0.81 (t, 3H), 1.26 (m, 2H), 1.50 (m, 2H), 2.66 (t, 2H), 3.23 (s, 3H), 3.42 (s, 3H), 5.58 (s, 2H), 7.07 (d, 2H), 7.13 (d, 2H), 7.5–7.7 (m, 4H).
FAB-MS: 471 (M+H, 100%).

EXAMPLE 12

Preparation of 9-(2′-Carboxybiphen-4-yl)methyl-6-chloro-8-propylpurine

Step 1: 6-Chloro-4,5-diaminopyrimidine

To a cold solution of 5-amino-4,6-dichloropyrimidine (2.0 g, 12.2 mmol) in isopropanol (20 ml) was added liquid ammonia (5 ml), and the mixture was transferred into a sealed tube. The tube was heated at 130° C. for 3 hours and then cooled to room temperature. The product precipitated out was filtered and dried in vacuo. Yield 2.0 g (quantitative).

Step 2: 6-Chloro-8-propylpurine

To a solution of 4,5-diamino-6-chloropyrimidine (0.289 g, 2 mmol) in 2-methoxyethanol (10 ml) were added trimethylorthobutyrate (0.5 ml, 3 mmol) and p-toluenesulfonic acid (0.03 g), and the mixture was refluxed for 18 hours and then concentrated in vacuo. The residue was partitioned between water and and ethylacetate. The organic phase was then washed with brine and dried ($MgSO_4$). The crude product obtained after evaporation of the solvent was purified by flash column chromatography on silica-gel using ethylacetate/hexane (1:1). The fractions containing pure product were pooled and concentrated in vacuo, and then allowed to stand at room temperature overnight. The crystalline product was filtered and dried.

Yield 0.17 g (43%).

NMR (CDCl$_3$): δ1.05 (t, J=9 Hz, 3H), 2.0 (q, 2H), 3.1 (q, 2H), 8.74 (s, 1H); FAB mass-spectra: m/e 197 and 199. (M+H).

Analysis calculated for C$_8$H$_9$N$_4$Cl: C, 48.86; H, 4.61; N, 28.50. Found: C, 49.06; H, 4.76; N, 28.30

Step 3: 6-Chloro-8-propyl-9-(2'-t-butoxycarbonylbiphen-4-yl)methylpurine

To a suspension of NaH (0.20 g) in dry DMF (3 ml), 6-chloro-8-propyl-purine (0.06 g, 0.3 mmol) was added, and the mixture was stirred at 40° C. for 20 minutes. t-Butyl-4-bromomethylbiphenyl-2'-carboxylate (0.11 g, 0.31 mmol) was then added at room temperature and stirring continued for 3 hours at 40° C. The content of the flask was poured into ice-water (100 ml and extracted with ethylacetate. The organic phase was separated and dried over MgSO$_4$. Removal of the solvent under reduced pressure gave the crude product which was then purified by flash-chromatography on silica-gel using ethylacetate-hexane (1:1). The pure titled compound was obtained as a glass-like solid (0.073 g, 53%).

NMR (CDCl$_3$): δ1.04 (t, J=9 Hz, 3H), 1.213 (s, 9H), 1.91 (m, 2H), 2.89 (t, 2H), 5.52 (s, 2H), 7.15-7.52 (m, 7H), 7.79 (dd, J$_1$=8 Hz and J$_2$=2 Hz, 1H), 8.72 (s, 1H); FAB-MS: m/e 463 and 465 (M+H).

Step 4: 6-Chloro-8-propyl-9-(2'-carboxybiphen-4-yl)methylpurine

To a solution of the above t-butyl ester (0.070 g, 0.15 mmol) in methylene chloride (3 ml), anhydrous trifluoracetic acid (2 ml) and anisole (0.02 ml) were added. After stirring for 3 hours at room temperature, the mixture was evaporated to dryness. The crude product was purified by flash-chromatography on silica-gel using chloroform-methanol-NH$_4$OH (40:10:1).

Yield 0.034 g (56%).

NMR(CD$_3$OD): δ0.99 (t, J=9 Hz, 3H), 1.78 (m, 2H), 2.94 (t, 2H), 5.624 (s, 2H), 7.20-7.58 (m, 7H), 7.79 (d, J$_1$=8 Hz, 1H), 8.72 (s, 1H); FAB-MS: m/e 407 and 409 (M+H).

Analysis calculated for C$_{22}$H$_{19}$N$_4$O$_2$Cl.0.25H$_2$O: C, 64.23; H, 4.77; N, 13.62. Found: C, 64.09; H, 4.86; N, 13.27.

EXAMPLE 13

Preparation of 8-Butyl-9-[(2'-carboxybiphen-4-yl)methyl]-6-chloropurine

Step 1: 8-Butyl-6-Chloropurine

A mixture of 6-Chloro-4,5-diaminopyrimidine (0.289 g, 2 mmol) (from Step 1 of Example 12), trimethylorthovalerate (0.52 ml, 3 mmol) and p-TsOH (0.04 g) in 2-methoxyethanol (10 ml) was refluxed for 24 hours. The product was isolated and purified as described in Step 2 of Example 12 to give the crystalline titled compound (0.113 g, 23%).

NMR (CDCl$_3$): δ0.997 (t, J=9 Hz, 3H), 1.484 (m, 2H), 1.925 (m, 2H), 3.075 (m, 2H), 7.27 (s, 1H) and 8.723 (s, 1H).

FAB-MS: m/e 211 and 213 (M+H).

Analysis calculated for C$_9$H$_{11}$N$_4$Cl: C, 51.31; H, 5.26; N, 26.60. Found: C, 51.34; H, 5.30, N, 26.46.

Step 2: 8-Butyl-6-Chloro-9-(2'-t-butoxycarbonylbiphen-4-yl)methylpurine

The titled compound was prepared by the alkylation of 6-chloro-8-butyl purine (0.063 g, 0.3 mmol) with t-Butyl-4-bromomethylbiphenyl-2'-carboxylate (0.104 g, 0.3 mmol) according to the procedure described in Step 3 of Example 12. After flash-chromatographic purification of the crude product using ethyl acetate-hexane (1:1), the product was obtained as a foam (0.085 g, 60%).

NMR (CDCl$_3$): δ0.946 (t, J=9 Hz, 3H), 1.26 (s, 9H), 1.464 (m, 2H), 1.86 (m, 2H), 2.91 (m, 2H), 5.51 (s, 2H), 7.16-7.51 (m, 7H), 7.78 (m, 1H) and 8.723 (s, 1H).

FAB-MS: m/e 477 and 479 (M+H).

Step 3: 8-butyl-6-Chloro-9-(2'-carboxybiphen-4-yl)methylpurine

The t-butyl ester (0.080 g) was deprotected according to the procedure described in Step 4 of Example 12. The pure product was obtained after crystallization from methanol-ether.

Yield 0.030 g (42%).

NMR (CD$_3$OD): δ0.91 (t, J=9 Hz, 3H), 1.41 (m, 2H), 1.76 (m, 2H), 2.98 (m, 2H), 5.63 (s, 2H), 7.2-7.6 (m, 7H), 7.8 (d, J=8 Hz, 2H), 8.715 (s, 1H).

FAB-MS: m/e 421 and 423 (M+H).

Analysis calculated for C$_{23}$H$_{21}$N$_4$O$_2$Cl.0.2H$_2$O: C, 65.07; H, 5.08; N, 13.20. Found: C, 65.23; H, 5.44; N, 12.80.

EXAMPLE 14

Preparation of 8-Butyl-9-(2'-carboxybiphen-4-yl)methyl-6-hydroxypurine

In Step 3 of Example 13, the title compound was isolated as the minor (10%) by product of the reaction. The compound is presumed to arise from the mucleophillic displacement of the 6-chloro function of the purine with water. The structure was confirmed by NMR (CD$_3$OD): δ0.886 (m, 3H), 1.35 (m, 2H), 1.64 (m, 2H), 2.79 (m, 2H), 5.50 (s, 2H), 7.2-7.6 (m, 7H), 7.79 (m, 2H), 8.051 (s, 1H) and mass spectral analysis.

FAB-MS: m/e 403 (M+H).

Analysis calculated for C$_{23}$H$_{22}$N$_4$O$_3$: C, 68.66; H, 5.47; N, 13.93. Found: C, 68.32; H, 5.52; N, 14.07.

EXAMPLE 15

Preparation of 6-Chloro-8-propyl-9-(2'-tetrazol-5-yl)biphen-4-yl)methylpurine

Step 1: 6-Chloro-8-propyl-9-(2'-(N-triphenylmethyltetrazole-5-yl)biphen-4-yl)methylpurine To a stirred suspension of NaH (0.016 g of a 60% dispersion in oil, 0.4 mmol) in dry dimethylformamide (1.5 ml) was added 6-Chloro-8-propylpurine (0.044 g, 0.25 mmol) at room temperature. After 20 minutes, the mixture was cooled to 0° C. and N-triphenylmethyl-5-(4'-bromomethylbiphenyl-2-yl)tetrazole (0.139 g, 0.25 mmol) was added. The resulting mixture was warmed to room temperature and then stirred at 40° C. for 3 hours. The reaction was cooled, and the content of the flask was poured into ice-water (50 ml) and extracted with ethyl acetate (3×15 ml). The combined organic phase was washed with brine and then dried over anhydrous Na$_2$SO$_4$. Removal of the solvent gave the crude product as a foam which was purified by flash-chromatography on silica-gel using ethyl acetate/hexane (1:3).

Yield 0.07 g (foam).

NMR (CDCl$_3$): δ0.96 (t, J=8 Hz, 3H), 1.806 (m, 2H), 2.75 (m, 2H), 5.35 (s, 2H), 6.85-7.54 (m, 22H), 7.85 (m, 1H), 8.72 (s, 1H).

FAB-MS: m/e 674 and 676 (M+H).

Step 2: 6-Chloro-8-propyl-9-(2'-(tetrazol-5-yl)biphen-4-yl)methylpurine

The trityl protected compound (0.065 g) obtained above was dissolved in 50% aqueous acetic acid (2 ml) and the mixture was heated at 50° C. for 15 hours. The solvent was removed in vacuo and residue was purified by flash chromatography on silica-gel using chloroform-methanol-NH$_4$OH (40:10:1) to give pure desired product as a glass like solid (0.016 g).

NMR (CD$_3$OD): δ0.98 (t, J=8 Hz, 3H), 1.754 (m, 2H), 2.89 (m, 2H), 5.57 (s, 2H), 7.135 (q, 4H), 7.5–7.7 (m, 5H), 8.70 (s, 1H).

FAB-MS: m/e 431 and 433 (M+H).

Analysis calculated for C$_{22}$H$_{19}$N$_8$Cl: C, 61.27; H, 4.41; N, 25.99. Found: C, 61.47; H, 4.78; N, 26.32.

EXAMPLE 16

Preparation of
5,7-Dimethyl-2-ethyl-3-(2'-(tetrazol-5-yl)biphen-4-yl)methyl-3H-imidazo[4,5-b]pyridine Step 1: 2-Amino-4,6-dimethyl-3-nitropyridine 2-Amino-4,6-dimethylpyridine (10.0 g, 81.8 mmol) was added portion-wise to 65 mL of H$_2$SO$_4$ (conc. d=1.84) which was stirred (mechanical) at 0° C. After complete addition, the mixture was warmed to room temperature until the mixture became homogeneous. The solution was then cooled to −10° C. and a precooled (0° C.) mixture of concentrated HNO$_3$ (11.5 mL, d=1.40) and H$_2$SO$_4$ (8.2 mL, d=1.84) was added at such a rate as not to raise the internal reaction temperature above −9° C. Ten minutes after the addition was complete this cooled (−10° C.) mixture was poured onto 400 g of crushed ice. The resulting slurry was neutralized by the addition of conc NH$_4$OH (to pH 5.5) while cooling (ice bath). The solid was isolated by filtration, and dried at room temperature to give 13.3 g of 2-nitramino-4,6-dimethylpyridine as a white solid.

To 75 mL of stirred conc H$_2$SO$_4$ cooled to −5° C. (ice-salt bath) was added 4,6-dimethyl-2-nitraminopyridine (13.2 g, 79 mmol) portion-wise at such a rate as to maintain the internal temperature below −3° C. The mixture was warmed to 0° C. until homogeneous (30 minutes) at which time tlc (SiO$_2$, 1:1 EtOAc/hexanes on a NH$_4$OH neutralized aliquot) indicated that the rearrangement was complete. The mixture was poured onto 400 g of crushed ice and the pH was adjusted to 5.5 by the addition of concentrated NH$_4$OH. The resulting yellow slurry was cooled to 0° C., filtered, washed with cold water (50 mL), and dried at room temperature to give 10.32 g of a mixture of the title compound and the 5-nitro isomer in a 55:45 ratio (determined by $^1$H NMR). This mixture was used directly in Step 2.

Step 2: 5,7-Dimethyl-2-ethylimidazo[4,5-b]pyridine

To a mixture of 8.44 g of a 55:45 mixture of 2-Amino-3-nitro-4,6-dimethylpyridine and 2-Amino-4,6-dimethyl-5-nitropyridine in MeOH (1.2 L) was added 10% Pd/C (2.4 g). The reaction vessel was evacuated then purged with H$_2$ at 1 atm. and stirred vigorously for 18 hours. Filtration (celite), and concentration gave 6.65 g of a mixture of 2,3-diamino-4,6-dimethylpyridine and 2,5-diamino-4,6-dimethylpyridine as a dark solid. To 5.40 g (39.4 mmol) of this mixture was added propionic acid (8.80 mL, 118 mmol) followed by polyphosphoric acid (100 mL). This stirred mixture was heated to 90° C. for 3 hours then to 100° C. for 1 hour. After the reaction was complete, the warm mixture was poured onto 300 g of ice and the mixture was made basic with NH$_4$OH.

The mixture was extracted (4×50 mL CH$_2$Cl$_2$), dried (K$_2$CO$_3$) and concentrated to give a mixture of the title compound and 4,6-dimethyl-2,5-bis(propionamido)pyridine. Purification (SiO$_2$, 5% MeOH/EtOAc) gave 1.66 g of the title compound as the slower eluting component.

$^1$H NMR (CD$_3$OD, 300 MHz) δ6.95 (s, 1H), 2.92 (q, 2H, J=7.8 Hz), 2.54 (apparent s, 6H), 1.40 (t, 3H, J=7.8 Hz)

Step 3: 5,7-Dimethyl-2-ethyl-3-(2'-(tetrazol-5-yl)-biphen-4-yl)methyl-3H-imidazo[4,5-b]pyridine Part A 5,7-Dimethyl-2-ethyl-3-(2'-(N-triphenylmethyltetrazol-5-yl)biphen-4-yl)methyl-3H-imidazo[4,5-b]pyridine was prepared according to the procedure described in Example 7, Part A from 5,7-dimethyl-2-ethylimidazo[4,5-b]pyridine (1.51 g, 8.62 mmol), N-triphenylmethyl-5-(4'-bromomethylbiphen-2-yl)tetrazole (5.29 g, 9.48 mmol), and NaH (17.2 mmol).

Yield: 4.25 g white solid.

$^1$H NMR (300 MHz, CDCl$_3$) δ7.86 (dd, 1H, J=7, 2 Hz), 7.50–7.41 (m, 2H), 7.36–7.21 (m, 10H), 7.05 (d, 2H, J=4.5 Hz), 6.95–6.89 (m, 7H), 6.86 (d, 2H, J=4.5 Hz), 5.35 (s, 2H), 2.67 (q, 2H, J=7.5 Hz), 2.65 (s, 3H), 2.58 (s, 3H), 1.25 (t, 3H, J=7.5 Hz).

Part B

To a stirred solution of the tritylprotected tetrazole (4.13 g, 6.33 mmol) in CH$_2$Cl$_2$ (40 mL) at room temperature was added 85% formic acid (60 mL). After 45 minutes, the mixture was concentrated and the residue was purified by chromatography (SiO$_2$, 85:13.5:1.5 CHCl$_3$—MeOH—NH$_4$OH) followed by crystallization from 30 mL of MeOH to give 2.18 g (84%) solid: mp 156°–158° C.

$^1$H NMR (300 MHz, CD$_3$OD) δ7.68–7.61 (m, 2H), 7.57–7.50 (m, 2H), 7.07 (apparent singlet, 4H), 7.04 (s, 1H), 5.55 (s, 2H), 2.85 (q, 2H, J=7.5 Hz), 2.61 (s, 3H), 2.58 (s, 3H), 1.25 (t, 3H, J=7.5 Hz).

Anal. Calcd for C$_{24}$H$_{23}$N$_7$·0.25 H$_2$O: C, 69.63; H, 5.72; N, 23.68. Found: C, 69.91; H, 5.73; N, 23.60.

Another crystalline form (momohydrate, mp 186° C.) was produced when crystallized from 10% water-methanol.

Sodium or potassium salts can be prepared as described in Example 9.

EXAMPLE 17

Preparation of
5,7-Dimethyl-2-propyl-3-(2'-(tetrazol-5-yl)biphen-4-yl)methyl-3H-imidazo[4,5-b]pyridine The title compound was prepared as described in Example 16 using butyric acid in the place of propionic acid in Step 2.

FAB MS, M$^{30}$+1=424.

$^1$H NMR (300 MHz, CD$_3$OD) δ7.67–7.60 (m, 2H), 7.56–7.49 (m, 2H), 7.07 (apparent singlet, 4H), 7.04 (s, 1H), 5.55 (s, 2H), 2.81 (t, 2H, J=7.8 Hz), 2.60 (s, 3H), 2.58 (s, 3H), 1.73–1.60 (m, 2H), 0.95 (t, 3H, J=7.5 Hz).

EXAMPLE 18

Preparation of
2-Butyl-5,7-dimethyl-3-(2'-(tetrazol-5-yl)biphenyl-4-yl)methyl-3H-imidazo[4,5-b]pyridine The title compound was prepared as described in Example 16 using valeric acid in the place of propionic acid in Step 2.

FAB MS, M++1=438.

$^1$H NMR (300 MHz, CD$_3$OD) δ7.67–7.60 (m, 2H), 7.56–7.49 (m, 2H), 7.07 (apparent singlet, 4H), 7.04 (s, 1H), 5.55 (s, 2H), 2.81 (t, 2H, J=7.8 Hz), 2.60 (s, 3H), 2.58 (s, 3H), 1.73–1.60 (m, 2H), 0.95 (t, 3H, J=7.5 Hz).

EXAMPLE 19

Preparation of 3-(2'-Carboxybiphen-4-yl)methyl-5,7-dimethyl-2-ethyl-3H-imidazo[4,5-b]pyridine Part A 3-(2'-tert-Butoxycarbonylbiphen-4-yl)methyl-5,7-dimethyl-2-ethyl-3H-imidazo[4,5-b]pyridine was prepared according to the procedure described in Example 3, Part A from 5,7-dimethyl-2-ethylimidazo[4,5-c]pyridine (50 mg, 0.28 mmol), tert-butyl 4'-bromomethylbiphenyl-2-carboxylate (109 mg, 0.314 mmol), and NaH (0.417 mmol).

Yield: 96 mg thick oil after chromatography (SiO$_2$, 50% EtOAc/hexanes.

FAB MS, M++1=442.

Part B

The title compound was prepared according to the procedure described in Example 3, Part B.

Yield: 80 mg.

FAB MS: M++1=386.

$^1$H NMR (300 MHz, CD$_3$OD) δ7.71 (dd, 1H, J=7.2, 1.2 Hz), 7.52–7.30 (m, 5H), 7.15 (d, 2H, J=8.4 Hz), 7.04 (s, 1H), 5.60 (s, 2H), 2.88 (q, 2H J=7.5 Hz), 2.62 (s, 3H), 2.59 (s, 3H), 1.31 (t, 3H, J=7.5 Hz).

EXAMPLE 20

Preparation of 5-Amino-2-propyl-3-(2'-(tetrazol-5-yl)biphenyl-4-yl)methyl-3H-imidazo[4,5-b]pyridine Step 1: 5-Butyramido-2-propylimidazo[4,5-b]pyridine A mixture of 2,6-diamino-3-nitropyridine (878 mg, 5.7 mmol) and Pd-C (10%, 100 mg) in MeOH (100 mL) was stirred under 1 atm. H$_2$ for 16 hours. The mixture (containing the air sensitive triamine) was filtered, evaporated, and to this flask was added polyphosphoric acid (15 mL) and butyric acid (1.05 mL, 11.5 mmol). This mixture was heated to 80° C. for 5 hours, cooled to room temperature, diluted with water and neutralized with concentrated NH$_4$OH. Extractive workup (CH$_2$Cl$_2$) gave 345 mg of 5-(butyramido)-2-propylimidazo[4,5-b]pyridine.

$^1$H NMR (300 MHz, CDCl$_3$) δ7.94 (d, 1H, J=8.5 Hz), 7.65 (d, 1H, J=8.5 Hz), 2.96 (t, 2H J=7.5 Hz), 2.30 (t, 2H J=7 Hz), 1.98–1.84 (m, 2H), 1.68–1.55 (m, 2H), 0.99 (t, 3H, J=7.5 Hz), 0.80 (t, 3H, J=7.0 Hz).

Step 2: 5-amino-2-propylimidazo[4,5-b]pyridine

A mixture of 5-butyramido-2-propylimidazo[4,5-b]pyridine (250 mg, 1.07 mmol), MeOH (20 mL), and concentrated aqueous HCl (2 mL) was heated to 45° C. for 16 hours. Concentration and neutralization with NaHCO$_3$ gave 150 mg of the title compound as a glass.

$^1$H NMR (300 MHz, CD$_3$OD) δ7.57 (d, 1H, J=8.5 Hz), 6.46 (d, 1H, J=8.5 Hz), 2.76 (t, 2H, J=7.5 Hz), 1.85–1.70 (m, 2H), 0.93 (t, 3H, J=7.5 Hz).

Step 3: 5-amino-2-propyl-3-(2'-(tetrazol-5-yl)biphen-4-yl)methyl-3H-imidazo[4,5-b]pyridine Part A 5-amino-2-propyl-3-(2'-(N-triphenylmethyltetrazol-5-yl)biphen-4-yl)methyl-3H-imidazo[4,5-b]pyridine was prepared according to the procedure described in Example 7, Part A from 5-amino-2-propylimidazo[4,5-b]pyridine (130 mg, 0.80 mmol), N-triphenylmethyl-5-(4'-bromomethylbiphen-2-yl)tetrazole (445 mg, 0.800 mmol), and NaH (2.4 mmol).

Yield: 185 mg (as a glass like solid).

Part B

A mixture of the triphenymethyl tetrazolate described in Part A (80 mg, 0.122 mmol), concentrated aqueous HCl (1 mL), in methanol (10 mL) was stirred for 16 h at room temperature. Concentration and purification (SiO$_2$, 80:19:1 CH$_2$Cl$_2$:MeOH:NH$_4$OH) gave 50 mg of the title compound as a white solid.

FAB MS M++1=411.

$^1$H NMR (300 MHz, CD$_3$OD) δ7.67 (d, 1H, J=8.7 Hz), 7.61–7.55 (m, 2H), 7.51–7.43 (m, 2H), 7.07 (apparent s, 4H), 6.58 (d, 1H, J=8.7 Hz), 5.42 (s, 2H), 2.76 (t, 2H J=7.5 Hz), 1.73–1.60 (d, 2H), 0.93 (t, 3H, J=7.2 Hz).

EXAMPLE 21

Preparation of 2-ethyl-7-methyl-3-(2'-(tetrazol-5-yl)biphen-4-yl)methyl-3H-imidazo[4,5-b]pyridine Step 1: 2-Ethyl-7-methylimidazo[4,5-b]pyridine A mixture of propionic acid (0.89 ml, 12 mmols), 2,3-diamino-4-picoline (1.23 g, 10 mmol) and polyphosphoric acid (40 g) was heated to 100° C. for 6 hours. Work-up of the reaction and purification of the crude product according to the procedure described in Step 1 of Example 9 gave the desired compound (1.46 g, 90%) as a tan colored solid.

$^1$H NMR (300 MHz, CDCl$_3$): 8.14 (d, 1H, J=5 Hz), 7.01 (d, 1H, J=5 Hz), 3.02 (q, 2H, J=7.8 Hz), 2.69 (s, 3H), 1.45 (t, 3H, J=7.8 Hz).

Step 2: 2-Ethyl-7-methyl-3-(2'-tetrazol-5-yl)biphen-4-yl)methyl-3H-imidazo[4,5-b]pyridine Part A:

2-Ethyl-7-methyl-3(2'-(N-triphenylmethyltetrazol-5-yl)biphen-4-yl)methyl-3H-imidazo[4,5-b]pyridine was prepared according to the procedure described in Part A of Example 7, from 2-ethyl-7-methylimidazo[4,5-b]pyridine (0.5 g, 3.11 mmol), N-triphenylmethyl-5-(4'-bromomethylbiphenyl-2-yl)tetrazole (1.82 g, 3.26 mmol) and NaH (3.12 mmol). The crude product (1.9 g, foam) was purified by flash chromatography on silicagel using EtOAc-hexanees (1:1.5) to give the desired product as a white solid (0.95 g, 47.5%).

$^1$H NMR (300 MHz, CDCl$_3$): 8.2 (d, 1H, J=5 Hz), 7.9 (d, 1H, J=8 Hz), 6.80–7.55 (m, 23H), 5.4 (s, 2H), 2.58–2.85 (m, 5H), 1.25 (t, 3H, J=7.8 Hz).

Part B:

The title compound was prepared from the above compound (0.42 g) according to the procedure described in Part B of Example 7. Yield: 0.26 g (99%). The material was finally crystallized from methanol-ether to give white crystalline product (0.24 g). mp: 192°–193° C.

$^1$H NMR (300 MHz, CD$_3$OD): 8.2 (d, 1H, J=5 Hz), 7.4–7.62 (m, 4H), 6.96–7.45 (m, 5H), 5.52 (s, 2H), 2.88 (q, 2H, J=7.8 Hz), 2.65 (s, 3H), 1.27 (t, 3H, J=7.8 Hz).

Anal. Calcd. for C$_{23}$H$_{21}$N$_7$. 0.5 H$_2$O: C, 68.32; H, 5.45; N, 24.26. Found: C, 68.59; H, 5.73; N, 24.12.

EXAMPLE 22

Preparation of
2,7-dimethyl-3-(2'-(tetrazol-5-yl)biphen-4-yl)methyl-3H-imidazo[4,5-b]pyridine Step 1: 2,7-Dimethylimidazo[4,5-b]pyridine The title compound was prepared from 2,3-diamino-4-picoline (0.246 g, 2 mmol) and acetic acid (0.15 ml) according to the procedure described in Step 1 of Example 9. The crude product was purified by flash chromatography on silica-gel using EtOAc-MeOH (9:1) to give the pure product (0.25 g, 85%) as a light brown solid.

$^1$H NMR (300 MHz, CDCl$_3$): 8.14 (d, 1H, J=5 Hz), 7.01 (d, 1H, J=5 Hz), 2.73 (s, 3H), 2.62 (s, 3H).

Step 2: 2,7-Dimethyl-3-(2'-(tetrazol-5-yl)biphen-4-yl)methyl-3H-imidazo[4,5-b]pyridine The titled compound was prepared from the above compound according to the procedures described in Part A and Part B of Example 5. The pure desired product was obtained as a white amorphous powder.

$^1$H NMR (300 MHz, CD$_3$OD): 8.12 (d, 1H, J=5 Hz), 7.45–7.65 (m, 4H), 6.96–7.4 (m, 5H), 5.52 (s, 2H), 2.65 (s, 3H), 2.52 (s, 3H).

Anal. Calcd. for C$_{22}$H$_{19}$N$_7$.H$_2$O: C, 77.19; H, 5.26; N, 24,56. Found: C, 76.91; H, 5.73; N, 24.33.

EXAMPLE 23

Preparation of
7-Methyl-2-pentyl-3-(2'-(tetrazol-5-yl)biphen-4-yl)methyl-3H-imidazo[4,5-b]pyridine Step 1: 7-Methyl-2-pentyl-imidazo[4,5-b]pyridine The title compound was prepared from 2,3-diamino-4-picoline (0.246 g, 2 mmol) and hexanoic acid (0.25 ml, 2 mmols) according to the procedure described in Step 1 of Example 9. The crude product was purified by flash chromatography on silica-gel using EtOAc-MeOH (9:1) to give the pure product (0.28 g, 69%) as a tan colored solid.

$^1$H NMR (300 MHz, CDCl$_3$): 8.17 (d, 1H, J=5 Hz), 7.05 (d, 1H, J=5 Hz), 3.03 (t, 2H, J=7.8 Hz), 2.70 (s, 3H), 1.32–2.1 (m, 6H), 0.92 (t, 3H, J=7.8 Hz).

Step 2: 7-Methyl-2-pentyl-3-(2'-(tetrazol-5-yl)biphen-4-yl)methyl-3H-imidazo[4,5-b]pyridine The titled compound was prepared from the above compound according to the procedures described in Part A and Part B of Example 7. The pure desired product was obtained as a white amorphous powder (R$_f$ 0.45 in CHCl$_3$-MeOH-NH$_4$OH 40:10:1).

$^1$H NMR (300 MHz, CD$_3$OD): 8.20 (d, 1H, J=5 Hz), 7.48–7.80 (m, 4H), 7.01–7.3 (m, 5H), 5.72 (s, 2H), 2.84 (t, 2H, J=7.8 Hz), 2.65 (s, 3H), 1.68 (m, 2H), 1.32 (m, 4H), 0.9 (t, 3H, J=7.8 Hz).

FAB-MS: m/e 438 (M+H).

EXAMPLE 24

Preparation of
7-methyl-2-nonyl-3-(2'-(tetrazol-5-yl)biphen-4-yl)methyl-3H-imidazo[4,5-b]pyridine Step 1: 7-Methyl-2-nonylimidazo[4,5-b]pyridine The title compound was prepared from 2,3-diamino-4-picoline (0.246 g, 2 mmol) and decanoic acid (0.35 g, 2 mmol) according to the procedure described in Step 1 of Example 9. The crude product was purified by flash chromatography on silica-gel using EtOAc-MeOH (20:1) to give the pure product (0.38 g, 72%) as a tan colored solid.

$^1$H NMR (300 MHz, CDCl$_3$): 8.16 (d, 1H, J=5 Hz), 7.05 (d, 1H, J=5 Hz), 3.03 (t, 2H, J=7.8 Hz), 2.69 (s, 3H), 1.25–2.0 (m, 14H), 0.90 (t, 3H, J=7.8 Hz).

Step 2: 7-methyl-2-nonyl-3-(2'-(tetrazol-5-yl)biphen-4-yl)methyl-3H-imidazo[4,5-b]pyridine The titled compound was prepared from the above compound according to the procedures described in Part A and Part B of Example 7. The pure desired product was obtained as a cream colored amorphous powder (R$_f$ 0.5 in CHCl$_3$-MeOH-NH$_4$OH 40:10:1).

$^1$H NMR (300 MHz, CD$_3$OD): 8.20 (d, 1H, J=5 Hz), 7.48–7.70 (m, 4H), 7.08–7.3 (m, 5H), 5.58 (s, 2H), 2.84 (t, 2H, J=7.8 Hz), 2.64 (s, 3H), 1.68 (m, 2H), 1.1–1.4 (m, 12H), 0.89 (t, 3H, J=7.8 Hz).

FAB-MS: m/e 494 (M+H).

EXAMPLE 25

Preparation of
2-Isopropyl-7-methyl-3-(2'-(tetrazol-5-yl)biphen-4-yl)methyl-3H-imidazo[4,5-b]pyridine Step 1: 2-Isopropyl-7-methylimidazo[4,5-b]pyridine The title compound was prepared from 2,3-diamino-4-picoline (0.246 g, 2 mmol) and isobutyric acid (0.19 ml, 2 mmol) according to the procedure described in Step 1 of Example 9. The crude product was purified by flash chromatography on silica-gel using EtOAc-MeOH (20:1) to give the pure product (0.25 g, 72%) as a tan colored solid.

$^1$H NMR (300 MHz, CDCl$_3$): 8.21 (d, 1H, J=5 Hz), 7.05 (d, 1H, J=5 Hz), 3.40 (m, 1H), 2.71 (s, 3H), 1.55 (d, 6H, J=7 Hz).

FAB-MS: m/e 176 (M+H).

Step 2: 2-Isopropyl-7-methyl-3-(2'-(tetrazol-5-yl)biphen-4-yl)methyl-3H-imidazo[4,5-b]pyridine The titled compound was prepared from the above compound according to the procedures described in Part A and Part B of Example 7. The pure desired product was obtained as a cream colored amorphous powder (R$_f$ 0.45 in CHCl$_3$-MeOH-NH$_4$OH 40:10:1).

$^1$H NMR (300 MHz, CD$_3$OD): 8.20 (d, 1H, J=5 Hz), 7.50–7.70 (m, 4H), 7.08–7.2 (m, 5H), 5.6 (s, 2H), 3.3 (m, 1H), 2.68 (s, 3H), 1.3 (d, 6H, J=7 Hz).

FAB-MS: m/e 410 (M+H).

EXAMPLE 26

Preparation of
7-Methyl-2-(3-methyl)propyl-3-(2'-(tetrazol-5-yl)-biphen-4-yl)methyl-3H-imidazo[4,5-b]pyridine Step 1: 7-Methyl-2-(3-methyl)propyl)imidazo[4,5-b]pyridine The title compound was prepared from 2,3-diamino-4-picoline (0.246 g, 2 mmol) and 3-methylbutyric acid (0.22 ml, 2 mmol) according to the procedure described in Step 1 of Example 9. The crude product was purified by flash chromatography on silica-gel using EtOAc-MeOH (20:1) to give the pure product (0.30 g, 78%) as a tan colored solid.

$^1$H NMR (300 MHz, CDCl$_3$): 8.20 (d, 1H, J=5 Hz), 7.05 (d, 1H, J=5 Hz), 2.90 (d, 2H, J=7 Hz), 2.70 (s, 3H), 2.32 (m, 1H), 1.11 (d, 6H, J=7 Hz).

FAB-MS: m/e 190 (M+H).

Step 2: 7-methyl-2-(3-methyl)propyl-3-(2'-(tetrazol-5-yl)biphenyl-4-yl)methyl-3H-imidazo[4,5-b]pyridine The titled compound was prepared from the above compound according to the procedures described in Part A and Part B of Example 7. The pure desired product was obtained as a cream colored amorphous powder.

$^1$H NMR (300 MHz, CD$_3$OD): 8.20 (d, 1H, J=5 Hz), 7.50–7.70 (m, 4H), 7.08–7.2 (m, 5H), 5.6 (s, 2H), 2.75 (d, 2H, J=7 Hz), 2.68 (s, 3H), 2.1 (m, 1H), 0.92 (d, 6H, J=7 Hz).

FAB-MS: m/e 424 (M+H).

EXAMPLE 27

Preparation of 2-Cyclopropyl-7-methyl-3-(2'-(tetrazol-5-yl)biphen-4-yl)methyl-3H-imidazo[4,5-b]pyridine The title compound was prepared as described in Example 9 using cyclopropane carboxylic acid in place of butyric acid in Step 1.

$^1$H NMR (300 MHz, CD$_3$OD): 8.14 (d, 1H, J=5 Hz), 7.50–7.70 (m, 4H), 7.08–7.2 (m, 5H), 5.64 (s, 2H), 2.61 (s, 3H), 2.12 (m, 1H), 1.11 (m, 4H).

FAB-MS: m/e 408 (M+H).

EXAMPLE 28

Preparation of 2-Methoxymethyl-7-methyl-3-(2'-(tetrazol-5-yl)biphen-4-yl)methyl-3H-imidazo[4,5-b]pyridine Step 1: 2-Methoxymethyl-7-methylimidazo[4,5-b]pyridine A mixture of 2,3-diamino-4-picoline (0.1 g, 0.81 mmol) and methoxyacetic acid (0.16 ml, 2 mmol) was heated in a sealed tube at 165° C. for 24 hours. The reaction was cooled and neutralized with NH$_4$OH. The crude material was dissolved in methanol (2 ml) and silica-gel (10 g) was added. The dried silica-gel was then loaded on a silica-gel flash-column and eluted initially with EtOAc and then with 2% methanol in EtOAc. The pure desired compound was obtained as a cream colored solid (0.067 g, 47%).

$^1$H-NMR (CDCl$_3$): 8.27 (d, 1H, J=5 Hz), 7.07 (d, 1H, J=5 Hz), 4.86 (s, 2H), 3.57 (s, 3H), 2.7 (s, 3H).

FAB-MS: m/e 178 (M+H).

Step 2: 2-Methoxymethyl-7-methyl-3-(2'-(tetrazol-5-yl)biphen-4-yl)methyl-3H-imidazo[4,5-b]pyridine The title compound was prepared from the compound described in Step 1 as described in Step 2 of Example 9.

$^1$H NMR (300 MHz, CD$_3$OD): 8.26 (d, 1H, J=5 Hz), 7.50–7.71 (m, 4H), 7.05–7.26 (m, 5H), 5.61 (s, 2H), 4.64 (s, 2H), 3.32 (s, 3H), 2.67 (s, 3H).

FAB-MS: m/e 412 (M+H).

EXAMPLE 29

Preparation of 8-Propyl-9-(2'-(tetrazol-5-yl)biphen-4-yl)methylpurine

6-Chloro-8-propyl-9-(2'-(tetrazol-5-yl)biphen-4-yl)methylpurine (0.030 g) was dissolved in ethanol (2 ml) and was stirred under an atmosphere of hydrogen in presence of Pd-C(10%) (0.01 g) for 24 hours. The catalyst was filtered off and the filtrate was evaporated to dryness giving the pure desired product as a glass like solid (0.020 g).

NMR(CD$_3$OD): δ1.0 (t, 3H, J=7.4 Hz), 1.8 (m, 2H), 2.88 (t, 2H, J=7.4 Hz), 5.56 (s, 2H), 7.1–7.34 (m, 5H), 7.45–7.7 (m, 4H), 8.90 (s, 1H), 8.98 (s, 1H).

FAB-MS: m/e 397 (M+H).

Analysis calculated for C$_{22}$H$_{20}$N$_8$: C, 66.00; H, 5.00; N, 28.00. Found: C, 65.57; H, 5.34; N, 27.67.

EXAMPLE 30

Preparation of 8-Butyl-6-chloro-9-(2'-(tetrazol-5-yl)biphen-4-yl)methylpurine The titled compound was prepared from 8-butyl-6-chloropurine according to the procedures described in Example 15.

NMR(CD$_3$OD): δ0.92 (t, J=8 Hz, 3H), 1.42 (m, 2H), 1.75 (m, 2H), 2.92 (m, 2H), 5.58 (s, 2H), 7.14 (m, 4H), 7.5–7.7 (m, 5H), 8.72 (s, 1H).

FAB-MS: m/e 445 and 447 (M+H).

Analysis calculated for C$_{23}$H$_{21}$N$_8$Cl: C, 62.09; H, 4.72; N, 25.20. Found: C, 61.79; H, 4.95; N, 25.32.

EXAMPLE 31

Preparation of 8-Butyl-9-(2'-(tetrazol-5-yl)biphen-4-yl)methylpurine

The titled compound was prepared from 8-Butyl-6-chloro-9-(2'-(tetrazol-5-yl)biphen-4-yl)methyl-purine as described in Example 29.

NMR (CD$_3$OD): δ0.99 (t, 3H, J=7.4 Hz), 1.30 (m, 2H), 1.78 (m, 2H), 2.88 (t, 2H, J=7.4 Hz), 5.55 (s, 2H), 7.1–7.3 (m, 5H), 7.45–7.63 (m, 4H), 8.90 (s, 1H), 8.98 (s, 1H).

FAB-MS: m/e 411 (M+H).

Analysis calculated for C$_{23}$H$_{22}$N$_8$: C, 67.32; H, 5.37; N, 27.32. Found: C, 67.76; H, 5.54; N, 27.67.

EXAMPLE 32

Preparation of 2-Chloro-6-methyl-8-propyl-9-(2'-(tetrazol-5-yl)biphen-4-yl)methylpurine Step 1: 2-Chloro-6-methyl-8-propylpurine A mixture of 2-Chloro-4,5-diamino-6-methylpyrimidine (0.80 g, 5.04 mmol), trimethylorthobutyrate (1.2 ml, 7.6 mmol) and p-TsOH (0.08 g) in 2-methoxyethanol (24 ml) was heated in an oil bath at 140° C. for 24 hours. The product was isolated as described in Step 2 of Example 12 and purified by flash chromatography using EtOAc-hexane (1:1) to give the crystalline titled compound (0.5 g, 47%).

NMR(CDCl$_3$): δ1.03 (t, J=8 Hz, 3H), 1.9 (q, 2H), 2.82 (s, 3H), 3.0 (t, J=8 Hz, 2H).

FAB-MS: m/e 211 and 213 (M+H).

Analysis calculated for C$_9$H$_{11}$N$_4$Cl: C, 51.31; H, 5.26; N, 26.60. Found: C, 51.43; H, 5.50, N, 26.81.

Step 2: 2-Chloro-6-methyl-8-propyl-9-(2'-(tetrazol-5-yl)-biphen-4-yl)methylpurine The titled compound was prepared from 2-Chloro-6-methyl-8-propylpurine (from Step 1) according to the procedure described in Example 15.

NMR(CD$_3$OD): δ0.97 (t, J=8 Hz, 3H), 1.73 (q, 2H), 2.77 (s, 3H), 2.82 (t, J=8 Hz, 2H), 5.52 (s, 2H), 7.1–7.3 (m, 4H), 7.5–7.75 (m, 5H).

FAB-MS: m/e 445 and 447 (M+H).

Analysis calculated for C$_{23}$H$_{21}$N$_8$Cl: C, 62.09; H, 4.72; N, 25.20. Found: C, 61.79; H, 4.95; N, 25.32.

EXAMPLE 33

Preparation of 2-Dimethylamino-6-methyl-8-propyl-9-(2'-(tetrazol-5-yl)-biphen-4-yl)methylpurine Step 1: 2-Dimethylamino-6-methyl-8-propylpurine To a solution of 2-Chloro-6-methyl-8-propylpurine (from Step 1 of Example 32) (0.1 g, 0.47 mmol) in ethanol (2 ml) was added condensed dimethylamine (1 ml) at 0° C. The mixture was then placed in a steel-bomb and heated at 110° C. for 7 hours. The reaction was cooled and the mixture was concentrated in vacuo. The residue was partitioned between CHCl$_3$ and water, and the organic was separated and dried over MgSO$_4$. The crude product obtained after removal of the solvent was purified by flash-chromatography on silica-gel using 5% MeOH in CHCl$_3$ giving the titled compound as an amorphous solid (0.065 g, 64%).

NMR(CDCl$_3$): δ1.01 (t, J=8 Hz, 3H), 1.8 (q, J=8 Hz, 2H), 2.65 (s, 3H), 2.8 (t, J=8 Hz, 2H), 3.2 (s, 6H).

FAB-MS: m/e 220 (M+H).

Step 2: 2-Dimethylamino-6-methyl-8-propyl-9-(2'-(tetrazol-5-yl)-biphen-4-yl)methylpurine The title compound was prepared from 2-Dimethylamino-6-methyl-8-propylpurine (from Step 1) according to the procedures described in Example 15.

NMR(CD$_3$OD): δ0.95 (t, J=8 Hz, 3H), 1.66 (q, J=8 Hz, 2H), 2.61 (s, 3H), 2.75 (t, J=8 Hz, 2H), 3.2 (s, 6H), 5.36 (s, 2H), 7.07–7.23 (m, 4H), 7.5–7.7 (m, 5H).

FAB-MS: m/e 454 (M+H) and 476 (M+Na).

EXAMPLE 34

Preparation of 6-Methyl-2-methylamino-8-propyl-9-(2'-(tetrazol-5-yl)biphen-4-yl)methylpurine Step 1: 6-Methyl-2-methylamino-8-propylpurine To a solution of 2-Chloro-6-methyl-8-propylpurine (from Step 1 of Example 32) (0.1 g, 0.47 mmol) in ethanol (2 ml) was added condensed methylamine (1 ml) at −20° C. The mixture was then placed in a steel-bomb and heated at 110° C. for 7 hours. The reaction was cooled and the mixture was concentrated in vacuo. The residue was partitioned between CHCl$_3$ and water, and the organic layer was separated and dried over MgSO$_4$. The crude product obtained after removal of the solvent was purified by flash-chromatography on silica-gel using 5% MeOH in CHCl$_3$ giving the titled compound as an amorphous solid (0.115 g, quantitative).

NMR(CDCl$_3$): δ1.03 (t, J=8 Hz, 3H), 1.8 (q, J=8 Hz, 2H), 2.64 (s, 3H), 2.8 (t, J=8 Hz, 2H), 3.0 (d, J=5 Hz, 3H), 5.1 (br s, 1H).

FAB-MS: m/e 206 (M+H).

Step 2: 6-Methyl-2-methylamino-8-propyl-9-(2'-(tetrazol-5-yl)biphen-4-yl)methylpurine The titled compound was prepared from 6-Methyl-2-methylamino-8-propylpurine (from Step 1) according to the procedures described in Example 15.

NMR(CD$_3$OD): δ0.90 (t, J=8 Hz, 3H), 1.62 (q, J=8 Hz, 2H), 2.5 (s, 3H), 2.65 (t, J=8 Hz, 2H), 2.88 (s, 3H), 5.26 (s, 2H), 7.02 (s, 4H), 7.3–7.5 (m, 5H).

FAB-MS: m/e 440 (M+H).

EXAMPLE 35

Preparation of 6-Methyl-2-(morpholin-4-yl)-8-propyl-9-(2'-(tetrazol-5-yl)biphen-4-yl)methylpurine Step 1: 6-Methyl-2-(morpholin-4-yl)-8-propylpurine A solution of 2-Chloro-6-methyl-8-propylpurine (from Step 1 of Example 32) (0.1 g, 0.47 mmol) in morpholine (2 ml) was placed in a steel-bomb, and the mixture was heated at 122° C. for 18 hours. The reaction was cooled, and the mixture was concentrated in vacuo. The residue was dissolved in CHCl$_3$ (2 ml) and was purified by flash-chromatography on silica-gel using 5% MeOH in CHCl$_3$ giving the titled compound as an amorphous solid (0.1 g, 87%).

NMR(CDCl$_3$): δ1.03 (t, J=8 Hz, 3H), 1.8 (q, J=8 Hz, 2H), 2.65 (s, 3H), 2.82 (t, J=8 Hz, 2H), 3.8 (s, 8H).

FAB-MS: m/e 262 (M+H).

Step 2: 6-Methyl-2-(morpholin-4-yl)-8-propyl-9-(2'-(tetrazol-5-yl)biphen-4-yl)methylpurine The titled compound was prepared from 6-Methyl-2-(N-morpholino)-8-propylpurine (from Step 1) according to the procedures described in Example 15.

NMR(CD$_3$OD): δ0.90 (t, J=8 Hz, 3H), 1.62 (q, J=8 Hz, 2H), 2.54 (s, 3H), 2.68 (t, J=8 Hz, 2H), 3.7 (m, 8H), 5.29 (s, 2H), 7.05 (m, 4H), 7.4–7.6 (m, 5H).

FAB-MS: m/e 496 (M+H).

EXAMPLE 36

Preparation of 3-(2'-carboxybiphen-4-yl)methyl-7-methyl-2-propyl-3H-imidazo[4,5-b]pyridine 7-Methyl-2-propylimidazo[4,5-b]pyridine (described in Example 9) was alkylated with 2-t-butoxycarbonyl-4'-bromomethylbiphenyl and the resulting protected derivatives was deprotected according to the procedure described in Step 2 of Example 3.

NMR (CDCl$_3$): δ0.93 (t, J=7.5 Hz, 3H), 1.69 (q, 2H), 2.63 (s, 3H), 2.78 (t, J=7.5 Hz, 2H), 5.49 (s, 3H), 7.04–7.5 (m, 8H), 7.8 (d, J=2.4 Hz, 1H), 8.14 (d, J=5 Hz, 1H).

FAB-MS: m/e 386 (M+H).

EXAMPLE 37

Preparation of 7-Methyl-3-(2'-(N-(phenylsulfonyl)carboxamidobiphen-4-yl)methyl-2-propyl-3H-imidazo[4,5-b]pyridine To a suspension of 3-(2'-carboxybiphen-4-yl)methyl-7-methyl-2-propyl-3H-imidazo[4,5-b]pyridine (0.1 g, 0.26 mmol) in dry THF (5 ml) was added 1,1'-carbonyldiimidazole (0.042 g, 0.26 mmol), and the mixture was refluxed for 3 hours and then cooled to room temperature. Benzenesulfonamide (0.05 g, 0.33 mmol) and DBU (0.49 ml, 0.33 mmol) were added and the mixture was stirred at 40° C. for 7 hours. The reaction was cooled and concentrated in vacuo. The residue was dissolved in water (5 ml) and acidified with 10% aqueous NaH$_2$PO$_4$ to pH 5 and extracted with EtOAc (3×20 ml). The combined organic phase was dried over MgSO$_4$ and concentrated in vacuo to give the crude product, which was then purified by flash-chromatography on silica-gel using 2% MeOH in EtOAc to give the desired product as white amorphous solid (0.087 g, 64%).

NMR (CDCl$_3$): δ1.0 (t, J=7.5 Hz, 3H), 1.8 (q, 2H), 2.7 (s, 3H), 2.78 (t, J=7.5 Hz, 2H), 5.50 (s, 3H), 6.8–7.8 (m, 14H), 8.2 (d, J=5 Hz, 1H).

FAB-MS: m/e 525 (M+H).

EXAMPLE 38

Preparation of 3-(2'-(N-(4-(Chloro)phenylsulfonylcarboxamido)biphen-4-yl)methyl-7-methyl-2-propyl-3H-imidazo[4,5-b]pyridine The title compound was prepared from 3-(2'-carboxybiphen-4-yl)methyl-7-methyl-2-propyl-3H-imidazo[4,5-b]pyridine and p-chlorobenzenesulfonamide according to the procedure described in Example 37.

NMR (CD$_3$OD): δ0.99 (t, J=7.5 Hz, 3H), 1.76 (m, 2H), 2.69 (s, 3H), 2.87 (t, J=7.5 Hz, 2H), 5.60 (s, 3H), 6.95 (d, J=8 Hz, 2H), 7.1-7.8 (m, 11H), 8.25 (d, J=5 Hz, 1H).

FAB-MS: m/e 559 and 561 (M+H).

Analysis calculated for C$_{30}$H$_{27}$N$_4$O$_3$ClS: C, 64.46; H, 4.83; N, 10.03. Found: C, 64.78; H, 5.07; N, 10.26.

EXAMPLE 39

Preparation of 3-(2'-(Methylsulfonylcarboxamido)biphen-4-yl)methyl-7-methyl-2-propyl-3H-imidazo[4,5-b]pyridine To a suspension of 3-(2'-carboxybiphenyl-4-yl)methyl-7-methyl-2-propyl-3H-imidazo[4,5-b]pyridine (0.1 g, 0.26 mmol) in dry THF (5 ml) was added 1,1'-carbonyldiimidazole (0.042 g, 0.26 mmol), and the mixture was refluxed for 3 hours and then cooled to room temperature. A solution of sodium salt of Methanesulfonamide [prepared from methanesulfonamide (0.036 g, 0.39 mmol) and NaH (0.39 mmol) in DMF (1.5 ml) at 40° C.] was then added, and the mixture was stirred at 40° C. for 8 hours. The reaction was cooled and concentrated in vacuo. The residue was dissolved in water (5 ml) and acidified with 10% aqueous NaH$_2$PO$_4$ to pH 5 and extracted with EtOAC (3×20 ml). The combined organic phase was dried over MgSO$_4$ and concentrated in vacuo to give the crude product, which was then purified by flash-chromatography on silica-gel using 2% MeOH in EtOAc to give the desired product as white amorphous solid (0.05 g, 42%).

NMR (CD$_3$OD): δ0.99 (t, J=7.5 Hz, 3H), 1.77 (m, 2H), 2.67 (s, 3H), 2.90 (t, J=7.5 Hz, 2H), 2.98 (s, 3H), 5.62 (s, 3H), 7.14-7.27 (m, 3H), 7.37-7.6 (m, 6H), 8.2 (d, J=5 Hz, 1H).

FAB-MS: m/e 463 (M+H).

EXAMPLE 40

Preparation of 2-Cyclopropyl-5,7-dimethyl-3-(2'-(tetrazol-5-yl)biphen-4-yl)methyl-3H-imidazo[4,5-b]pyridine The title compound was prepared as described in Example 16 using cyclopropane carboxylic acid in place of propionic acid in Step 2.

$^1$H NMR (CD$_3$OD; 300 MHz): δ1.08 (m, 4H), 2.06 (m, 1H), 2.55 (s, 3H), 2.56 (s, 3H), 5.63 (s, 2H), 6.99 (s, 1H), 7.10 (m, 4H), 7.49-7.63 (m, 4H).

FAB-MS: m/e 422 (M+H).

Preparation of 7-Methyl-2-propyl-3-(2'trifluoromethylsulfonamidobiphen-4-yl)methyl-3H-imidazo-[4,5-b]pyridine

EXAMPLE 41

Step 1: 4-Methyl-2'-nitrobiphenyl

A 1 L three-necked 24/40 round-bottom flask equipped with a mechanical stirrer, a 250 mL constant pressure addition funnel with a nitrogen inlet at the top, and a septum was flame dried, cooled and then charged with a solution of 29.07 g (0.17 mol) of p-bromotoluene in 100 mL of anhydrous tetrahydrofuran under a nitrogen atmosphere. The solution was stirred and cooled to −78° C. and 200 mL (0.34 mol) of a 1.7M solution of t-butyllithium in pentane was added via the addition funnel over 30 minutes. When the addition was complete, the cooling bath was removed and the reaction mixture was stirred for 30 minutes and allowed to warm to room temperature. The dropping funnel was next charged with 170 mL (0.17 mol) of a 1.0M solution of zinc chloride in diethylether which was added to the reaction mixture over a 10 minute period. A separate 1 L three-necked 24/40 round-bottom flask equipped with a mechanical stirrer, a nitrogen inlet and a septum, was flame dried, cooled and then charged with 4.04 g (6.0 mmol) of bis(triphenylphosphine)palladium(II) chloride and 50 mL of anhydrous tetrahydrofuran under a nitrogen atmosphere. The stirrer was started and 8.0 mL of a 1.5M solution (12 mmol) of diisobutylaluminum hydride in toluene was added to the suspension via syringe. The catalyst was stirred an additional 10 minutes at room temperature, and then a solution of 23.23 g (0.115 mol) of 1-bromo-2-nitrobenzene in 100 mL of anhydrous tetrahydrofuran was added. The suspension of the tolylzinc chloride was then transferred to the second flask via a wide diameter cannula. The reaction mixture was stirred an additional 45 minutes at room temperature, then most of the tetrahydrofuran was removed on a rotary evaporator. The resulting oil was partitioned between ethyl acetate and 1.0N hydrochloric acid. The organic layer was washed successively with water and brine, then dried (MgSO$_4$), filtered and evaporated. The residual oil was purified on a silica gel flash chromatography column eluted with 10% ethyl acetate-hexane to afford after evaporation and drying in vacuo 15.43 g (63%) of the product as a viscous yellow oil:

NMR (CDCl$_3$): δ2.36 (s, 3H), 7.16-7.24 (m, 4H), 7.38-7.46 (m, 2H), 7.55-7.62 (m, 1H), 7.80 (d, J=10 Hz, 1H).

MS (FAB) m/e 214 (MH+).

Step 2: 4-Bromomethyl-2'-nitrobiphenyl

A 2 L 24/40 three necked round-bottom flask equipped with a mechanical stirrer, a reflux condenser and a stopper, was charged with 15.427 g (72 mmol) of 4-methyl-2'-nitro[1,1'-biphenyl], 1.2 L of carbon tetrachloride, 14.164 g (80 mmol) of N-bromosuccinimide, and 0.50 g of 2,2'-azobis(2-methylpropionitrile). The stirred reaction mixture was refluxed under a nitrogen atmosphere for 4 hours, then cooled to room temperature and filtered. The filtrate was evaporated in vacuo and the residual oil was purified on a silica gel flash chromatography column eluted with 10% ethyl acetate-hexane. Evaporation of the pure fractions afforded the product as a yellow crystalline solid (7.83 g, 37%) which had: mp 109°-110° C.

NMR (CDCl$_3$): δ4.52 (s, 2H), 7.24-7.30 (m, 2H), 7.40-7.52 (m, 4H), 7.58-7.65 (m, 1H), 7.86 (d, J=10 Hz, 1H).

MS (FAB) m/e 294 (MH+).

Step 3: 7-Methyl-3-[(2'-nitrobiphen-4-yl)methyl]-2-propyl-3H-imidazo[4,5-b]pyridine To a solution of 0.913 g (5.2 mmol) of 7-methyl-2-propyl-3H-imidazo[4,5-b]pyridine in 10 mL of anhydrous dimethylformamide was added 0.210 g (5.7 mmol) of a 60% mineral oil dispersion of sodium hydride. The reaction mixture was magnetically stirred under a nitrogen atmosphere for 2 hours, at which point 1.675 g (5.7 mmol) of 4-bromomethyl-2'-nitrobiphenyl was added as a solid. The reaction mixture was stirred an additional 1 hour at room temperature, then partitioned between ethyl acetate and water. The organic layer was extracted, washed with brine, dried (MgSO$_4$), filtered and evaporated. The residual oil was purified on a silica gel flash chromatography column eluted with 75% ethyl acetate-hexane, which after evaporation of the pure fractions and drying in vacuo afforded 1.009 g (50%) of the product as a tan solid.

NMR (CDCl₃) δ0.97 (t, J=8 Hz, 3H), 1.70–1.83 (m, 2H), 2.66 (s, 3H), 2.81 (t, J=10 Hz, 2H), 5.52 (s, 2H), 7.02 (d, J=6 Hz, 1H), 7.14–7.25 (m, 4H), 7.36 (d, J=10 Hz, 1H), 7.42–7.48 (m, 1H), 7.56–7.61 (m, 1H), 7.82 (d, J=10 Hz, 1H), 8.20 (d, J=6 Hz, 1H).

MS (FAB) m/e 387 (MH+).

Step 4: 3-(2'-Aminobiphen-4-yl)methyl-7-methyl-2-propyl-3H-imidazo[4,5-b]pyridine To a solution of 0.475 g (1.23 mmol) of 7-methyl-3-[(2'-nitrobiphen-4-yl)methyl]-2-propyl-3H-imidazo[4,5-b]pyridine in 15 mL of absolute ethanol was added 50 mg of 10% palladium on carbon catalyst and the mixture was hydrogenated at 40 psig of hydrogen on a Parr apparatus. Reduction was complete after 1 hour and the reaction mixture was filtered and evaporated in vacuo to afford a tan solid (0.416 g, 95%) which was used in the subsequent step without further purification.

NMR (CDCl₃) δ0.98 (t, J=8 Hz, 3H), 1.70–1.86 (m, 3H), 2.66 (s, 3H), 2.83 (t, J=10 Hz, 2H), 3.64–3.72 (br s, 2H), 5.52 (s, 2H), 6.70–6.82 (m, 2H), 7.00–7.19 (m, 5H), 7.36 (d, J=10 Hz, 2H), 8.20 (d, J=6 Hz, 1H).

MS (FAB) m/e 357 (MH+).

Step 5: 7-Methyl-2-propyl-3-(2'-trifluoromethylsulfonamidobiphen-4-yl)methyl-3H-imidazo[4,5-b]-pyridine To a magnetically stirred solution of 0.115 g (0.32 mmol) of the product of Step 4 and 0.092 g (0.45 mmol) of 2,6-di-tert-butyl-4-methylpyridine in 1.5 mL of dry dichloromethane was added 65 mL (0.39 mmol) of trifluoromethanesulfonic anhydride under a nitrogen atmosphere at room temperature. After stirring under nitrogen for an additional 45 minutes, the reaction mixture was partitioned between ethyl acetate and water. The organic layer was extracted, washed with 0.5N hydrochloric acid, water, and brine, dried (MgSO₄), filtered and evaporated. The residual oil was purified on a silica gel flash chromatography column eluted with 75% ethyl acetate-hexane which after evaporation and drying in vacuo afforded 0.099 g (63%) of the product as an amorphous solid.

NMR (CDCl₃) δ0.98 (t, J=9 Hz, 3H), 1.74–1.86 (m, 2H), 2.68 (s, 3H), 2.82 (t, J=10 Hz, 2H), 5.54 (s, 2H), 7.04 (d, J=6 Hz, 1H), 7.18–7.31 (m, 6H), 7.33–7.41 (m, 1H), 7.59 (d, J=10 Hz, 1H), 8.20 (d, J=6 Hz, 1H).

MS (FAB) m/e 489 (MH+).

EXAMPLE 42

Step 1: 5,7-Dimethyl-2-ethyl-3-[(2'-nitrobiphen-4-yl)methyl]-3H-imidazo[4,5-b]pyridine To a solution of 0.199 g (1.13 mmol) of 5,7-dimethyl-2-ethyl-3H-imidazo[4,5-b]pyridine in 5 mL of anhydrous dimethylformamide was added 0.050 g (1.25 mmol) of a 60% mineral oil dispersion of sodium hydride. The reaction mixture was magnetically stirred under a nitrogen atmosphere for 30 minutes, at which point 0.365 g (1.25 mmol) of 4-bromomethyl-2'-nitrobiphenyl was added as a solid. The reaction mixture was stirred an additional 1.5 hours at room temperature, then partitioned between ethyl acetate and water. The organic layer was extracted, washed with brine, dried (MgSO₄), filtered and evaporated. The residual oil was purified on a silica gel flash chromatography column eluted with 50% ethyl acetate-hexane, which after evaporation of the pure fractions and drying in vacuo afforded 0.340 g (77%) of the product as a tan solid.

NMR (CDCl₃) δ1.31 (t, J=10 Hz, 3H), 2.58 (s, 3H), 2.62 (s, 3H), 2.78 (q, J=10 Hz, 2H), 5.48 (s, 2H), 6.88 (s, 1H), 7.14–7.24 (m, 4H), 7.34–7.38 (m, 1H), 7.42–7.48 (m, 1H), 7.54–7.60 (m, 1H), 7.83, (d, J=10 Hz, 1H).

MS (FAB) m/e 387 (MH+).

Step 2: 3-(2'-Aminobiphen-4-yl)methyl-5,7-dimethyl-2-ethyl-3H-imidazo[4,5-b]pyridine To a solution of 0.340 g (0.88 mmol) of the product of Step 1 in 15 mL of absolute ethanol was added 35 mg of 10% palladium on carbon catalyst and the mixture was hydrogenated at 40 psi of hydrogen on a Parr apparatus. Reduction was complete after 1.5 hours and the reaction mixture was filtered and evaporated in vacuo to afford a tan solid (0.300 g, 95%) which was used in the subsequent step without further purification.

NMR (CDCl₃) δ1.33 (t, J=10 Hz, 3H), 2.59 (s, 3H), 2.64 (s, 3H), 2.84 (q, J=10 Hz, 2H), 3.70 (br s, 2H), 5.48 (s, 2H), 6.70–6.82 (m, 2H), 6.90 (s, 1H), 7.03–7.22 (m, 4H), 7.36 (d, J=10 Hz, 2H).

MS (FAB) m/e 357 (MH+).

Step 3: 5,7-Dimethyl-2-ethyl-3-(2'-trifluoromethylsulfonamido-biphen-4-yl)methyl-3H-imidazo[4,5-b]pyridine To a magnetically stirred solution of 0.300 g (0.84 mmol) of the product of Step 2 and 0.190 g (0.93 mmol) of 2,6-di-tert-butyl-4-methylpyridine in 5.0 mL of dichloromethane was added 156 mL (0.93 mmol) of trifluoromethanesulfonic anhydride under a nitrogen atmosphere at 0° C. The reaction was stirred under a nitrogen atmosphere for 1 hour while it slowly warmed to room temperature, then the mixture was partitioned between ethyl acetate and water. The organic layer was extracted, washed with 0.5N hydrochloric acid, water, and brine, dried (MgSO₄), filtered and evaporated. The residual oil was purified on a silica gel flash chromatography column eluted with ethyl acetate to afford the semi-purified product. The concentrated fractions were rechromatographed on silica gel eluted with 5% methanol-chloroform which after evaporation and drying in vacuo afforded 0.090 g (22%) of the product as an amorphous solid.

NMR (CDCl₃) δ1.33 (t, J=10 Hz, 3H), 2.58 (s, 3H), 2.63 (s, 3H), 2.79 (q, J=10 Hz, 2H), 5.51 (s, 2H), 6.89 (s, 1H), 7.21–7.31 (m, 6H), 7.34–7.40 (m, 1H), 7.58 (d, J=11 Hz, 1H).

MS (FAB) m/e 489 (MH+).

EXAMPLE 43

Step 1: 2'-Methylbiphenyl-4-carboxylic acid methyl ester

A 2 L three-necked 24/40 round-bottom flask equipped with a mechanical stirrer, a 500 mL constant pressure addition funnel with a nitrogen inlet at the top, and a septum was flame dried, cooled and then charged with a solution of 70.00 g (0.409 mol) of o-bromotoluene in 350 mL of anhydrous tetrahydrofuran under a nitrogen atmosphere. The solution was stirred and cooled to −78° C. and 481 mL (0..818 mol) of a 1.7M solution of t-butyllithium in pentane was added via the addition funnel over 45 minutes. When the addition was complete, the cooling bath was removed and the reaction mixture was stirred for 45 minutes and allowed to warm to room temperature. The dropping funnel was next charged with 409 mL (0.409 mol) of a 1.0M solution of zinc chloride in diethylether which was added to the reaction mixture over a 20 minute period. A separate 2 L three-necked 24/40 round-bottom flask equipped with a mechanical stirrer, a nitrogen inlet and a septum, was flame dried, cooled and then charged with 8.93 g (13.7 mmol) of bis(triphenylphosphine)nickel(II) chloride, 58.71 g (0.273 mol) of methyl-2-bromobenzoate and 450 mL of anhydrous tetrahydrofuran under a nitrogen atmosphere. The suspension of the tolylzinc chloride was then transferred to the second flask via a wide diameter cannula. The reaction mixture was stirred an additional 45 minutes at room temperature, then most of the tetrahydrofuran was removed on a rotary evaporator. The resulting oil was partitioned between ethyl acetate (500 mL) and water (300 mL). The organic layer was washed successively with water, 5% hydrochloric acid, water, and brine, then dried ($MgSO_4$), filtered and evaporated. The residual oil was purified on a Waters Prep 500 HPLC (2 silica packs) eluted with 1.5% ethyl acetate-hexane in eleven separate runs (mixed fractions recycled, 10 g per injection). The purified fractions were evaporated and freed of residual solvent in vacuo to afford 53.42 g (74%) of a colorless oil which had.

NMR ($CDCl_3$) $\delta$2.25 (s, 3H), 3.93 (s, 3H), 7.19–7.28 (m, 4H), 7.39 (d, J=12 Hz, 2H), 8.08 (d, J=12 Hz, 2H); MS (FAB) m/e (MH+).

Step 2: 2'-Bromomethylbiphenyl-4-carboxylic acid methyl ester

A 5 L three-necked 24/40 round-bottom flask equipped with a mechanical stirrer, a reflux condenser with a nitrogen inlet at the top, and a thermometer was charged with 53.42 g (0.204 mol) of 2'-methyl biphenyl-4-carboxylic acid methyl ester, 3.4 L carbon tetrachloride, 38.09 g (0.214 mol) of N-bromosuccinimide and 2.0 g of 2,2'-azobis(2-methylpropionitrile). The flask was degassed and flushed with nitrogen, the stirrer was started and the contents were refluxed for 5 hours. The reaction mixture was then cooled to room temperature, filtered and evaporated. The residual oil was purified by recrystallization from dichloromethane-hexane to afford 48.48 g (78%) of the product which had.

mp 80°–81° C.

NMR ($CDCl_3$) $\delta$3.94 (s, 3H), 4.40 (s, 2H), 7.20–7.26 (m, 1H), 7.32–7.41 (m, 2H), 7.48–7.54 (m, 3H), 8.12 (d, J=12 Hz, 2H).

MS (EI) m/e 304, 306 (M+).

Anal. ($C_{15}H_{13}BrO_2$) C, H.

Step 3: 2'-[(Aminoiminomethyl)thio]methylbiphenyl-4-carboxylic acid methylester, hydrobromide To a solution of 4.120 g (54.1 mmol) of thiourea in 80 mL absolute ethanol was added a solution of 15.01 g (49.2 mmol) of 2'-bromomethylbiphenyl-4-carboxylic acid methyl ester in 25 mL absolute ethanol and the mixture was magnetically stirred and refluxed for 4 hours. After cooling to room temperature, a portion of the product which had crystallized during the reaction was isolated by filtration. The remainder of the product was crystallized from the filtrate by addition of diethyl ether, filtered, and the combined product was dried in vacuo to afford 17.108 g (91%) of the isothiouronium salt which had: mp 233°–234° C.

MS (FAB) m/e 301 (MH+-Br).

Step 4: 2'-(N-t-Butylsulfonamido)methylbiphenyl-4-carboxylic acid methyl ester

A 500 mL 24/40 round-bottom flask charged with a suspension of 7.58 g (19.9 mmol) of the product of Step 3 in 175 mL glacial acetic acid and 25 mL water was magnetically stirred at 0° C. and treated with a stream of chlorine gas introduced through a capillary pipet. After 20 min the chlorination was stopped, and the homogeneous yellow-green solution was diluted with 500 mL water. The oily layer which separated was extracted into diethyl ether. The organic layer was washed with water, 5% aqueous sodium thiosulfate, brine, then dried ($MgSO_4$), filtered and evaporated. The residual oil was crystallized from diethyl ether-hexane and briefly dried in vacuo to afford the sulfonyl chloride: MS (EI) m/e 324 (M+). The sulfonyl chloride was then dissolved in 20 mL dichloromethane and was slowly added to a stirred solution of 10 mL (95.0 mmol) of tert-butylamine in 20 mL of dichloromethane. After stirring 20 minutes at room temperature, the reaction mixture was partitioned between dichloromethane and water. The organic layer was washed with 1N hydrochloric acid and water, dried ($MgSO_4$), filtered and evaporated. The product was purified on a silica gel flash chromatography column eluted with 25% ethyl acetate-hexane to afford 5.050 g (70%) of the sulfonamide as a viscous oil which had:

NMR ($CDCl_3$) $\delta$1.16 (s, 9H), 3.94 (s, 3H), 4.28 (s, 2H), 7.24–729 (m, 1H), 7.36–7.43 (m, 2H), 7.45 (d, J=12 Hz, 1H), 7.64–7.70 (m, 1H), 8.08 (d, J=12 Hz, 1H); MS (EI) m/e 361 (M+).

Step 5: 2-N-t-Butylsulfoamidomethyl-4-hydroxymethylbiphenyl

To a magnetically stirred solution of 5.050 g (14.0 mmol) of the sulfonamide-ester (Step 4) in 25 mL anhydrous tetrahydrofuran was slowly added 18 mL (18.0 mmol) of a 1.0M solution of lithium aluminum hydride in tetrahydrofuran via syringe at room temperature under a nitrogen atmosphere. The reaction mixture was stirred for 5 hours at room temperature. At this point the excess reducing agent was decomposed by dropwise addition of water. The resulting suspension was diluted with ethyl acetate, and the aqueous layer was acidified with concentrated hydrochloric acid until the precipitated salts were redissolved. The organic layer was then extracted and separated, washed with water, brine, dried ($MgSO_4$), filtered and evaporated. The residual oil was purified on a silica gel flash chromatography column eluted with 75% ethyl acetate-hexane, and after evaporation of the fractions and drying in vacuo afforded 2.282 g (49%) of the product as a viscous oil which had:

NMR ($CDCl_3$) $\delta$1.15 (s, 9H), 1.56 (s, 1H), 3.87 (s, 1H), 4.32 (s, 2H), 4.74 (br s, 2H), 7.24–7.28 (m, 1H), 7.34–7.45 (m, 6H), 7.64–7.69 (m, 1H).

MS (EI) m/e 333 (M+).

Step 6: 2-N-t-Butylsulfonamido-4'-iodomethylbiphenyl

A dry 15 mL 14/20 round-bottom equipped with a magnetic stir bar and a septum was charged sequentially with 1.162 g (3.49 mmol) of the product of Step 5, 7.0 mL of dichloromethane, 0.73 mL (5.23 mmol) of triethylamine, and stirred at 0° C. under a nitrogen atmosphere. Methanesulfonyl chloride (0.33 mL, 4.18 mmol) was added slowly via syringe and the reaction mixture was then stirred for 30 minutes. The reaction mixture was then partitioned between dichloromethane and water; the organic layer was separated, dried ($MgSO_4$), filtered and evaporated. The residual oil was then redissolved in 3.0 mL of acetone, magnetically stirred at room temperature and treated with a solution of 1.045 g (7.0 mmol) of sodium iodide in 10 mL of acetone. After stirring for 15 minutes, the reaction mixture was concentrated in vacuo and the residue was partitioned between ethyl acetate and water. The organic layer was then separated, washed with 5% sodium thiosulfate solution, brine, dried ($MgSO_4$), filtered, evaporated and dried in vacuo to afford 1.486 g (96%) of the iodide as a viscous oil which had:

NMR (CDCl$_3$) δ1.14 (s, 9H), 3.87 (br s, 1H), 4.30 (s, 2H), 4.48 (s, 2H), 7.24–7.32 (m, 3H), 7.34–7.46 (m, 4H), 7.64–7.68 (m, 1H).

MS (EI) m/e 443 (M+).

Step 7: 3-(2'-N-t-Butylsulfonamidomethylbiphen-4-yl)methyl-7-methyl-2-propyl-3H-imidazo[4,5-b]pyridine To a solution of 0.587 g (3.35 mmol) of 7-methyl-2-propyl-3H-imidazo[4,5-b]pyridine in 8.0 mL of anhydrous dimethylformamide was added 0.161 g (4.02 mmol) of a 60% mineral oil dispersion of sodium hydride and the resultant reaction mixture was stirred under a nitrogen atmosphere for 30 minutes at room temperature. At this point, a solution of 1.486 g (3.35 mmol) of the product of Step 6 in 2.0 mL of anhydrous dimethylformamide was transferred to the reaction mixture via cannula. The reaction mixture was stirred an additional 45 minutes at room temperature and then was partitioned between ethyl acetate and water. The organic layer was separated, washed with water, brine, dried (MgSO$_4$), filtered, and evaporated. The residual oil was purified on a silica gel flash chromatography column eluted with ethyl acetate. Evaporation of the appropriate fractions and drying in vacuo, afforded 0.982 g (60%) of the product as a viscous oil which had:

NMR (CDCl$_3$) δ0.98 (t, J=10 Hz, 3H), 1.11 (s, 9H), 1.82 (m, 2H), 2.67 (s, 3H), 2.84 (t, J=10 Hz, 2H), 3.88 (s, 1H), 4.24 (s, 2H), 5.51 (s, 2H), 7.02 (d, J=8 Hz, 1H), 7.14–7.24 (m, 3H), 7.26–7.37 (m, 4H), 7.60–7.65 (m, 1H), 8.18 (d, J=8 Hz, 1H).

MS (EI) m/e 490 (M+).

Step 8: 7-Methyl-2-propyl-3-(2'-sulfonamidomethylbiphen-4-yl)methyl-3H-imidazo[4,5-b]pyridine To a solution of 0.982 g (2.00 mmol) of the product of Step 7 in 2.0 mL of dichloromethane was added 2.0 mL of trifluoroacetic acid and the reaction mixture was stirred under a nitrogen atmosphere for 16 hours at room temperature. The reaction mixture was then concentrated in vacuo and the residue was purified on a silica gel flash chromatography column eluted with 80% ethyl acetate-hexane. After concentration of the purified fractions and drying in vacuo 0.835 g (96%) of the primary sulfonamide as an amorphous solid was obtained which had:

NMR (CDCl$_3$) δ1.02 (t, J=10 Hz, 3H), 1.76–1.88 (m, 2H), 2.74 (s, 3H), 3.08 (t, J=10 Hz, 2H), 4.29 (s, 2H), 4.63 (br s, 2H), 5.63 (s, 2H), 7.17–7.40 (m, 8H), 7.58–7.64 (m, 1H), 8.33 (d, J=8 Hz, 1H); MS (EI) m/e 434 (M+).

Step 9: 3-(2'-(N-Acetyl)sulfonamidomethylbiphen-4-yl)methyl-7-methyl-2-propyl-3H-imidazo[4,5-b]pyridine To a solution of acetic anhydride (0.5 mL) and pyridine (0.5 mL) was added 0.034 g (0.078 mmol) of the product of Step 8 and the resulting mixture was magnetically stirred under a nitrogen atmosphere at room temperature for 16 hours. The reaction mixture was evaporated in vacuo and the residue was purified on a silica gel flash chromatography column eluted with ethyl acetate. Evaporation of the purified fractions and drying in vacuo afforded 0.018 g (49%) of the product as a white foam which had:

NMR (CDCl$_3$) δ1.03 (t, J=10 Hz, 3H), 1.94 (m, 2H), 2.05 (s, 3H), 2.86 (s, 3H), 3.21 (t, J=10 Hz, 2H), 4.55 (s, 2H), 5.66 (s, 2H), 7.16–7.38 (m, 8H), 7.46–7.49 (m, 1H), 8.47 (d, J=8 Hz, 1H), 8.92 (br s, 1H).

MS (EI) m/e 476 (M+).

EXAMPLE 44

5-Bromo-2-ethyl-7-methyl-3-(2'-(tetrazol-5-yl)biphen-4-yl)methyl-3H-imidazo[4,5-b]-pyridine Step 1: 5-Chloro-2-ethyl-7-methylimidazo[4,5-b]pyridine A solution of 2-ethyl-7-methylimidazo[4,5-b]pyridine (28 g, 174 mmol) and m-chloroperbenzoic acid (80–90%, 44.6 g) in CHCl$_3$ (300 mL) was heated at reflux for 0.5 hours. The mixture was concentrated and purified (SiO$_2$, 100% CH$_2$Cl$_2$ gradient to 30% CH$_2$Cl$_2$/MeOH) to give 29.8 g of 2-ethyl-7-methylimidazo[4,5-b]pyridine-4-oxide as a solid.

$^1$H NMR (300 MHz, CD$_3$OD) δ8.13 (d, 1H, J=6 Hz), 7.13 (d, 1H, J=6 Hz), 3.01 (q, 2H, J=7.5 Hz), 2.60 (s, 3H), 1.46 (t, 3H, J=7.5 Hz).

A mixture of the N-oxide (29.75 g, 0.168 mol), CHCl$_3$ (25 mL) and POCl$_3$ (160 mL) was heated to 80° C. for 1 hours. After pouring over ice, the mixture was neutralized by careful addition of NH$_4$OH and extracted with EtOAc. Concentration gave 23.8 g of 5-chloro-2-ethyl-7-methylimidazo[4,5-b]pyridine as a solid.

$^1$H NMR (250 MHz, CDCl$_3$) δ7.07 (s, 1H) 3.10 (q, 2H, J=7.5 Hz), 2.67 (s, 3H), 1.48 (t, 3H, J=7.5 Hz).

Step 2: 5-Bromo-2-ethyl-7-methylimidazo[4,5-b]pyridine

A mixture of the above stated chloride (22.2 g, 0.113 mol) in 30% HBr-HOAc was heated to 100° C. for 19 hours. The mixture was poured onto ice, neutralized with NH$_4$OH, extracted (5×EtOAc), and the organic layers were concentrated to give 15 g (1$^{st}$ crop) of the bromide as a solid after crystallization from EtOAc.

$^1$H NMR (300 MHz, CDCl$_3$) δ7.22 (s, 1H) 3.13 (q, 2H, J=7.5 Hz), 2.66 (s, 3H), 1.47 (t, 3H, J=7.5 Hz).

Step 3: 5-Bromo-2-ethyl-7-methyl-3-(2'-(tetrazol-5-yl)biphen-4-yl)methyl-3H-imidazo-[4,5-b]pyridine The title compound was prepared according to the procedure described in Example 7 from 5-bromo-2-ethyl-7-methylimidazo[4,5-b]pyridine.

$^1$H NMR (300 MHz, CD$_3$OD) δ7.68–7.62 (m, 2H), 7.57–7.50 (m, 2H), 7.31 (s, 1H), 7.13–7.05 (m, 4H), 5.51 (s, 2H), 2.87 (q, 2H, J=7.5 Hz), 2.62 (s, 3H), 1.26 (t, 3H, J=7.5 Hz).

EXAMPLE 45

5-Chloro-2-ethyl-7-methyl-3-(2'-(tetrazol-5-yl)biphen-4-yl)methyl-3H-imidazo[4,5-b]pyridine The title compound was prepared according to the procedure described in Example 7 from 5-chloro-2-ethyl-7-methylimidazo[4,5-b]pyridine.

$^1$H NMR (300 MHz, CD$_3$OD) δ7.65–7.59 (m, 2H), 7.57–7.49 (m, 2H), 7.17 (s, 1H), 7.10 (apparent s, 4H), 5.50 (s, 2H), 2.86 (q, 2H, J=7.5 Hz), 2.63 (s, 3H), 1.26 (t, 3H, J=7.5 Hz).

EXAMPLE 46

5-Cyano-2-ethyl-7-methyl-3-(2'-(tetrazol-5-yl)biphen-4-yl)methyl-3H-imidazo[4,5-b]pyridine A mixture of 5-bromo-2-ethyl-7-methyl-3-(2'-(tetrazol-5-yl)biphen-4-yl)methyl-3H-imidazo[4,5-b]pyridine (41 mg), CuCN (80 mg), and pyridine (0.2 mL) was heated with stirring to 160° C. for 4 hours. The pyridine distilled off during the course of the heating. The cooled dark mass was dissolved in 2 mL of 20% aqueous KCN by heating to 50° C. for 15 minutes. Acetic acid (2 mL) (Caution! HCN is evolved.) was added and the mixture was extracted (2×EtOAc). The organic layers were dried (Na₂SO₄), concentrated, and purified (SiO₂, 80/20/1 CH₂Cl₂—MeOH—NH₄OH) to give 26 mg of the title compound as a solid.

¹H NMR (250 MHz, CD₃OD) δ7.66-7.45 (m, containing a singlet at 7.57, 5H), 7.15-7.04 (m, 4H), 5.53 (s, 2H), 2.91 (q, 2H, J=7.5 Hz), 2.66 (s, 3H), 1.27 (t, 3H, J=7.5 Hz).

EXAMPLE 47

5-Carboxy-2-ethyl-7-methyl-3-(2'-(tetrazol-5-yl)biphen-4-yl)methyl-3H-imidazo[4,5-b]pyridine To neat 5-Cyano-2-ethyl-7-methyl-3-(2'-(tetrazol-5-yl)biphen-4-yl)methyl-3H-imidazo[4,5-b]pyridine (20 mg) at RT was added H₂SO₄ (0.5 mL) and water (0.25 mL). The mixture was heated to 100° C. for 3 hours, cooled to 0° C., then made basic by the addition of NH₄OH. After adding methanol (5 mL), the mixture was filtered, concentrated, and purified (SiO₂, 60:40:1 CH₂Cl₂—CH₃OH—NH₄OH) to give 17 mg of the title compound as a solid.

FAB MS (M⁺+1)=440.

¹H NMR (300 MHz, CD₃OD) δ7.90 (s, 1H), 7.56-7.39 (m, 4H), 7.05 (apparent s, 4H), 5.62 (s, 2H), 2.86 (q, 2H, J=7.5 Hz), 2.67 (s, 3H), 1.26 (t, 3H, J=7.5 Hz).

EXAMPLE 48

5-(Ethoxycarbonyl)-2-ethyl-7-methyl-3-(2'-(tetrazol-5-yl)biphen-4-yl)methyl-3H-imidazo-[4,5-b]pyridine Dry HCl was bubbled through a slurry of 5-carboxy-2-ethyl-7-methyl-3-(2'-(tetrazol-5-yl)biphen-4-yl)methyl-3H-imidazo[4,5-b]pyridine (200 mg) in EtOH (50 mL) for 30 seconds. The mixture became homogeneous and was stirred for 18 hour at RT. Concentration, neutralization (NH₄OH), partitioning between dilute aqueous HOAc and EtOAc followed by evaporation of the organic layer gave 220 mg of the title compound as a solid.

¹H NMR (300 MHz, CD₃OD) δ7.94 (s, 1H), 7.63-7.56 (m, 2H), 7.51 (apparent t, 2H, J=8 Hz), 7.12-7.03 (AB quartet, 4H), 5.62 (s, 2H), 4.44 (q, 2H, J=7.2 Hz), 2.86 (q, 2H, J=7.5 Hz), 2.70 (s, 3H), 1.43 (t, 3H, J=7.2 Hz), 1.27 (t, 3H, J=7.5 Hz).

EXAMPLE 49

2-Ethyl-5-(methoxycarbonyl)-7-methyl-3-(2'-(tetrazol-5-yl)biphen-4-yl)methyl-3H-imidazo-[4,5-b]pyridine The title compound was prepared by using a similar method to that described in Example 48.

¹H NMR (300 MHz, CD₃OD) δ7.98 (s, 1H), 7.68-7.62 (m, 2H), 7.54 (apparent t, 2H, J=8 Hz), 7.16-7.06 (AB quartet, 4H), 5.66 (s, 2H), 3.99 (s, 3H), 2.91 (q, 2H, J=7.5 Hz), 2.71 (s, 3H), 1.28 (t, 3H, J=7.5 Hz).

EXAMPLE 50

5-(Benzyloxycarbonyl)-2-ethyl-7-methyl-3-(2'-(tetrazol-5-yl)biphen-4-yl)methyl-3H-imidazo-[4,5-b]pyridine The title compound was prepared by using a similar method to that described in Example 48.

FAB MS (M⁺+1)=530.

¹H NMR (300 MHz, CD₃OD) δ7.96 (s, 1H), 7.58-7.33 (m, 9H), 7.12-7.03 (AB quartet, 4H), 5.60 (s, 2H), 5.44 (s, 2H), 2.90 (q, 2H, J=7.5 Hz), 2.68 (s, 3H), 1.28 (t, 3H, J=7.5 Hz).

EXAMPLE 51

2-Ethyl-5-(iso-propyloxycarbonyl)-7-methyl-3-(2'-(tetrazol-5-yl)biphen-4-yl)methyl-3H-imidazo-[4,5-b]pyridine The title compound was prepared by using a similar method to that described in Example 48.

FAB MS (M⁺+1)=482.

¹H NMR (300 MHz, CD₃OD) δ7.93 (s, 1H), 7.57-7.38 (m, 4H), 7.07 (s, 4H), 5.61 (s, 2H), 5.29 (quintet, 1H, J=6.3 Hz), 2.89 (q, 2H, J=7.5 Hz), 2.69 (s, 3H), 1.42 (d, 2H, J=6.3 Hz), 1.27 (t, 3H, J=7.5 Hz).

EXAMPLE 52

5-(n-Butyloxycarbonyl)-2-ethyl-7-methyl-3-(2'-(tetrazol-5-yl)biphen-4-yl)methyl-3H-imidazo-[4,5-b]pyridine The title compound was prepared by using a similar method to that described in Example 48.

¹H NMR (300 MHz, CD₃OD) δ7.92 (s, 1H), 7.61 (t, 2H, J=7.6 Hz), 7.55-7.45 (m, 2H), 7.18-7.03 (AB quartet, 4H), 5.62 (s, 2H), 4.38 (t, 2H, J=6.6 Hz), 2.89 (q, 2H, J=7.5 Hz), 2.67 (s, 3H), 1.84-1.73 (m, 2H), 1.59-1.43 (m, 2H), 1.26 (t, 3H, J=7.5 Hz), 0.99 (t, 3H, J=7.5 Hz).

EXAMPLE 53

5-Carboxamido-2-ethyl-7-methyl-3-(2'-(tetrazol-5-yl)biphen-4-yl)methyl-3H-imidazo[4,5-b]pyridine To 5-Cyano-2-ethyl-7-methyl-3-(2'-(tetrazol-5-yl)biphen-4-yl)methyl-3H-imidazo[4,5-b]pyridine (22 mg) at RT was added 0.63 mL of 0.5N aqueous NaOH, MeOH (0.3 mL), and H₂O₂ (0.018 mL). After stirring for 16 hours the solution was evaporated and purified (SiO₂, 80/20/1 CH₂Cl₂/MeOH/NH₄OH) to give 20 mg solid.

¹H NMR (300 MHz, CD₃OD) δ7.91 (s, 1H), 7.58-7.41 (m, 4H), 7.12-7.03 (AB quartet, 4H), 5.58 (s, 2H), 2.89 (q, 2H, J=7.5 Hz), 2.68 (s, 3H), 1.27 (t, 3H, J=7.5 Hz).

EXAMPLE 54

2-Ethyl-7-methyl-5-(morpholin-4-yl)carbonoyl-3-(2'-(tetrazol-5-yl)biphen-4-yl)methyl-3H-imidazo[4,5-b]pyridine To 5-(ethoxycarbonyl)-2-ethyl-7-methyl-3-(2'-(tetrazol-5-yl)biphen-4-yl)methyl-3H-imidazo[4,5-b]pyridine (30 mg) in THF (1 mL) at RT was added 0.25 mL of morpholine and NaH (20 mg of an 80% dispersion). After stirring for 16 hours, 1% aqueous HOAc (2 mL) was added. Extractive workup (EtOAc), and purification (SiO₂, 75/25/1 CH₂Cl₂/MeOH/NH₄OH) gave 10 mg of a solid.

¹H NMR (300 MHz, CD₃OD) δ7.62-7.52 (m, 2H), 7.50-7.42 (m, 2H), 7.40 (s, 1H), 7.06 (s, 4H), 5.52 (s, 2H), 3.82-3.72 (m, 4H), 3.58-3.46 (m, 4H), 2.94 (q, 2H, J=7.5 Hz), 2.69 (s, 3H), 1.30 (t, 3H, J=7.5 Hz)

EXAMPLE 55

2-Ethyl-7-methyl-5-(isopropyl)-3-(2'-(tetrazol-5-yl)biphen-4-yl)methyl-3H-imidazo[4,5-b]pyridine To 5-bromo-2-ethyl-7-methyl-3-(2'-(tetrazol-5-yl)biphen-4-yl)methyl-3H-imidazo-[4,5-b]pyridine (75 mg) in THF (2 mL) at −78° C. was sequentially added ZnCl₂ (1.58 mL, 1M/ether), iso-propylmagnesium chloride (0.79 mL, 2M/ether), and tetrakis-triphenylphosphinepalladium (15 mg). After complete addition the reaction was warmed to RT and stirred for 16 hours.

Extractive workup (EtOAc, from dilute HOAc), and purification (SiO$_2$, 80/20/1 CH$_2$Cl$_2$/MeOH/NH$_4$OH) gave 43 mg of a solid.

$^1$H NMR (300 MHz, CD$_3$OD) δ 7.60–7.50 (m, 2H), 7.45 (t, 2H, J=6.9 Hz), 7.12–7.00 (m, 5H), 5.50 (s, 2H), 3.10 (quintet, 1H, J=6.9 Hz) 2.84 (q, 2H, J=7.5 Hz), 2.59 (s, 3H), 1.31 (d, 6H, J=6.9 Hz), 1.24 (t, 3H, J=7.5 Hz).

EXAMPLE 56

5-Ethyl-2-ethyl-7-methyl-3-(2'-(tetrazol-5-yl)biphen-4-yl)methyl-3H-imidazo]4,5-b]pyridine The title compound was prepared by using a similar method to that described in Example 55.

$^1$H NMR (300 MHz, CD$_3$OD) δ7.64–7.43 (m, 4H), 7.12–7.00 (m, 5H), 5.52 (s, 2H), 2.90–2.78 (m, 4H), 2.58 (s, 3H), 1.35–1.19 (m, 6H).

EXAMPLE 57

2-Ethyl-5-(n-hexyl)-7-methyl-3-(2'-(tetrazol-5-yl)biphen-4-yl)methyl-3H-imidazo[4,5-b]pyridine The title compound was prepared by using a similar method to that described in Example 55.

$^1$H NMR (300 MHz, CD$_3$OD) δ7.60 (t, 2H J=7.8 Hz) 7.54–7.44 (m, 2H), 7.14–7.03 (m, 4H), 7.06 (s, 1H), 5.53 (s, 2H), 2.90–2.78 (m, 4H), 2.59 (s, 3H), 1.78–1.64 (m, 2H), 1.40–1.24 (m, 6H), 1.24 (t, 3H), J=7.5 Hz), 0.86 (t, 3H, J=6 Hz).

EXAMPLE 58

2-Ethyl-7-methyl-5-phenyl-3-(2'-(tetrazol-5-yl)biphen-4-yl)methyl-3H-imidazo[4,5-b]pyridine The title compound was prepared by using a similar method to that described in Example 55.

$^1$H NMR (300 MHz, CD$_3$OD) δ8.07 (d, 2H, J=7.2 Hz), 7.63 (s, 1H), 7.58–7.34 (m, 7H), 7.16–7.04 (m, 4H), 5.56 (s, 2H), 2.89 (q, 2H, J=7.5 Hz), 2.69 (s, 3H), 1.29 (t, 3H, J=7.5 Hz).

EXAMPLE 59

2-Ethyl-7-methyl-5-(tetrazol-5-yl)-3-(2'-(tetrazol-5-yl)biphen-4-yl)methyl-3H-imidazo[4,5-b]pyridine A mixture of 5-Cyano-2-ethyl-7-methyl-3-(2'-(tetrazol-5-yl)biphen-4-yl)methyl-3H-imidazo[4,5-b]pyridine (54 mg), trimethylstannyl azide (79 mg), toluene (5 mL), and DMF (1 mL) was heated to 110° C. for 24 hour. Concentration and purification (SiO$_2$, 70/30/1 CH$_2$Cl$_2$/MeOH/NH$_4$OH) gave 47 mg solid.

$^1$H NMR (300 MHz, CD$_3$OD) δ7.93 (s, 1H), 7.56–7.38 (m, 4H), 7.14–7.05 (AB quartet, 4H), 5.61 (s, 2H), 2.86 (q, 2H, J=7.5 Hz), 2.71 (s, 3H), 1.27 (t, 3H, J=7.5 Hz)

EXAMPLE 60

5-Acetyl-2-ethyl-7-methyl-3-(2'-(tetrazol-5-yl)biphen-4-yl)methyl-3H-imidazo[4,5-b]pyridine To 5-Cyano-2-ethyl-7-methyl-3-(2'-(tetrazol-5-yl)biphen-4-yl)methyl-3H-imidazo[4,5-b]pyridine (137 mg) at 0° C. in THF (5 mL) was added methylmagnesium bromide (0.70 mL, 3M/ether). After stirring for 6 hour, 10% aqueous HOAc was added, the mixture was heated to 50° C. for 10 minutes then extracted with EtOAc. Purification (SiO$_2$, 93/3/4 CH$_2$Cl$_2$/MeOH/HOAc) gave 40 mg of the title compound.

$^1$H NMR (300 MHz, CD$_3$OD) δ7.88 (s, 1H), 7.67–7.60 (m, 2H), 7.58–7.50 (m, 2H), 7.28–7.05 (AB quartet, 4H), 5.63 (s, 2H), 2.95 (q, 2H, J=7.5 Hz), 2.70 (s, 3H), 2.68 (s, 3H), 130 (t, 3H, J=7.5 Hz)

EXAMPLE 61

2-Ethyl-5-((RS)-1-hydroxy)ethyl-7-methyl-3-(2'-(tetrazol-5-yl)biphen-4-yl)methyl-3H-imidazo[4,5-b]pyridine To 5-acetyl-2-ethyl-7-methyl-3-(2'-(tetrazol-5-yl)biphen-4-yl)methyl-3H-imidazo[4,5-b]pyridine (25 mg) in MeOH (1 mL) at 0° C. was added NaBH$_4$ (50 mg). After 0.5 hours, 1% aqueous HOAc (2 mL) was added. Extractive workup (EtOAc), and purification (SiO$_2$, 93/3/4 CH$_2$Cl$_2$/MeOH/HOAc) gave 25 mg of the title compound.

$^1$H NMR (300 MHz, CD$_3$OD) δ7.58 (t, 2H, J=7.5 Hz), 7.48 (t, 2H, J=7.5 Hz), 7.27 (s, 1H), 7.14–7.02 (AB quartet, 4H), 5.54 (s, 2H), 4.94 (q, 1H, J=6.6 Hz), 2.85 (q, 2H, J=7.5 Hz), 2.63 (s, 3H), 1.51 (d, 3H, J=6.6 Hz), 1.24 (t, 3H, J=7.5 Hz).

EXAMPLE 62

2-Ethyl-5-(hydroxymethyl)-7-methyl-3-(2'-(tetrazol-5-yl)biphen-4-yl)methyl-3H-imidazo[4,5-b]pyridine To 5-(ethoxycarbonyl)-2-ethyl-7-methyl-3-(2'-(tetrazol-5-yl)biphen-4-yl)methyl-3H-imidazo[4,5-b]pyridine (50 mg) in THF (1 mL) at −78° C. was added Diisobutylaluminum hydride (0.534 mL, 1M/THF). After 1 hour at −78° C., the mixture was warmed to RT and 1% aqueous HOAc (2 mL) was added. Extractive workup (EtOAc), and purification (SiO$_2$, 80/20/1 CH$_2$Cl$_2$/MeOH/NH$_4$OH) gave 28 mg of a solid.

$^1$H NMR (300 MHz, CD$_3$OD) δ7.57 (t, 2H, J=7.5 Hz), 7.48 (t, 2H, J=7.5 Hz), 7.26 (s, 1H), 7.08–7.02 (AB quartet, 4H), 5.54 (s, 2H), 4.74 (s, 2H), 2.85 (q, 2H, J=7.5 Hz), 2.66 (s, 3H), 1.26 (t, 3H, J=7.5 Hz).

EXAMPLE 63

2-Ethyl-5-(2-hydroxyprop-2-yl)-7-methyl-3-(2'-(tetrazol-5-yl)biphen-4-yl)methyl-3H-imidazo[4,5-b]pyridine To 5-(ethoxycarbonyl)-2-ethyl-7-methyl-3-(2'-(tetrazol-5-yl)biphen-4-yl)methyl-3H-imidazo[4,5-b]pyridine (43 mg) at −78° C. in THF (1 mL) was added methylmagnesium bromide (0.77 mL, 3M/ether). Extractive workup (EtOAc, from aqueous NH$_4$Cl) and purification (SiO$_2$, 93/3/4 CH$_2$Cl$_2$/MeOH/HOAc) gave 20 mg of the title compound.

$^1$H NMR (300 MHz, CD$_3$OD) δ7.56–7.40 (m, 4H), 7.39 (s, 1H), 7.24–7.04 (AB quartet, 4H), 5.50 (s, 2H), 2.87 (q, 2H, J=7.5 Hz), 2.64 (s, 3H), 1.59 (s, 6H), 1.27 (t, 3H, J=7.5 Hz)

EXAMPLE 64

2-Ethyl-5-(3-hydroxypent-3-yl)-7-methyl-3-(2'-(tetrazol-5-yl)biphen-4-yl)methyl-3H-imidazo[4,5-b]pyridine The title compound was prepared by using a similar method to that described in Example 63.

$^1$H NMR (300 MHz, CD$_3$OD) δ7.65–7.59 (m, 2H), 7.51 (m, 2H), 7.30 (s, 1H), 7.20–7.02 (AB quartet, 4H), 5.50 (s, 2H), 2.90 (q, 2H, J=7.5 Hz), 2.65 (s, 3H), 2.07–1.79 (m, 4H), 1.27 (t, 3H, J=7.5 Hz), 0.68 (t, 6H, J=7.2 Hz).

EXAMPLE 65

5-Amino-2-ethyl-7-methyl-3-(2'-(tetrazol-5-yl)biphen-4-yl)methyl-3H-imidazo[4,5-b]pyridine A mixture of 5-Bromo-2-ethyl-7-methyl-3-(2'-(tetrazol-5-yl)biphen-4-yl)methyl-3H-imidazo[4,5-b]pyridine. (2.0 g), and hydrazine hydrate (15 mL) was heated to 120° C. for 24 hours. Concentration and purification ($SiO_2$, 85/14/2 $CH_2Cl_2$/MeOH/$NH_4OH$) gave 1.80 g of 5-hydrazino-2-ethyl-7-methyl-3-(2'-(tetrazol-5-yl)biphen-4-yl)methyl-3H-imidazo[4,5-b]pyridine. Reduction in methanol (50 mL) under 1 atm. $H_2$ with W-2 Raney nickle (1 mL, 50% dispersion/water) at RT for 48 hours gave the title compound (1.44 g) after purification ($SiO_2$, 85/14/2 $CH_2Cl_2$/MeOH/$NH_4OH$).

$^1$H NMR (300 MHz, $CD_3OD$) δ7.60-7.50 (m, 2H), 7.49-7.42 (m, 2H), 7.10-7.00 (m, 4H), 6.38 (s, 1H), 5.39 (s, 2H), 2.79 (q, 2H, J=7.5 Hz), 2.49 (s, 3H), 1.21 (t, 3H, J=7.5 Hz).

EXAMPLE 66

5-Amino-2-ethyl-7-(trifluoromethyl)-3-(2'-(tetrazol-5-yl)biphen-4-yl)methyl-3H-imidazo[4,5-b]pyridine To a mixture of 2,6-diamino-4-trifluoromethylpyridine (173 mg) in $H_2SO_4$ (3 mL) at 0° C. was added $HNO_3$ (0.048 mL, d=1.40). The stirred mixture was sequentially warmed to RT, aged 1.5 hours, poured onto 50 g ice, neutralized with $NH_4OH$, extracted with EtOAc, filtered through 20 g $SiO_2$ (washed with EtOAc until yellow color eluted), and concentrated to give 70 mg of 2,6-diamino-3-nitro-4-trifluoromethylpyridine as a yellow solid. A 1:1 THF/MeOH solution of the nitro compound (65 mg) was hydrogenated (1 atm $H_2$, Ra-Ni, 16 hours at RT), filtered, concentrated, and converted to the title compound by the method outlined in Example 21.

FAB MS (M+ +1)=465.

$^1$H NMR (300 MHz, $CD_3OD$) δ7.61 (t, 2H, J=7.8 Hz), 7.54-7.48 (m, 2H), 7.13-7.04 (AB q, 4H), 6.74 (s, 1H), 5.41 (s, 2H), 2.79 (q, 2H, J=7.5 Hz), 1.16 (t, 3H, J=7.5 Hz).

EXAMPLE 67

2-Ethyl-5-(methylamino)-7-methyl-3-(2'-(tetrazol-5-yl)biphen-4-yl)methyl-3H-imidazo[4,5-b]pyridine A mixture of 5-Bromo-2-ethyl-7-methyl-3-(2'-(tetrazol-5-yl)biphen-4-yl)methyl-3H-imidazo[4,5-b]pyridine (74 mg), methylamine (0.6 g), and EtOH (2 mL) was heated in a bomb at 180° C. for 16 hours. Concentration and purification ($SiO_2$, 90/9/1 $CH_2Cl_2$/MeOH/$NH_4OH$) gave 34.4 mg of the title compound.

$^1$H NMR (300 MHz, $CD_3OD$) δ7.60-7.51 (m, 2H), 7.49-7.42 (m, 2H), 7.17-7.05 (m, 4H), 6.33 (s, 1H), 5.44 (s, 2H), 2.90 (s, 3H), 2.79 (q, 2H, J=7.8 Hz), 2.47 (s, 3H), 1.22 (t, 3H, J=7.8 Hz).

EXAMPLE 68

5-(Dimethylamino)-2-ethyl-7-methyl-3-(2'-(tetrazol-5-yl)biphen-4-yl)methyl-3H-imidazo[4,5-b]pyridine The title compound was prepared by using a similar method to that described in Example 67.

$^1$H NMR (300 MHz, $CD_3OD$) δ7.60-7.52 (m, 2H), 7.51-7.44 (m, 2H), 7.18-7.05 (AB q, 4H), 6.52 (s, 1H), 5.45 (s, 2H), 3.12 (s, 6H), 2.88 (q, 2H, J=7.8 Hz), 2.54 (s, 3H), 1.24 (t, 3H, J=7.8 Hz).

EXAMPLE 69

5-(Methylamino)-2-propyl-3-(2'-(tetrazol-5-yl)biphen-4-yl)methyl-3H-imidazo[4,5-b]pyridine The title compound was prepared by using a similar method to that described in Example 20.

$^1$H NMR (300 MHz, $CD_3OD$) δ7.69-7.55 (m, 3H), 7.55-7.45 (m, 2H), 7.20-7.03 (AB q, 4H), 6.52 (d, 1H J=8.7 Hz), 5.47 (s, 2H), 2.92 (s, 3H), 2.82 (t, 2H, J=7.3 Hz), 1.78-1.62 (m, 2H), 0.96 (t, 3H, J=7.4 Hz).

EXAMPLE 70

5-(Dimethylamino)-2-propyl-3-(2'-(tetrazol-5-yl)biphen-4-yl)methyl-3H-imidazo[4,5-b]pyridine The title compound was prepared by using a similar method to that described in Example 20.

$^1$H NMR (300 MHz, $CD_3OD$) δ7.67 (d, 1H, J=9 Hz), 7.60-7.40 (m, 4H), 7.18-7.00 (AB q, 4H), 6.63 (d, 1H J=9 Hz), 5.40 (s, 2H), 3.10 (s, 6H), 2.78 (t, 2H, J=7.5 Hz), 1.73-1.59 (m, 2H), 0.93 (t, 3H, J=7.4 Hz).

EXAMPLE 71

2-Ethyl-5-(hexylamino)-7-methyl-3-(2'-(tetrazol-5-yl)biphen-4-yl)methyl-3H-imidazo[4,5-b]pyridine The title compound was prepared by using a similar method to that described in Example 67.

$^1$H NMR (300 MHz, $CD_3OD$) δ7.57-7.48 (m, 2H), 7.48-7.38 (m, 2H), 7.15-7.02 (AB q, 4H), 6.28 (s, 1H), 5.38 (s, 2H), 3.33-3.28 (m, 2H), 2.80 (q, 2H, J=7.5 Hz), 2.45 (s, 3H), 1.68-1.55 (m, 2H), 1.45-1.25 (m, 8H), 1.21 (t, 3H, J=7.5 Hz),.0.87 (t, 3H, J=7.0 Hz).

EXAMPLE 72

5-(2-Aminoethyl)amino-2-ethyl-7-methyl-3-(2'-(tetrazol-5-yl)biphen-4-yl)methyl-3H-imidazo[4,5-b]pyridine The title compound was prepared by using a method similar to that described in Example 67.

$^1$H NMR (300 MHz, $CD_3OD$) δ7.67 (d, 1H, J=6.6 Hz), 7.49-7.39 (m, 3H), 7.07 (d, 2H, J=8 Hz), 6.89 (d, 2H, J=8 Hz), 6.33 (s, 1H), 5.45 (s, 2H), 3.55 (t, 2H J=5 Hz), 3.12 (t, 2H J=5 Hz), 2.89 (q, 2H, J=7.8 Hz), 2.50 (s, 3H), 1.31 (t, 3H, J=7.8 Hz).

EXAMPLE 73

5-(Carboxymethyl)amino-2-ethyl-7-methyl-3-(2'-(tetrazol-5-yl)biphen-4-yl)methyl-3H-imidazo[4,5-b]pyridine The title compound was prepared by using a similar method to that described in Example 67.

$^1$H NMR (300 MHz, $CD_3OD$) δ7.53-7.35 (m, 4H), 7.08-7.00 (AB q, 4H), 6.28 (s, 1H), 5.35 (s, 2H), 3.89 (s, 2H), 2.74 (q, 2H, J=7.5 Hz), 2.49 (s, 3H), 1.20 (t, 3H, J=7.5 Hz).

EXAMPLE 74

2-Ethyl-7-methyl-5-(4-morpholino)-3-(2'-(tetrazol-5-yl)biphen-4-yl)methyl-3H-imidazo[4,5-b]pyridine The title compound was prepared by using a similar method to that described in Example 67.

$^1$H NMR (300 MHz, $CD_3OD$) δ7.65-7.58 (m, 2H), 7.51 (t, 2H J=7.2 Hz), 7.17-7.05 (AB q, 4H), 6.67 (s, 1H), 5.45 (s, 2H), 3.81 (t, 2H J=5 Hz), 3.53 (t, 2H J=5 Hz), 2.87 (q, 2H, J=7.5 Hz), 2.56 (s, 3H), 1.24 (t, 3H, J=7.5 Hz).

EXAMPLE 75

2-Ethyl-7-methyl-5-(methylthio)-3-(2'-(tetrazol-5-yl)biphen-4-yl)methyl-3H-imidazo[4,5-b]pyridine The title compound was prepared by using a similar method to that described in Example 67.

$^1$H NMR (300 MHz, CD$_3$OD) δ7.68-7.61 (m, 2H), 7.51 (t, 2H J=7.8 Hz), 7.19-7.03 (AB q, 4H), 7.00 (s, 1H), 5.52 (s, 2H), 2.87 (q, 2H, J=7.8 Hz), 2.58 (s, 6H), 1.26 (t, 3H, J=7.8 Hz).

EXAMPLE 76

2-Ethyl-5-hydroxy-7-methyl-3-(2'-(tetrazol-5-yl)biphen-4-yl)methyl-3H-imidazo[4,5-b]pyridine The title compound was prepared by using a similar method to that described in Example 67.

$^1$H NMR (300 MHz, CD$_3$OD) δ7.61-7.52 (m, 2H), 7.51-7.43 (m, 2H), 7.06 (apparent s, 4H), 6.44 (s, 1H), 5.41 (s, 2H), 2.80 (q, 2H, J=7.5 Hz), 2.55 (s, 3H), 1.22 (t, 3H, J=7.5 Hz).

EXAMPLE 77

5-Ethoxy-2-ethyl-7-methyl-3-(2'-(tetrazol-5-yl)biphen-4-yl)methyl-3H-imidazo[4,5-b]pyridine The title compound was prepared by using a similar method to that described in Example 67.

$^1$H NMR (300 MHz, CD$_3$OD) δ7.64-7.57 (m, 2H), 7.55-7.47 (m, 2H), 7.17-7.04 (AB q, 4H), 6.52 (s, 1H), 5.45 (s, 2H), 4.35 (q, 2H, J=7.2 Hz), 2.86 (q, 2H, J=7.8 Hz), 2.56 (s, 3H), 1.37 (t, 3H, J=7.2 Hz), 1.22 (t, 3H, J=7.8 Hz).

EXAMPLE 78

5-(Acetamidoethyl)amino-2-ethyl-7-methyl-3-(2'-(tetrazol-5-yl)biphen-4-yl)methyl-3H-imidazo[4,5-b]pyridine To 5-(2-aminoethyl)amino-2-ethyl-7-methyl-3-(2'-(tetrazol-5-yl)biphen-4-yl)methyl-3H-imidazo[4,5-b]pyridine (20 mg) in THF (1 mL) at °C. was added AcCl (3.4 μL) and triethylamine (18 μL). After 1 h, the solvent was evaporated and the residue was purified (SiO$_2$, 80:20:1 CHCl$_3$, MeOH, NH$_4$OH) to give 17 mg of the title compound.

$^1$H NMR (300 MHz, CD$_3$OD) δ7.63-7.45 (m, 4H), 7.18-7.04 (AB q, 4H), 6.33 (s, 1H), 5.43 (s, 2H), 3.47 (t, 2H J=5 Hz), 3.38 (t, 2H J=5 Hz), 2.86 (q, 2H, J=7.8 Hz), 2.47 (s, 3H), 1.90 (s, 3H), 1.22 (t, 3H, J=7.8 Hz).

EXAMPLE 79

2-Ethyl-5-methyl-3-(2'-(tetrazol-5-yl)biphen-4-yl)methyl-3H-imidazo[4,5-b]pyridine The title compound was prepared by using a similar method to that described in Example 16.

$^1$H NMR (300 MHz, CDCl$_3$) δ785 (d, 1H, J=8 Hz), 7.59-7.47 (m, 2H), 7.31 (dd, 1H, J=7.2, 1.8 Hz), 7.16 (d, 1H, J=8 Hz), 6.92-6.74 (AB q, 4H), 5.32 (s, 2H), 2.54 (s, 3H), 2.52 (q, 2H), 1.12 (t, 3H).

EXAMPLE 80

5-Methyl-2-propyl-3-(2'-(tetrazol-5-yl)biphen-4-yl)methyl-3H-imidazo[4,5-b]pyridine The title compound was prepared by using a similar method to that described in Example 16.

$^1$H NMR (300 MHz, CD$_3$OD) δ787 (d, 1H, J=8 Hz), 7.69-7.58 (m, 2H), 7.59-7.49 (m,2H), 7.20 (d, 1H, J=8 Hz), 7.09 (apparent singlet, 4H), 5.57 (s, 2H), 2.80 (q, 2H, J=7.5 Hz), 2.63 (s, 3H), 0.96 (t, 3H, J=7.5 Hz).

EXAMPLE 81

6-Methyl-2-propyl-3-(2'-(tetrazol-5-yl)biphen-4-yl)methyl-3H-imidazo[4,5-b]pyridine The title compound was prepared by using a similar method to that described in Example 16.

$^1$H NMR (300 MHz, CD$_3$OD) δ8.20 (s, 1H), 7.82 (s, 1H), 7.63-7.54 (m, 2H), 7.52-7.44 (m, 2H), 7.07 (apparent singlet, 4H), 5.53 (s, 2H), 2.82 (t, 2H, J=7.5 Hz), 2.48 (s, 3H), 1.80-1.75 (m, 2H), 0.96 (t, 3H, J=7.5 Hz).

EXAMPLE 82

6-Bromo-7-methyl-2-propyl-3-(2'-(tetrazol-5-yl)biphen-4-yl)methyl-3H-imidazo[4,5-b]pyridine The title compound was prepared by using a similar method to that described in Example 10 Step 1 and Example 7.

$^1$H NMR (300 MHz, acetone-D6) δ8.35 (s, 1H), 7.78 (d, 1H), 7.68-7.48 (m, 4H), 7.18-7.08 (ABq, 4H), 5.55 (s, 2H), 2.85 (t, 2H, J=7.5 Hz), 2.67 (s, 3H), 1.80-1.75 (m, 2H), 0.98 (t, 3H, J=7.5 Hz).

EXAMPLE 83

7-Ethyl-2-propyl-3-(2'-(tetrazol-5-yl)biphen-4-yl)methyl-3H-imidazo[4,5-b]pyridine tert-Butyllithium (0.978 mL, 1.7M/pentane) was added to a cooled (−78° C.) THF (5 mL) solution of 7-methyl-2-propylimidazo[4,5-b]pyridine (97 mg, 0.554 mmol). After 2 hour the reaction was warmed to 0° C. for 1 minute then cooled back to −78° C. MeI (0.172 mL) was added, the mixture was stirred at −78° C. for 1 hour then warmed to 0° C. for 1 minute and then quenched (NH$_4$OH). Extractive workup and purification (SiO$_2$, 2% MeOH/ EtOAc) gave 85 mg of 7-ethyl-2-propylimidazo[4,5-b]pyridine which was converted to the title compound as outlined in Example 7, Part B.

$^1$H NMR (250 MHz, CD$_3$OD) δ8.28 (d, 1H, J=6 Hz), 7.72-7.65 (m, 2H), 7.62-7.54 (m, 2H), 7.22 (d, 1H, J=6 Hz), 7.17-7.08 (AB q, 4H), 5.61 (s, 2H), 3.12 (q, 2H, J=9 Hz), 2.89 (t, 2H, J=9 Hz), 1.80-1.63 (m, 2H), 1.41 (t, 3H, J=9 Hz), 0.99 (t, 3H, J=9 Hz).

EXAMPLE 84

7-Isopropyl-2-propyl-3-(2'-(tetrazol-5-yl)biphen-4-yl)methyl-3H-imidazo[4,5-b]pyridine 7-Isopropyl-2-propylimidazo[4,5-b]pyridine was prepared from 7-ethyl-2-propylimidazo[4,5-b]pyridine by the metallation-alkylation sequence described in the first part of Example 83. The title compound was prepared by using a similar method to that described in Example 7, Part B.

$^1$H NMR (300 MHz, CDCl$_3$) δ8.11 (d, 1H, J=5 Hz), 7.88 (dd, 1H, J=7.5, 1.5 Hz), 7.58-7.46 (m, 2H), 7.37-7.32 (m, 1H), 7.04 (d, 1H, J=5 Hz), 7.03-6.85 (AB q, 4H), 5.37 (s, 2H), 3.48-3.34 (m, 1H), 2.56 (t, 2H, J=7.2 Hz), 1.76-1.62 (m, 2H), 1.22 (d, 6H, J=6.6 Hz), 0.92 (t, 3H, J=7.2 Hz).

EXAMPLE 85

7-Ethyl-2-ethyl-3-(2'-(tetrazol-5-yl)biphen-4-yl)methyl-3H-imidazo[4,5-b]pyridine The title compound was prepared by using a similar method to that described in Example 83.

$^1$H NMR (250 MHz, CD$_3$OD) δ8.21 (d, 1H, J=5 Hz), 7.56–7.37 (m, 4H), 7.15 (d, 1H, J=5 Hz), 7.09–6.97 (AB q, 4H), 5.53 (s, 2H), 3.08 (q, 2H, J=8 Hz), 2.88 (q, 2H, J=7.5 Hz), 1.38 (t, 3H, J=7.5 Hz), 1.26 (t, 3H, J=7.5 Hz).

EXAMPLE 86

6-Hydroxymethyl-7-methyl-2-propyl-3-(2'-(tetrazol-5-yl)biphen-4-yl)methyl-3H-imidazo[4,5-b]pyridine To a cooled (−78° C.) stirred solution of 2-propyl-6-bromo-7-methylimidazo[4,5-b]pyridine (540 mg, 2.15 mmol) in THF (20 mL) was added tert-butyl-lithium (4.40 mL, 1.7M/pentane) over 30 seconds After 45 minutes, dimethylformamide (0.665 mL) was added and after 10 additional minutes the reaction was warmed to RT and quenched with 20% aqueous 4 NH$_4$Cl. Extractive workup EtOAc (4×10 mL) and purification (SiO$_2$, 4% MeOH/EtOAc) gave 2-propyl-7-methylimidazo[4,5-b]pyridine-6-carboxaldehyde (350 mg). To a stirred, cooled (0° C.) methanolic (15 mL) solution of the aldehyde (300 mg) was added NaBH$_4$ (84 mg). After 30 minutes HOAc (0.1 mL) was added, the mixture was warmed (RT), concentrated, and purified (SiO$_2$, 10% MeOH/CH$_2$Cl$_2$) to give 190 mg of 6-hydroxymethyl-7-methyl-2-propylimidazo[4,5-b]pyridineas an oil. The title compound was prepared by using a similar method to that described in Example 7, Part B.

$^1$H NMR (300 MHz, CD$_3$OD) δ8.25 (s, 1H), 7.59–7.41 (m, 4H), 7.18–7.09 (ABq, 4H), 5.52 (s, 2H), 4.79 (s, 2H), 2.83 (t, 2H, J=7.5 Hz), 2.70 (s, 3H), 1.78–1.63 (m, 2H), 0.96 (t, 3H, J=7.5 Hz).

EXAMPLE 87

2-Propyl-7-(p-tolyl)-3-(2'-(tetrazol-5-yl)biphen-4-yl)methyl-3H-imidazo[4,5-b]pyridine The title compound was prepared by using a similar method to that described in Example 55.

$^1$H NMR (300 MHz, CDCl$_3$) δ7.95–7.84 (m, 3H), 7.62–7.49 (m, 3H), 7.43–7.33 (m, 2H), 7.28–7.22 (m, 2H), 6.98–6.93 (AB q, 4H), 5.45 (s, 2H), 2.49 (t, 2H, J=7.5 Hz), 2.38 (s, 3H), 1.68–1.54 (m, 2H), 0.83 (t, 3H, J=7.5 Hz).

EXAMPLE 88

2-Propyl-7-methyl-6-(p-tolyl)-3-(2'-(tetrazol-5-yl)biphen-4-yl)methyl-3H-imidazo[4,5-b]pyridine The title compound was prepared by using a similar method to that described in Example 55.

$^1$H NMR (300 MHz, CDCl$_3$) δ8.13 (s, 1H), 7.64–7.54 (m, 2H), 7.54–7.44 (m, 2H), 7.32–7.24 (m, 2H), 7.16–7.04 (m, 6H), 5.57 (s, 2H), 2.87 (t, 2H, J=7.5 Hz), 2.57 (s, 3H), 2.42 (s, 3H), 1.78–1.65 (m, 2H), 0.99 (t, 3H, J=7.5 Hz).

EXAMPLE 89

5-Chloro-2-propyl-3-(2'-(tetrazol-5-yl)biphen-4-yl)methyl-3H-imidazo[4,5-b]pyridine The title compound was prepared starting with 5-chloro-2,3-pyridinediamine by using a similar method to that described in Example 9.

$^1$H NMR (300 MHz, 1:1 CD$_3$OD/CDCl$_3$) δ7.90 (d, 1H, J=8.4 Hz), 7.64–7.39 (m, 4H), 7.24 (d, 1H, J=8.4 Hz), 7.10–7.00 (ABq, 4H), 5.44 (s, 2H), 2.73 (t, 2H, J=7.5 Hz), 1.81–1.67 (m, 2H), 0.94 (t, 3H, J=7.5 Hz).

EXAMPLE 90

6-Amino-5,7-dimethyl-2-propyl-3-(2'-(tetrazol-5-yl)biphen-4-yl)methyl-3H-imidazo[4,5-b]pyridine The title compound was prepared starting with 3,5,6-triamino-2,4-lutidine by using a similar method to that described in Example 20.

$^1$H NMR (300 MHz, CD$_3$OD) δ7.62–7.52 (m, 2H), 7.52–7.42 (m, 2H), 7.06, (s, 4H), 5.53 (s, 2H), 2.85 (t, 2H, J=7.5 Hz), 2.53 (s, 3H), 2.45 (s, 3H), 1.72–1.55 (m, 2H), 0.93 (t, 3H, J=7.5 Hz).

EXAMPLE 91

7-Methyl-2-propyl-3-(2'-(tetrazol-5-yl)biphen-4-yl)methyl-3H-imidazo[4,5-b]pyridine-4-oxide A solution of 7-Methyl-2-propyl-3-(2'-(tetrazol-5-yl)biphen-4-yl)methyl-3H-imidazo[4,5-b]pyridine (9 mg) and m-chloroperoxybenzoic acid (6 mg) CHCl$_3$ (2 mL) was heated to reflux for 2 hours. Concentration and purification (SiO2, 80:20:1 CH$_2$Cl$_2$/MeOH/NH$_4$OH) gave 4 mg of the title compound as a solid.

$^1$H NMR (300 MHz, CD$_3$OD) δ8.07 (d, 1H, J=6 Hz), 7.60–7.43 (m, 4H), 7.19, (d, 1H, J=6 Hz), 7.09 (s, 4H), 6.14 (s, 2H), 2.82 (t, 2H, J=7.5 Hz), 2.63 (s, 3H), 1.81–1.67 (m, 2H), 0.98 (t, 3H, J=7.5 Hz).

EXAMPLE 92

5,7-Dimethyl-6-hydroxy-2-propyl-3-(2'-(tetrazol-5-yl)biphen-4-yl)methyl-3H-imidazo[4,5-b]pyridine The title compound can be prepared by diazotization of 6-Amino-5,7-dimethyl-2-propyl-3-(2'-(tetrazol-5-yl)biphen-4-yl)methyl]-3H-imidazo[4,5-b]pyridine in conc. HCl with 1 equiv of NaNO$_2$ at RT followed by heating to 80° C. for 2 hours and subsequent neutralization (NH$_4$OH), extraction, and purification.

EXAMPLE 93

5,7-Dimethyl-2-(3,3,3-trifluoroprop-2-yl)-3-(2'-(tetrazol-5-yl)biphen-4-yl)methyl-3H-imidazo[4,5-b]pyridine The title compound was prepared in a manner similar to Example 16.

FAB MS (M+ +1)=478.

EXAMPLE 94

2-(3-Butyn-1-yl)-5,7-dimethyl-3-(2'-(tetrazol-5-yl)biphen-4-yl)methyl-3H-imidazo[4,5-b]pyridine The title compound was prepared in a manner similar to Example 16. R$_f$=0.52. (tlc, Merck Kieselgel 60 F-254, 40/10/1 CHCl$_3$ MeOH NH$_4$OH).

EXAMPLE 95

5,7-Dimethyl-2-methyl-3-(2'-(tetrazol-5-yl)biphen-4-yl)methyl-3H-imidazo[4,5-b]pyridine The title compound was prepared in a manner similar to Example 16.

FAB MS (M+ +1)=396.

$^1$H NMR (300 MHz, CD$_3$OD) δ7.62–7.53 (m, 2H), 7.52–7.44 (m, 2H), 7.08–7.00 (AB q, 4H), 7.02 (s, 1H), 5.51 (s, 2H), 2.58 (s, 3H), 2.50 (s, 3H).

EXAMPLE 96

7-Chloro-2-ethyl-5-methyl-3-(2'-(tetrazol-5-yl)biphen-4-yl)methyl-3H-imidazo[4,5-b]pyridine The title compound was prepared by using a similar method to that described in Example 44, Step 1, and Example 45 starting with 5-methyl-2-ethylimidazo[4,5-b]pyridine.

$^1$H NMR (300 MHz, CD$_3$OD) δ7.68–7.56 (m, 2H), 7.58–7.48 (m, 2H), 7.26 (s, 1H), 7.10 (s, 4H), 5.55 (s, 2H), 2.86 (q, 2H, J=7.5 Hz), 2.61 (s, 3H), 1.25 (t, 3H, J=7.5 Hz).

EXAMPLE 97

2-Ethyl-5-methyl-7-(4-morpholino)-3-(2'-(tetrazol-5-yl)biphen-4-yl)methyl-3H-imidazo[4,5-b]pyridine The title compound was prepared starting with 7-chloro-2-ethyl-5-methyl-3-(2'-(tetrazol-5-yl)biphen-4-yl)methyl-3H-imidazo[4,5-b]pyridine by using a similar method to that described in Example 67.

$^1$H NMR (300 MHz, CD$_3$OD) δ7.60–7.50 (m, 2H), 7.50–7.42 (m, 2H), 7.12–6.90 (ABq, 4H) 6.51 (s, 1H), 5.45 (s, 2H), 3.95–3.78 (m, 8H), 2.74 (q, 2H, J=7.5 Hz), 2.50 (s, 3H), 1.22 (t, 3H, J=7.5 Hz).

EXAMPLE 98

2-Ethyl-5-methyl-7-(methylamino)-3-(2'-(tetrazol-5-yl)biphen-4-yl)methyl-3H-imidazo[4,5-b]pyridine The title compound was prepared by using a similar method to that described in Example 96.

$^1$H NMR (300 MHz, CD$_3$OD) δ7.58–7.49 (m, 2H), 7.49–7.40 (m, 2H), 7.11–6.90 (ABq, 4H) 6.37 (s, 1H), 5.45 (s, 2H), 3.04 (s, 3H), 2.75 (q, 2H, J=7.5 Hz), 2.51 (s, 3H), 1.26 (t, 3H, J=7.5 Hz).

EXAMPLE 99

7-(Dimethylamino)-2-ethyl-5-methyl-3-(2'-(tetrazol-5-yl)biphen-4-yl)methyl-3H-imidazo[4,5-b]pyridine The title compound was prepared by using a similar method to that described in Example 96.

$^1$H NMR (300 MHz, CD$_3$OD) δ7.58–7.39 (m, 4H), 7.13–6.87 (ABq, 4H) 6.36 (s, 1H), 5.45 (s, 2H), 3.46 (s, 6H), 2.73 (q, 2H, J=7.5 Hz), 2.49 (s, 3H), 1.25 (t, 3H, J=7.5 Hz).

EXAMPLE 100

2-Ethyl-5-methyl-7-(methylthio)-3-(2'-(tetrazol-5-yl)biphen-4-yl)methyl-3H-imidazo[4,5-b]pyridine The title compound was prepared by using a similar method to that described in Example 75.

$^1$H NMR (300 MHz, CD$_3$OD) δ7.55–7.38 (m, 4H), 7.18–6.95 (ABq, 4H) 7.00 (s, 1H), 5.49 (s, 2H), 2.81 (q, 2H, J=7.5 Hz), 2.62 (s, 3H), 2.60 (s, 3H), 1.22 (t, 3H, J=7.5 Hz).

EXAMPLE 101

5,7-Dimethyl-2-ethyl-3-(4'-chloro-2'-(tetrazol-5-yl)biphen-4-yl)methyl-3H-imidazo[4,5-b]pyridine Step 1: 2-Cyano-4-nitro-4'-methylbiphenyl To a solution of p-tolyltrimethyltin (389 mg, 1.525 mmol) in dry toluene (5 mL) under N$_2$ was added 2-bromo-5-nitro-benzonitrile (276 mg, 1.22 mmol) and Pd(PPh$_3$)$_4$ (176 mg; 10 mol %). The reaction was stirred at reflux under N$_2$ for 24 hours and then cooled to room temperature. The mixture was diluted with EtOAc and the solid was removed by filtration through a pad of celite. The filtrate was concentrated in vacuo and the residue was purified by flash chromatography on a silica column eluting with Hex/EtOAc (10:1) to afford 214 mg (74%) of the titled compound as a slightly yellow solid.

$^1$H NMR (300 MHz, CDCl$_3$) δ2.42 (s, 3H), 7.32 (d, 2H), 7.48 (d, 2H), 7.69 (d, 1H), 8.45 (dd, 1H), 8.61 (s, 1H).

Step 2: N-Triphenylmethyl-5-(4'-methyl-4-nitrobiphen-2-yl)tetrazole

The titled compound was prepared starting from 2-cyano-4-nitro-4'-methylbiphenyl (step 1) according to procedures described in European Patent Application EP 0,291,969.

$^1$H NMR (300 MHz, CDCl$_3$) δ2.28 (s, 3H), 6.89 (d, 6H), 6.98 (ABq, 4H), 7.22–7.37 (comp, 9H), 7.56 (d, 1H), 8.31 (dd, 1H), 8.75 (d, 1H).

Step 3: N-Triphenylmethyl-5-(4-chloro-4'-methylbiphen-2-yl)tetrazole

A solution of N-Triphenylmethyl-5-(4'-methyl-4-nitrobiphen-2-yl)tetrazole (0.115 g, 0.224 mmol) in MeOH/DMF (2 mL/12 mL) was submitted to hydrogenation at 40 psi H$_2$ with 10% Pd on carbon (50 mg) at room temperature for 1 hour. The reaction was filtered through celite and the filtrate was concentrated in vacuo. The triphenyl methyl group had been lost during the hydrogenation. The crude 4-amino compound was dissolved in glacial acetic acid (3 mL) and added slowly to a cooled (0° C.) solution of NaNO$_2$ (28.8 mg, 0.417 mmol) in conc. sulfuric acid (1 mL). The diazonium solution was stirred well for 2 hoursr then slowly added to a cooled (0° C.) solution of CuCl (0.449 g; 20 equiv) in conc. HCl. This mixture was stirred for 30 minutes and then poured over H$_2$O and extracted with Et$_2$O/EtOAc. The combined organic extracts were washed with H$_2$O and brine, dried over MgSO$_4$ and concentrated in vacuo. The product was purified by flash chromatography on a silica column eluting with Hex/EtOAc/HOAc (80:20;1) to afford 27 mg (45% for 2 steps) of 5-(4-chloro-4'-methyl-biphen-2-yl)tetrazole. The free tetrazole was dissolved in CH$_2$Cl$_2$ (3.5 mL) and NEt$_3$ (0.035 mL, 2.5 equiv) and Ph$_3$CCl (27 mg, 1.0 equiv) were added. After 30 minutes the reaction was diluted with Et$_2$O washed with 10% citric acid, 1N NaOH and brine. The organic was dried over anhydrous MgSO$_4$ and concentrated in vacuo to afford 51.2 mg (100%) of crude N-triphenylmethyl-5-(4-chloro-4'-methyl-biphen-2-yl)tetrazole.

$^1$H NMR (300 MHz, CDCl$_3$) δ2.26 (s, 3H), 6.91 (d, 6H), 6.94 (ABq, 4H), 7.20–7.25 (comp, 7H), 7.43 (dd, 1H), 7.99 (dd, 1H).

Step 4: N-Triphenylmethyl-5-(4'-bromomethyl-4-chlorobiphen-2-yl)tetrazole

The titled compound was prepared starting from N-Triphenylmethyl-5-(4-chloro-4'-methyl-biphen-2-yl)tetrazole (step 1 to 3) according to procedures described in European Patent Application EP 0,291,969.

Step 5: 5,7-Dimethyl-2-ethyl-3-(4'-chloro-2'-(tetrazol-5-yl)biphen-4-yl)methyl-3H-imidazo[4,5-b]pyridine The title compound was prepared from 5,7-dimethyl-2-ethylimidazo[4,5-b]pyridine and N-triphenylmethyl-5-(4'-bromomethyl-4-chlorobiphen-2-yl)tetrazole in a manner similar to Example 7, and was isolated as an HCl salt.

$^1$H NMR (300 MHz, CD$_3$OD) δ1.38 (t, 3H), 2.72 (s, 6H), 3.28 (q, 2H), 5.82 (s, 2H), 7.18 (d, 2H), 7,36 (d, 2H), 7.44 (s, 1H), 7.58 (d, 1H), 7.72 (dd, 1H), 7.76 (d, 1H).

FAB mass spectrum, m/e 444 (M+H, calcd for $C_{24}H_{22}N_7Cl$, 444).

EXAMPLE 102

5,7-Dimethyl-2-ethyl-3-(4'-fluoro-2'-(tetrazol-5-yl)biphen-4-yl)methyl-3H-imidazo[4,5-b]-pyridine Table I shows intermediates that were used to make this and other angiotensin II antagonists in a manner similar to Example 102.

EXAMPLE 103

5-(Acetoxymethyl)-2-ethyl-7-methyl-3-(2'-tetrazol-5-yl)biphen-4-yl)methyl-3H-imidazo[4,5-b]pyridine A mixture of 2-Ethyl-5-(hydroxymethyl)-7-methyl-3-((2'-tetrazol-5-yl)biphen-4-yl)methyl-3H-imidazo[4,5-b]pyridine (34 mg), acetic anhydride (0.25 mL), and triethylamine (0.5 mL) in $CH_2Cl_2$ (2 mL) was stirred at rt for 3 hours. Extractive (EtOAc) work up from dilute aqueous HOAc and purification ($SiO_2$, 80/20/1 $CH_2Cl_2$/MeOH/$NH_4OH$) gave 30 mg of the title compound.

FAB MS: M+1=468.

$^1$H NMR (300 MHz, $CD_3OD$) $\delta$7.66-7.57 (m, 2H), 7.55-7.46 (m, 2H), 7.19 (s, 1H), 7.13-7.02 (AB quartet, 4H), 5.53 (s, 2H), 5.23 (s, 2H), 2.86 (q, 2H, J=7.5 Hz), 2.63 (s, 3H), 2.11 (s, 3H), 1.25 (t, 3H, J=7.5 Hz).

EXAMPLE 104

Typical Pharmaceutical Compositions Containing a Compound of the Invention

A: Dry Filled Capsules Containing 50 mg of Active Ingredient Per Capsule

| Ingredient | Amount per capsule (mg) |
| --- | --- |
| 7-methyl-2-propyl-3-(2'-(tetrazol-5-yl)biphen-4-yl)methyl-3H-imidazo[4,5-b]pyridine | 50 |
| Lactose | 149 |
| Magnesium stearate | 1 |
| Capsule (size No. 1) | 200 |

The 7-methyl-2-propyl-3-(2'-(tetrazol-5-yl)biphen-4-yl)methyl-3H-imidazo[4,5-b]pyridine can be reduced to a No. 60 powder and the lactose and magnesium stearate can then be passed through a No. 60 blotting cloth onto the powder. The combined ingredients can then be mixed for about 10 minutes and filled into a No. 1 dry gelatin capsule.

B: Tablet

A typical tablet would contain 7-methyl-2-propyl-3-(2'-(tetrazol-5-yl)biphen-4-yl)methyl-3H-imidazo[4,5-b]pyridine(25 mg), pregelatinized starch USP (82 mg), microcrystaline cellulose (82 mg) and magnesium stearate (1 mg).

C: Combination Tablet

A typical combination tablet would contain, for example, a diuretic such as hydrochlorothiazide and consist of (7.5 mg), hydrochlorothiazide (50 mg) pregelatinized starch USP (82 mg), microcrystalline cellulose (82 mg) and magnesium stearate (1 mg).

D: Suppository

Typical suppository formulations for rectal administration can contain 7-methyl-2-propyl-3-(2'-(tetrazol-5-yl)biphen-4-yl)methyl-3H-imidazo[4,5-b]pyridine (1-25 mg), butylated hydroxyanisole (0.08-1.0 mg), disodium calcium edetate (0.25-0.5 mg), and polyethylene glycol (775-1600 mg). Other suppository formulations can be made by substituting, for example, butylated hydroxytoluene (0.04-0.08 mg) for the disodium calcium edetate and a hydrogenated vegetable oil (675-1400 mg) such as Suppocire L, Wecobee FS, Wecobee M, Witepsols, and the like, for the polyethylene glycol. Further, these suppository formulations can also include another active ingredient such as another antihypertensive and/or a diuretic and/or an angiotensin converting enzyme and/or a calcium channel blocker in pharmaceutically effective amounts as described, for example, in C above.

E: Injection

A typical injectible formulation would contain 7-methyl-2-propyl-3-(2'-(tetrazol-5-yl)biphen-4-yl)methyl-3H-imidazo[4,5-b]pyridine (5.42 mg), sodium phosphate dibasic anhydrous (11.4 mg) benzyl alcohol (0.01 ml) and water for injection (1.0 ml). Such as injectible formulation can also include a pharmaceutically effective amount of another active ingredient such as another antihypertensive and/or a diuretic and/or an angiotensin converting enzyme inhibitor and/or a calcium channel blocker.

What is claimed is:

1. A compound of structural formula:

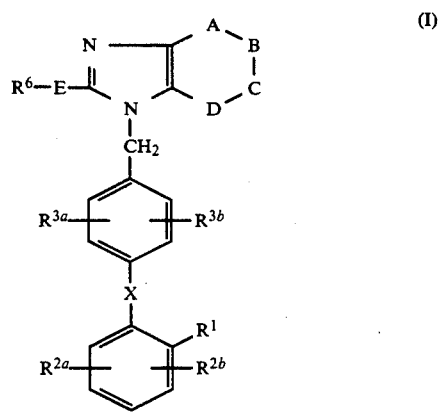

(I)

wherein:
$R^1$ is
(a) —$CO_2R^4$,
(b) —$SO_3R^5$,
(c) —$NHSO_2CF_3$,
(d) —$PO(OR^5)_2$,
(e) —$SO_2$—NH—$R^9$,
(f) —$CONHOR^5$,
(g)

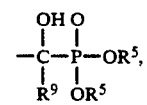

(h) —$SO_2NH$-heteroaryl,
(i) —$CH_2SO_2NH$-heteroaryl,
(j) —$SO_2NHCO$—$R^{23}$,
(k) —$CH_2SO_2NHCO$—$R^{23}$,
(l) —$CONH$—$SO_2R^{23}$,
(m) —$CH_2CONH$—$SO_2R^{23}$,
(n) —$NHSO_2NHCO$—$R^{23}$,
(o) —$NHCONHSO_2$—$R^{23}$,
(p) —$SO_2NHCONR^{23}$, (q) 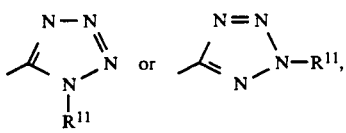

(r) 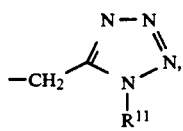

(s) 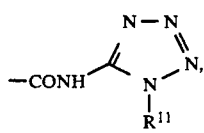

(t) —CONHNHSO₂CF₃, (u) 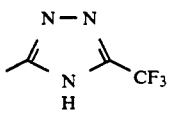

(v) 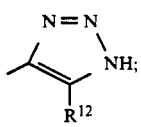

(w) 

wherein heteroaryl is an unsubstituted, monosubstituted or disubstituted five- or six-membered aromatic ring which can optionally contain 1 to 3 heteroatoms selected from the group consisting of O, N or S and wherein the substituents are members selected from the group consisting of —OH, —SH, —$C_1$-$C_4$-alkyl, —$C_1$-$C_4$-alkoxy, halo, —NO₂, —CO₂H, —CO₂—$C_1$-$C_4$-alkyl, —NH₂, —NH($C_1$-$C_4$-alkyl) and —N($C_1$-$C_4$-alkyl)₂;

$R^{2a}$ and $R^{2b}$ are independently H, halo, —NO₂, —NH₂, $C_1$-$C_4$-alkylamino, di($C_1$-$C_4$ alkyl)amino, —SO₂NHR⁹, CF₃, $C_1$-$C_4$-alkyl, or $C_1$-$C_4$-alkoxy;

$R^{3a}$ is
(a) H,
(b) halo
(c) $C_1$-$C_6$-alkyl,
(d) $C_1$-$C_6$-alkoxy,
(e) $C_1$-$C_6$-alkoxyalkyl;

$R^{3b}$ is
(a) H,
(b) halo
(c) NO₂,
(d) $C_1$-$C_6$-alkyl,
(e) $C_1$-$C_6$-acyloxy,
(f) $C_1$-$C_6$-cycloalkyl
(g) $C_1$-$C_6$-alkoxy,
(h) —NHSO₂R⁴,
(i) hydroxy $C_1$-$C_4$-alkyl,
(j) aryl $C_1$-$C_4$-alkyl
(k) $C_1$-$C_4$-alkylthio
(l) $C_1$-$C_4$-alkyl sulfinyl
(m) $C_1$-$C_4$-alkyl sulfonyl
(n) NH₂
(o) $C_1$-$C_4$-alkylamino
(p) $C_1$-$C_4$-dialkylamino
(q) fluoro $C_1$-$C_4$-alkyl
(r) —SO₂—NHR⁹
(s) aryl or,
(t) furyl;

wherein aryl is phenyl or naphthyl optionally substituted with one or two substituents selected from the group consisting of halo, $C_1$-$C_4$-alkyl, $C_1$-$C_4$-alkoxy, NO₂, CF₃, $C_1$-$C_4$-alkylthio, OH, NH₂, NH($C_1$-$C_4$-alkyl), N($C_1$-$C_4$-alkyl)₂, CO₂H, and CO₂—$C_1$-$C_4$-alkyl;

$R^4$ is H, straight chain or branched $C_1$-$C_6$ alkyl, aryl or —CH₂-aryl where aryl is as defined above;

$R^{4a}$ is $C_1$-$C_6$-alkyl, aryl or —CH₂-aryl where aryl is as defined above;

$R^5$ is H,

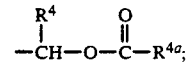

E is a single bond, —NR¹³(CH₂)ₛ—, —S(O)ₓ—(CH₂)ₛ— where x is 0 to 2 and s is 0 to 5, —CH(OH)—, —O—, —CO—;

$R^6$ is
(a) aryl as defined above optionally substituted with 1 or 2 substituents selected from the group consisting of halo —O—$C_1$-$C_4$-alkyl, $C_1$-$C_4$-alkyl, —NO₂, —CF₃, —SO₂NR⁹R¹⁰, —S—$C_1$-$C_4$-alkyl, —OH, —NH₂, $C_3$-$C_7$-cycloalkyl, $C_3$-$C_{10}$-alkenyl;
(b) straight chain or branched $C_1$-$C_9$-alkyl, $C_2$-$C_6$-alkenyl or $C_2$-$C_6$-alkynyl each of which can be optionally substituted with a substituent selected from the group consisting of aryl as defined above, $C_3$-$C_7$-cycloalkyl, halo —OH, —NH₂, —NH($C_1$-$C_4$-alkyl), —CF₂CF₃, —N($C_1$-$C_4$-alkyl)₂, —NH—SO₂R⁴, —COOR⁴, —CF₃, —CF₂CH₃, —SO₂NHR⁹; or
(c) an unsubstituted, monosubstituted or disubstituted aromatic 5 or 6 membered ring which contains one or two members selected from the group consisting of N, O, S, and wherein the substituents are members selected from the group consisting of —OH, —SH, $C_1$-$C_4$-alkyl, $C_1$-$C_4$-alkyloxy—CF₃, halo, or NO₂,
(d) perfluoro-$C_1$-$C_4$-alkyl,
(e) $C_3$-$C_7$-cycloalkyl optionally mono- or disubstituted with $C_1$-$C_4$-alkyl or —CF₃;

$R^9$ is H, $C_1$-$C_5$-alkyl, aryl or —CH₂-aryl where aryl is as defined above;

$R^{10}$ is H, $C_1$-$C_4$-alkyl;

$R^{11}$ is H, $C_1$-$C_6$-alkyl, $C_2$-$C_4$-alkenyl, $C_1$-$C_4$-alkoxy-$C_1$-$C_4$-alkyl, or

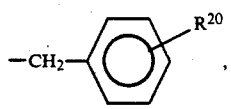

$R^{12}$ is —CN, —$NO_2$ or —$CO_2R^4$;
$R^{13}$ is H, —CO($C_1$-$C_4$-alkyl), $C_1$-$C_6$-alkyl, allyl, $C_3$-$C_6$-cycloalkyl, phenyl or benzyl;
$R^{14}$ is H, $C_1$-$C_8$-alkyl, $C_1$-$C_8$-perfluoroalkyl, $C_3$-$C_6$-cycloalkyl, phenyl or benzyl;
$R^{15}$ is H, $C_1$-$C_6$-alkyl;
$R^{16}$ is H, $C_1$-$C_6$-alkyl, $C_3$-$C_6$-cycloalkyl, phenyl or benzyl;
$R^{17}$ is —$NR^9R^{10}$, —$OR^{10}$, —$NHCONH_2$, —$NHCSNH_2$,

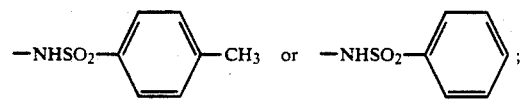

$R^{18}$ and $R^{19}$ are independently $C_1$-$C_4$-alkyl or taken together are —$(CH_2)_q$— where q is 2 or 3;
$R^{20}$ is H, —$NO_2$, —$NH_2$, —OH or —$OCH_3$;
$R^{23}$ is
 (a) aryl as defined above,
 (b) heteroaryl as defined above,
 (c) $C_3$-$C_4$-cycloalkyl,
 (d) $C_1$-$C_4$-alkyl which can be optionally substituted with a substituent that is a member selected from the group consisting of aryl as defined above, heteroaryl as defined above, —OH, —SH, —$C_1$-$C_4$-alkyl, —O($C_1$-$C_4$-alkyl), —S($C_1$-$C_4$-alkyl), —$CF_3$, halo —$NO_2$, —$CO_2H$, —$CO_2$—$C_1$-$C_4$-alkyl, —$NH_2$, NH($C_1$-$C_4$-alkyl), —$NHCOR^{4a}$, —N($C_1$-$C_4$-alkyl)$_2$, —$PO_3H$, —PO(OH) ($C_1$-$C_4$-alkyl), —PO(OH) (aryl) or —PO(OH) (O—$C_1$-$C_4$-alkyl),
 (e) perfluoro-$C_1$-$C_4$-alkyl;
X is
 (a) a carbon-carbon single bond,
 (b) —CO—,
 (c) —O—,
 (d) —S—,
 (e)

(f)

(g)

(h) —$OCH_2$—,
(i) —$CH_2O$—

(j) —$SCH_2$—,
(k) —$CH_2S$—,
(l) —$NHC(R^9)(R^{10})$—,
(m) —$NR^9SO_2$—,
(n) —$SO_2NR^9$—,
(o) —$C(R^9)(R^{10})NH$—,
(p) —CH=CH—,
(q) —CF=CF—,
(r) —CH=CF—,
(s) —CF=CH—,
(t) —$CH_2CH_2$—,
(u) —$CF_2CF_2$—,
(v)

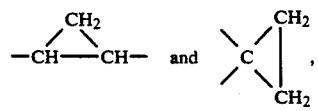

(w)

(x)

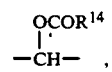

(y)

or (z)

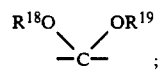

—A—B—C—D— represents

1) 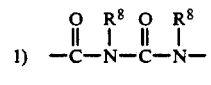

or

2) 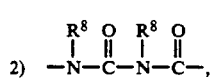

$R^8$ groups can be the same or different and represent:
 a) hydrogen,
 b) $C_1$-$C_6$-alkyl or alkenyl either unsubstituted or substituted with hydroxy, $C_1$-$C_4$-alkoxy, —N($R^4$)$_2$, —$CO_2R^4$ or $C_3$-$C_5$-cycloalkyl,
 c) $C_3$-$C_5$-cycloalkyl, with the proviso that both $R^8$ groups cannot be hydrogen;
the pharmaceutically acceptable salts thereof.

2. The compound of claim 1, wherein:
$R^1$ is:
 a) —$CO_2R^4$
 b) —$NHSO_2CF_3$
 c)

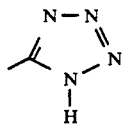

d)

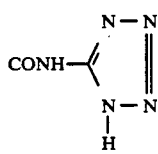

(e) —SO$_2$NH-heteroaryl,
(f) —CH$_2$SO$_2$NH-heteroaryl,
(g) —SO$_2$NHCOR$^{23}$,
(h) —CH$_2$SO$_2$NHCOR$^{23}$,
(i) —CONHSO$_2$R$^{23}$,
(j) —CH$_2$CONHSO$_2$R$^{23}$,
(k) —NHSO$_2$NHCOR$^{23}$, or
(l) —NHCONHSO$_2$R$^{23}$,
(m) —SO$_2$NHCONHR$^{23}$, wherein heteroaryl is as defined in claim 1;
X is a single bond;
R$^{2a}$ and R$^{2b}$ are independently:
 a) C$_1$-C$_4$-alkyl,
 b) halogen,
 c) hydrogen;
R$^{3a}$ and R$^{3b}$ are independently:
 a) C$_1$-C$_6$-alkyl,
 b) halogen, or
 c) C$_1$-C$_6$-alkoxy,
 d) hydrogen;
R$^4$ is H, or C$_1$-C$_4$-alkyl;
E is a single bond or —S—;
R$^6$ is a branched or straight chain C$_1$-C$_6$-alkyl, C$_3$-C$_7$-cycloalkyl, C$_2$-C$_6$-alkenyl or C$_2$-C$_6$-alkynyl each of which is either unsubstituted or substituted with C$_1$-C$_4$-alkylthio, C$_1$-C$_4$-alkoxy, CF$_3$, CF$_2$CF$_3$ or —CF$_2$CH$_3$;
and the R$^8$ groups are the same or different and represent,
 a) hydrogen,
 b) C$_1$-C$_4$-alkyl either unsubstituted or substituted with —OH or —CO$_2$R$^4$; and with the proviso that both R$^8$ groups cannot be hydrogen.

3. A pharmaceutical formulation for the treatment of hypertension and congestive heart failure comprising a pharmaceutically acceptable carrier and an effective antihypertensive amount of the compound of claim 1.

4. A method of treating hypertension and congestive heart failure comprising the administration of an effective antihypertensive amount of the compound of claim 1 to a patient in need of such treatment.

5. An ophthalmological formulation for the treatment of ocular hypertension comprising an ophthalmologically acceptable carrier and an effective ocular antihypertensive amount of a compound of claim 1.

6. A method of treating ocular hypertension comprising administering to a patient in need of such treatment an effective ocular antihypertensive amount of a compound of claim 1.

* * * * *